United States Patent
Seo et al.

(10) Patent No.: US 9,394,280 B2
(45) Date of Patent: Jul. 19, 2016

(54) HETEROCYCLIC COMPOUND, LIGHT-EMITTING ELEMENT, LIGHT-EMITTING DEVICE, ELECTRONIC DEVICE, AND LIGHTING DEVICE

(75) Inventors: Satoshi Seo, Kanagawa (JP); Satoko Shitagaki, Kanagawa (JP); Miyako Morikubo, Kanagawa (JP); Naoaki Hashimoto, Kanagawa (JP); Takahiro Ishisone, Kanagawa (JP); Kyoko Takeda, Kanagawa (JP); Hiromi Seo, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 717 days.

(21) Appl. No.: 13/598,253

(22) Filed: Aug. 29, 2012

(65) Prior Publication Data
US 2013/0082591 A1 Apr. 4, 2013

(30) Foreign Application Priority Data
Aug. 30, 2011 (JP) ................. 2011-187669

(51) Int. Cl.
*H01L 51/50* (2006.01)
*C07D 403/14* (2006.01)
(Continued)

(52) U.S. Cl.
CPC ............ *C07D 403/14* (2013.01); *C07D 409/14* (2013.01); *C09K 11/06* (2013.01);
(Continued)

(58) Field of Classification Search
CPC .. C07D 403/14; C07D 409/14; C07D 413/10; H01L 51/006; H01L 51/0071; H01L 51/0074; H01L 51/5012; H01L 51/54; H05B 33/14; C09K 11/06

See application file for complete search history.

(56) References Cited

U.S. PATENT DOCUMENTS
6,723,445 B2 4/2004 Li et al.
7,355,340 B2 4/2008 Shitagaki et al.
(Continued)

FOREIGN PATENT DOCUMENTS
JP 2007-189001 A 7/2007
JP 2008-239613 A 10/2008
(Continued)

OTHER PUBLICATIONS
Machine translation for KR 10-2011-0042004 (publication date: Apr. 2011).*
(Continued)

*Primary Examiner* — Dawn Garrett
(74) *Attorney, Agent, or Firm* — Fish & Richardson P.C.

(57) ABSTRACT

To provide a novel heterocyclic compound that can be used as a host material in which a light-emitting substance of a light-emitting layer is dispersed. A heterocyclic compound comprising a dibenzo[f,h]quinoxaline ring and two hole-transport skeletons, where the dibenzo[f,h]quinoxaline ring and the two hole-transport skeletons are bonded to an aromatic hydrocarbon group. A heterocyclic compound represented by the following general formula (G1) is provided.

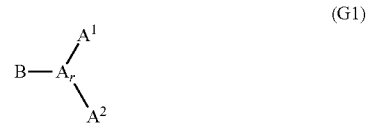

(G1)

Note that in the formula, $A^1$ and $A^2$ each independently represent any of a substituted or unsubstituted carbazole skeleton, a substituted or unsubstituted dibenzofuran skeleton, and a substituted or unsubstituted dibenzothiophen skeleton; B represents a substituted or unsubstituted dibenzo[f,h]quinoxaline skeleton; and Ar represents an arene skeleton having 6 to 13 carbon atoms. A light-emitting element including the heterocyclic compound is provided.

22 Claims, 20 Drawing Sheets

(51) Int. Cl.
*C07D 409/14* (2006.01)
*H05B 33/14* (2006.01)
*C09K 11/06* (2006.01)
*H01L 51/00* (2006.01)

(52) U.S. Cl.
CPC ......... *H01L 51/006* (2013.01); *H01L 51/0071* (2013.01); *H01L 51/0074* (2013.01); *H01L 51/5012* (2013.01); *H05B 33/14* (2013.01)

(56) References Cited

U.S. PATENT DOCUMENTS

| | | | |
|---|---|---|---|
| 8,178,216 | B2 | 5/2012 | Nomura et al. |
| 2004/0076853 | A1* | 4/2004 | Jarikov ................. 428/690 |
| 2009/0072718 | A1 | 3/2009 | Nomura et al. |
| 2009/0140641 | A1 | 6/2009 | Nomura et al. |
| 2009/0140642 | A1 | 6/2009 | Kadoma et al. |
| 2009/0153041 | A1 | 6/2009 | Kawakami et al. |
| 2009/0184633 | A1 | 7/2009 | Kadoma et al. |
| 2009/0203704 | A1 | 8/2009 | Kadoma et al. |
| 2010/0039024 | A1 | 2/2010 | Wendeborn et al. |
| 2010/0249349 | A1 | 9/2010 | Chebotareva et al. |
| 2011/0089407 | A1 | 4/2011 | Schmidhalter et al. |
| 2011/0210316 | A1 | 9/2011 | Kadoma et al. |
| 2013/0048971 | A1* | 2/2013 | Kitano et al. ................. 257/40 |
| 2013/0075704 | A1* | 3/2013 | Takasu et al. ................. 257/40 |

FOREIGN PATENT DOCUMENTS

| | | | |
|---|---|---|---|
| KR | 10-2011-0042004 | * | 4/2011 |
| WO | 03/058667 | A1 | 7/2003 |
| WO | 2004/043937 | A1 | 5/2004 |
| WO | 2007/090773 | A1 | 8/2007 |
| WO | 2008/031743 | A1 | 3/2008 |
| WO | 2009/100991 | A1 | 8/2009 |

OTHER PUBLICATIONS

European Search Report (EP Patent Application No. 11155124.8) dated Jun. 24, 2011, 7 pages.

* cited by examiner

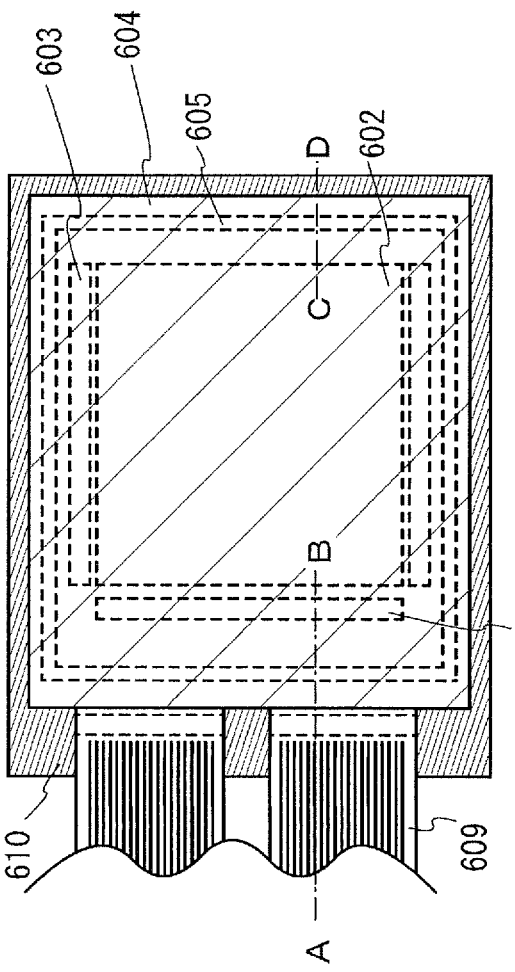
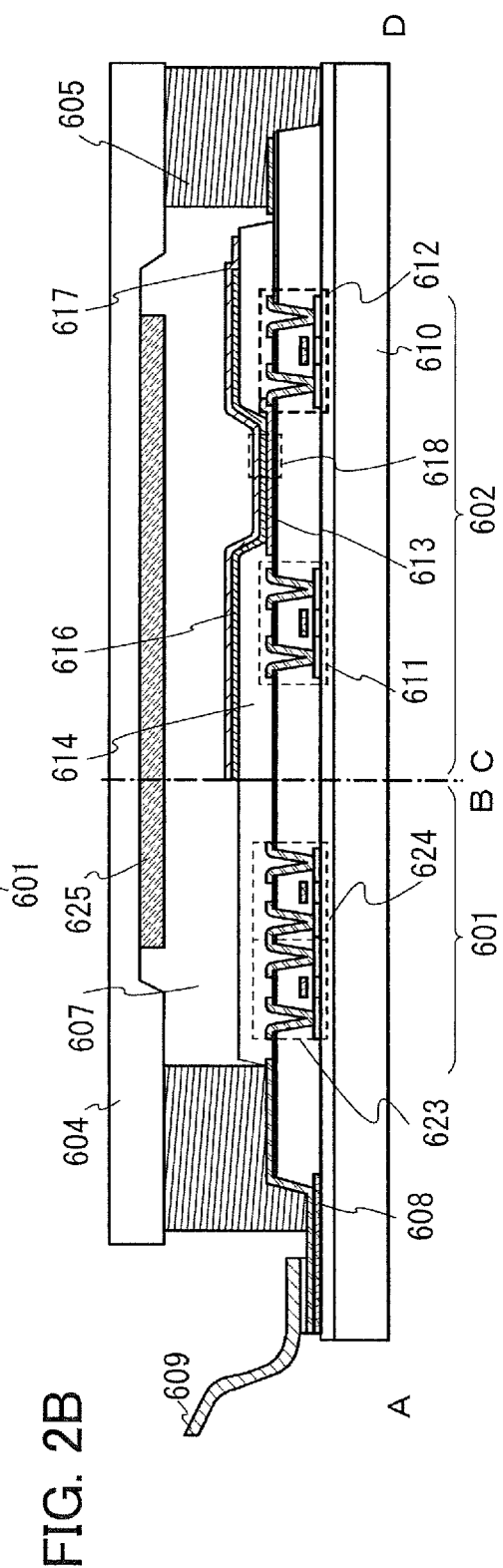
FIG. 2A
FIG. 2B

HETEROCYCLIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a heterocyclic compound, a light-emitting element, a light-emitting device, an electronic device, and a lighting device.

2. Description of the Related Art

As next generation lighting devices or display devices, display devices using light-emitting elements (organic EL elements) in which organic compounds are used as light-emitting substances have been developed at an accelerated pace because of their advantages of thinness, lightweightness, quick response to input signals, low power consumption, etc.

In an organic EL element, voltage application between electrodes, between which a light-emitting layer is interposed, causes recombination of electrons and holes injected from the electrodes. The recombination brings a light-emitting substance into an excited state, and the return from the excited state to the ground state is accompanied by light emission. Since the wavelength of light emitted from a light-emitting substance is peculiar to the light-emitting substance, use of different types of organic compounds as light-emitting substances makes it possible to obtain light-emitting elements which exhibit various wavelengths, i.e., various colors.

In the case of display devices which are expected to display images, such as displays, at least three-color light, i.e., red light, green light, and blue light is necessary for reproduction of full-color images.

Further, in application to lighting devices, light having wavelength components uniformly in the visible light region is ideal for obtaining a high color rendering property, but in reality, light obtained by mixing two or more kinds of light having different wavelengths is used for lighting application in many cases. It is known that, with a mixture of three-color light, i.e., red light, green light, and blue light, white light having a high color rendering property can be obtained.

Light emitted from a light-emitting substance is peculiar to the substance, as described above. However, important performances as a light-emitting element, such as lifetime, power consumption, and even emission efficiency, are not only dependent on a light-emitting substance but also greatly dependent on layers other than a light-emitting layer, an element structure, properties of an emission center substance and a host material, compatibility between them, carrier balance, and the like. Therefore, it is true that many kinds of light-emitting element materials are necessary for the growth of this field. For the above-described reasons, light-emitting element materials with a variety of molecular structures have been proposed.

As is generally known, the generation ratio of a singlet excited state to a triplet excited state in a light-emitting element using electroluminescence is 1:3. Therefore, a light-emitting element in which a phosphorescent material capable of converting the triplet excited state to light emission is used as an emission center substance can theoretically realize higher emission efficiency than a light-emitting element in which a fluorescent material capable of converting the singlet excited state to light emission is used as an emission center substance.

However, since the triplet excited state of a substance is at a lower energy level than the singlet excited state of the substance, a substance that emits phosphorescence has a larger band gap than a substance that emits fluorescence when the emissions are at the same wavelength.

As a substance serving as a host material in a host-guest type light-emitting layer or a substance contained in each transport layer in contact with a light-emitting layer, a substance having a larger band gap or higher triplet excitation energy (energy difference between a triplet excited state and a singlet ground state) than an emission center substance is used for efficient conversion of excitation energy to light emission from the emission center substance.

Therefore, a host material and a carrier-transport material each having an extremely large band gap are necessary in order to obtain fluorescence efficiently. There are however not many variations of materials that have a sufficiently large band gap in addition to good characteristics as a light-emitting element material, and as described above, the performance of a light-emitting element depends also on the compatibility between substances. In consideration of the above, it is difficult to say that there are sufficient variations of materials with which light-emitting elements having good characteristics can be manufactured.

Furthermore, since singlet excitation energy (an energy difference between a ground state and a singlet excited state) is higher than triplet excitation energy, a substance that has high triplet excitation energy also has high singlet excitation energy. Therefore, the above substance that has high triplet excitation energy is also effective in a light-emitting element using a fluorescent compound as a light-emitting substance.

Studies have been conducted on a compound having a dibenzo[f,h]quinoxaline ring, which are examples of the host material used when a phosphorescent compound is a guest material (e.g., see Patent Documents 1 and 2).

REFERENCE

Patent Document

[Patent Document 1]: PCT International Publication No. 03/058667

[Patent Document 2]: Japanese Published Patent Application No. 2007-189001

SUMMARY OF THE INVENTION

However, the above compound having a dibenzo[f,h]quinoxaline ring has a planar structure, and accordingly, the compound is easily crystallized. A light-emitting element including a compound that is easy to crystallize has a short lifetime. Further, in order that the compound having dibenzo[f,h]quinoxaline ring has a sterically bulky structure for the purpose of preventing the crystallization, another skeleton may be bonded to the dibenzo[f,h]quinoxaline ring; however, if the skeleton is directly bonded to the dibenzo[f,h]quinoxaline ring, the conjugated system could possibly extend to cause a decrease in triplet excitation energy. It is difficult to obtain high emission efficiency from a phosphorescent light-emitting element including a compound with small triplet excitation energy.

Furthermore, a quinoxaline skeleton is poor at accepting holes. When a compound that cannot easily accept holes is used as a host material of a light-emitting layer, the region of electron-hole recombination concentrates on an interface of the light-emitting layer, leading to a reduction in lifetime of the light-emitting element or a reduction in emission efficiency.

In view of the above, an object of one embodiment of the present invention is to provide a novel heterocyclic compound which can be used as a host material in which a light-emitting substance of a light-emitting layer in a light-emitting element is dispersed. In particular, the object is to provide a novel heterocyclic compound which can be suitably used as a host material in the case where the light-emitting element is a phosphorescent compound.

Further, in order to realize a light-emitting device, an electronic device, and a lighting device each having reduced power consumption and high reliability, a light-emitting element having low driving voltage, a light-emitting element having high current efficiency, or a light-emitting element having a long lifetime has been expected.

Another object of one embodiment of the present invention is to provide a light-emitting element having low driving voltage. Another object of one embodiment of the present invention is to provide a light-emitting element having high current efficiency. Another object of one embodiment of the present invention is to provide a light-emitting element having a long lifetime. Another object of one embodiment of the present invention is to provide a light-emitting device, an electronic device, and a lighting device each having reduced power consumption by using the above light-emitting element.

In the present invention, it is only necessary that at least one of the above-described objects should be achieved.

A compound having a quinoxaline skeleton has a high electron-transport property, and use of such a compound for a light-emitting element enables the element to have low driving voltage. On the other hand, a quinoxaline skeleton has a planar structure and is easily crystallized; therefore, there is a problem in that it is difficult to obtain a light-emitting element having a long lifetime by the use of the compound. Furthermore, a quinoxaline skeleton is poor at accepting holes. When a compound that cannot easily accept holes is used as a host material of a light-emitting layer, the region of electron-hole recombination concentrates on an interface of the light-emitting layer, leading to a more reduction in lifetime of the light-emitting element or a reduction in emission efficiency. These problems will be solved by introduction of a hole-transport skeleton into the molecule. However, if a hole-transport skeleton is directly bonded to a quinoxaline skeleton, the conjugated system extends to cause a decrease in band gap and a decrease in triplet excitation energy. It is difficult to efficiently obtain light emission at a short wavelength from a light-emitting element in which a compound with a small band gap or small triplet excitation energy is used as a host material.

Nevertheless, the present inventors have found that the above problems can be solved by using, for a light-emitting element, a compound comprising a dibenzo[f,h]quinoxaline ring and two hole-transport skeletons, where the dibenzo[f,h]quinoxaline ring and the two hole-transport skeletons are bonded to an aromatic hydrocarbon group.

Accordingly, one embodiment of the present invention is a light-emitting element including a compound comprising a dibenzo[f,h]quinoxaline ring and two hole-transport skeletons, where the dibenzo[f,h]quinoxaline ring and the two hole-transport skeletons are bonded to an aromatic hydrocarbon group.

A compound applied to one embodiment of the present invention has two hole-transport skeletons in addition to a dibenzo[f,h]quinoxaline ring, making it easy to accept holes. Accordingly, by the use of the compound as a host material in a light-emitting layer, electrons and holes recombine in the light-emitting layer, so that it is possible to suppress the decrease in the lifetime of the light-emitting element. Furthermore, the introduction of two hole-transport skeletons enables the compound to have a sterically bulky structure, and the compound is difficult to crystallize when formed into a film. By the use of the compound for a light-emitting element, the element can have a long lifetime. Moreover, in this compound, since a dibenzo[f,h]quinoxaline ring and a hole-transport skeleton are bonded through an aromatic hydrocarbon skeleton, decreases in band gap and triplet excitation energy can be prevented as compared with a compound in which a dibenzo[f,h]quinoxaline ring and hole-transport skeletons are directly bonded. By the use of the compound for a light-emitting element, the element can have high current efficiency.

Thus, the compound described above can be suitably used as a material for an organic device such as a light-emitting element or an organic transistor.

The aromatic hydrocarbon group to which two hole-transport skeletons are bonded is preferably bonded to the 2-position of the dibenzo[f,h]quinoxaline ring.

As the hole-transport skeleton, a π-electron rich heteroaromatic ring is preferable. As the π-electron rich heteroaromatic ring, a carbazole ring, a dibenzofuran ring, or a dibenzothiophene ring is preferable.

As the aromatic hydrocarbon group, a substituted or unsubstituted phenyl group is preferable.

Since a light-emitting element of one embodiment of the present invention which is obtained as above has low driving voltage, high current efficiency, and a long lifetime, a light-emitting device (such as an image display device) using this light-emitting element can have reduced power consumption. Thus, one embodiment of the present invention is a light-emitting device including any of the above light-emitting elements. One embodiment of the present invention also includes an electronic device using the light-emitting device in its display portion and a lighting device using the light-emitting device in its light-emitting portion.

Note that the light-emitting device in this specification includes an image display device using a light-emitting element. Further, the category of the light-emitting device in this specification includes a module in which a light-emitting element is provided with a connector such as an anisotropic conductive film, TAB (tape automated bonding) tape, or a TCP (tape carrier package); a module in which the top of the TAB tape or the TCP is provided with a printed wiring board; and a module in which an IC (integrated circuit) is directly mounted on a light-emitting element by a COG (chip on glass) method. Furthermore, the category includes light-emitting devices that are used in lighting equipment.

As examples of the compound comprising a dibenzo[f,h]quinoxaline ring and two hole-transport skeletons, where the dibenzo[f,h]quinoxaline ring and the two hole-transport skeletons are bonded to an aromatic hydrocarbon group, a heterocyclic compounds are given below.

One embodiment of the present invention is a heterocyclic compound represented by the following general formula (G1).

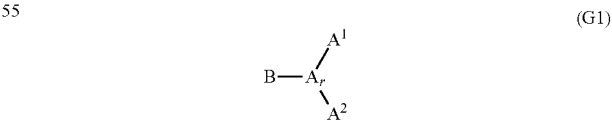

(G1)

In the general formula (G1), $A^1$ and $A^2$ each independently represent any of a substituted or unsubstituted carbazolyl group, a substituted or unsubstituted dibenzofuranyl group, and a substituted or unsubstituted dibenzothiophenyl group; B represents a substituted or unsubstituted dibenzo[f,h]quinoxalinyl group; Ar represents an aromatic hydrocarbon group having 6 to 13 carbon atoms; the aromatic hydrocarbon group may have a substituent; and substituents of the aromatic hydrocarbon group may be bonded to each other to form a ring.

Another embodiment of the present invention is a heterocyclic compound represented by the following general formula (G2).

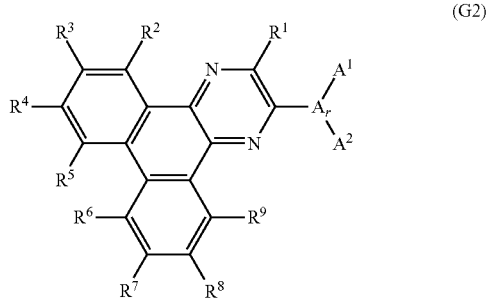

(G2)

In the general formula (G2), $A^1$ and $A^2$ each independently represent any of a substituted or unsubstituted carbazolyl group, a substituted or unsubstituted dibenzofuranyl group, and a substituted or unsubstituted dibenzothiophenyl group; Ar represents an aromatic hydrocarbon group having 6 to 13 carbon atoms; the aromatic hydrocarbon group may have a substituent; substituents of the aromatic hydrocarbon group may be bonded to each other to form a ring; and $R^1$ to $R^9$ each independently represent any of hydrogen, an alkyl group having 1 to 4 carbon atoms, and a substituted or unsubstituted aryl group having 6 to 13 carbon atoms.

Another embodiment of the present invention is a heterocyclic compound represented by the following general formula (G3-1).

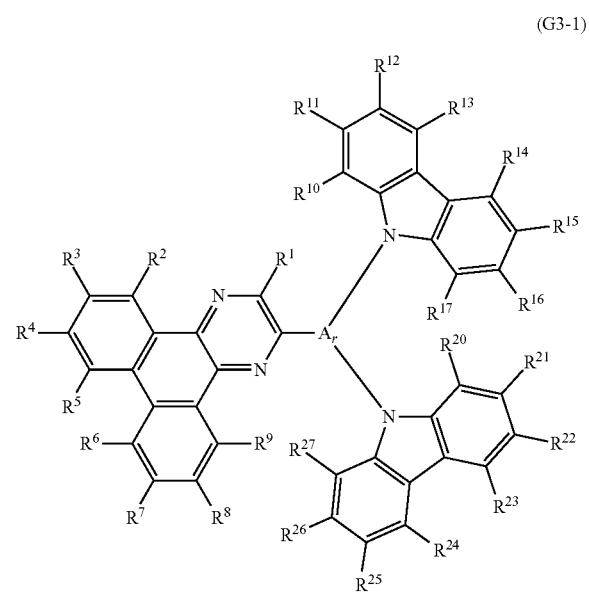

(G3-1)

In the general formula (G3-1), Ar represents an aromatic hydrocarbon group having 6 to 13 carbon atoms; the aromatic hydrocarbon group may have a substituent; substituents of the aromatic hydrocarbon group may be bonded to each other to form a ring; and $R^1$ to $R^9$, $R^{10}$ to $R^{17}$, and $R^{20}$ to $R^{27}$ each independently represent any of hydrogen, an alkyl group having 1 to 4 carbon atoms, and a substituted or unsubstituted aryl group having 6 to 13 carbon atoms.

Another embodiment of the present invention is a heterocyclic compound represented by the following general formula (G3-2).

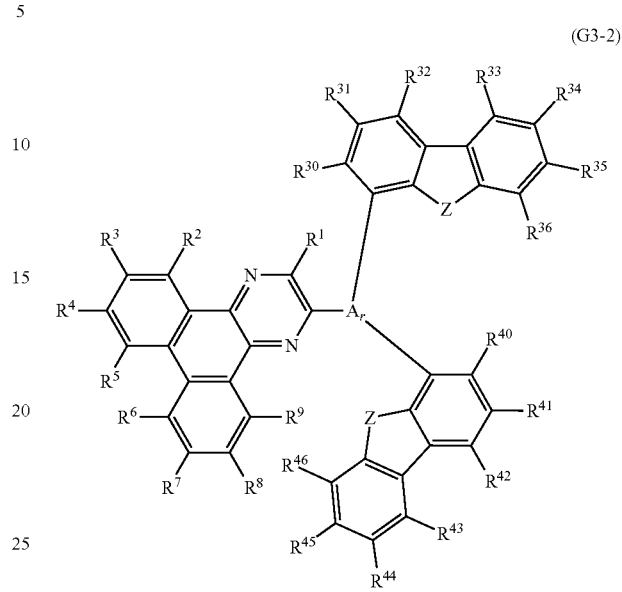

(G3-2)

In the general formula (G3-2), Ar represents an aromatic hydrocarbon group having 6 to 13 carbon atoms; the aromatic hydrocarbon group may have a substituent; substituents of the aromatic hydrocarbon group may be bonded to each other to form a ring; $R^1$ to $R^9$, $R^{30}$ to $R^{36}$, and $R^{40}$ to $R^{46}$ each independently represent any of hydrogen, an alkyl group having 1 to 4 carbon atoms, and a substituted or unsubstituted aryl group having 6 to 13 carbon atoms; and Z represents oxygen or sulfur.

In the general formulae (G3-1) and (G3-2), Ar is preferably either a substituted or unsubstituted benzenetriyl group or a substituted or unsubstituted biphenyltriyl group. In particular, Ar is preferably a substituted or unsubstituted benzenetriyl group.

Another embodiment of the present invention is a heterocyclic compound represented by the following general formula (G4-1).

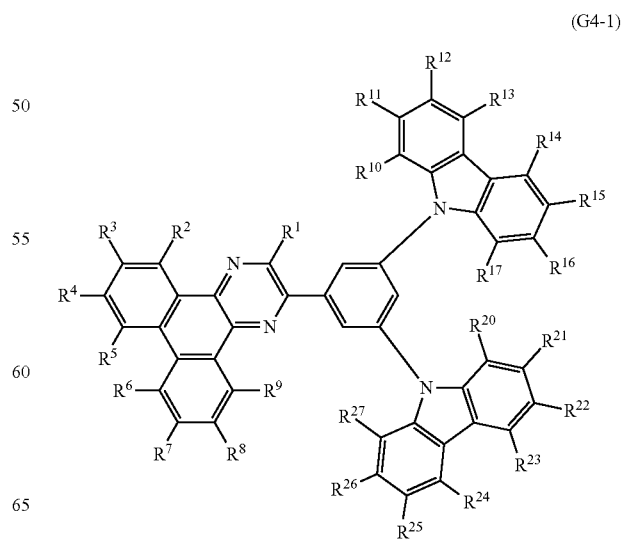

(G4-1)

In the general formula (G4-1), $R^1$ to $R^9$, $R^{10}$ to $R^{17}$, and $R^{20}$ to $R^{27}$ each independently represent any of hydrogen, an alkyl group having 1 to 4 carbon atoms, and a substituted or unsubstituted aryl group having 6 to 13 carbon atoms.

Another embodiment of the present invention is a heterocyclic compound represented by the following general formula (G4-2).

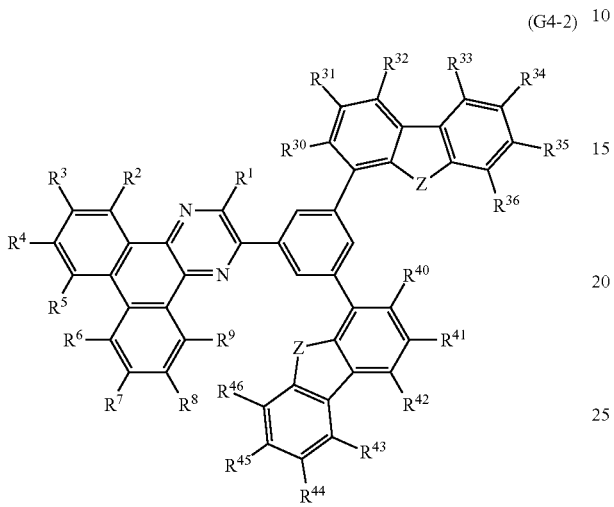

(G4-2)

In the general formula (G4-2), $R^1$ to $R^9$, $R^{30}$ to $R^{36}$, and $R^{40}$ to $R^{46}$ each independently represent any of hydrogen, an alkyl group having 1 to 4 carbon atoms, and a substituted or unsubstituted aryl group having 6 to 13 carbon atoms; and Z represents oxygen or sulfur.

Another embodiment of the present invention is a heterocyclic compound represented by the following general formula (G5-1).

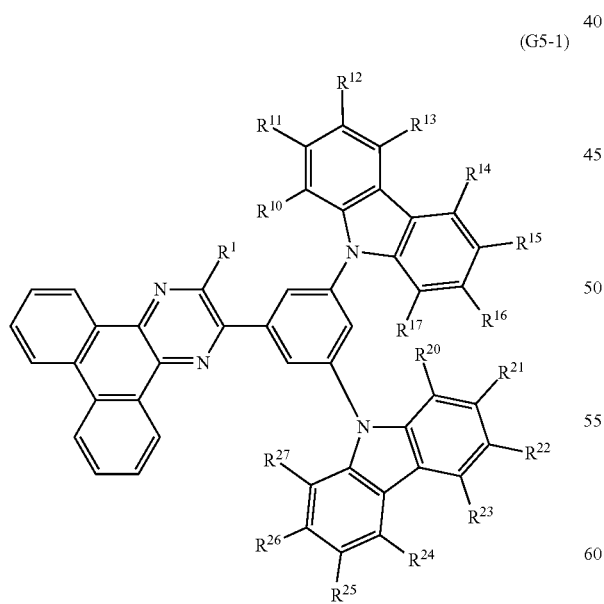

(G5-1)

In the general formula (G5-1), $R^1$, $R^{10}$ to $R^{17}$, and $R^{20}$ to $R^{27}$ each independently represent any of hydrogen, an alkyl group having 1 to 4 carbon atoms, and a substituted or unsubstituted aryl group having 6 to 13 carbon atoms.

Another embodiment of the present invention is a heterocyclic compound represented by the following general formula (G5-2).

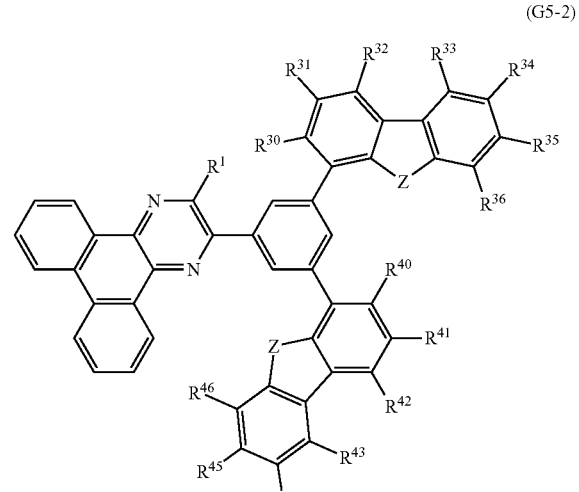

(G5-2)

In the general formula (G5-2), $R^1$, $R^{30}$ to $R^{36}$, and $R^{40}$ to $R^{46}$ each independently represent any of hydrogen, an alkyl group having 1 to 4 carbon atoms, and a substituted or unsubstituted aryl group having 6 to 13 carbon atoms; and Z represents oxygen or sulfur.

Another embodiment of the present invention is a heterocyclic compound represented by the following general formula (G6).

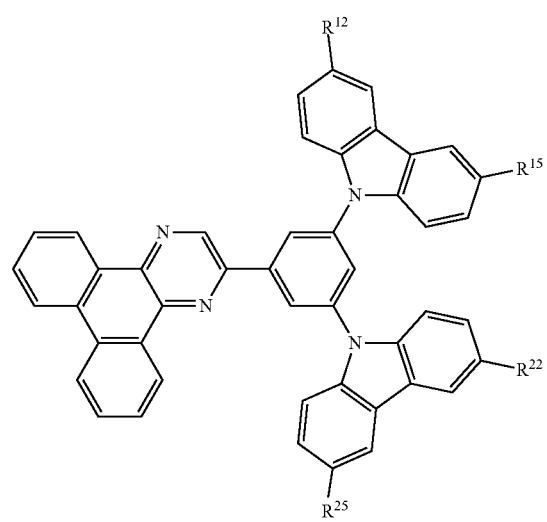

(G6)

In the general formula (G6), $R^{12}$, $R^{15}$, $R^{22}$, and $R^{25}$ each independently represent any of hydrogen, an alkyl group having 1 to 4 carbon atoms, and a substituted or unsubstituted aryl group having 6 to 13 carbon atoms.

Another embodiment of the present invention is a heterocyclic compound represented by the following structural formula (100).

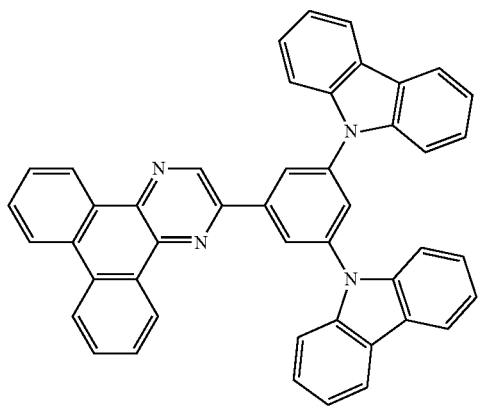
(100)

The heterocyclic compound can be expressed as a compound comprising a dibenzo[f,h]quinoxaline ring and two hole-transport skeletons, where the dibenzo[f,h]quinoxaline ring and the two hole-transport skeletons are bonded to an aromatic hydrocarbon group; therefore, one embodiment of the present invention includes a light-emitting element including the heterocyclic compound. One embodiment of the present invention also includes a light-emitting device, an electronic device, and a lighting device each including the light-emitting element.

One embodiment of the present invention is a novel heterocyclic compound which can be suitably used as a host material in which a light-emitting substance of a light-emitting layer in a light-emitting element is dispersed. One embodiment of the present invention enables to provide a light-emitting element having low driving voltage. One embodiment of the present invention enables to provide a light-emitting element having high current efficiency. One embodiment of the present invention enables to provide a light-emitting element having a long lifetime. One embodiment of the present invention enables to provide a light-emitting device, an electronic device, and a lighting device each having reduced power consumption.

BRIEF DESCRIPTION OF THE DRAWINGS

In the accompanying drawings:
FIGS. 2A and 2B illustrate a light-emitting device according to one embodiment of the present invention;
FIGS. 4A to 4D each illustrate an electronic device according to one embodiment of the present invention.

DETAILED DESCRIPTION OF THE INVENTION

Figure 1A:
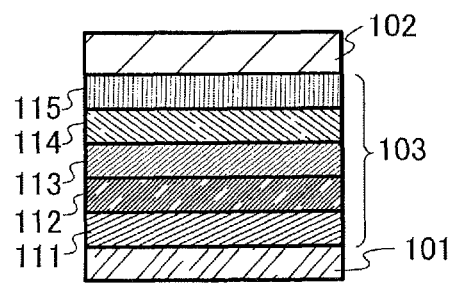
FIGS. 1A and 1B each illustrate a light emitting element according to one embodiment of the present invention.

Hereinafter, embodiments and examples of the present invention will be described with reference to the drawings. Note that the invention is not limited to the following description, and it is easily understood by those skilled in the art that various changes and modifications can be made without departing from the spirit and scope of the invention. Therefore, the present invention should not be construed as being limited to the description in the following embodiments and examples.

Embodiment 1

In this embodiment, a heterocyclic compound of one embodiment of the present invention is described. One embodiment of the present invention is a heterocyclic compound represented by the following general formula (G1).

(G1)

In the general formula (G1), $A^1$ and $A^2$ each independently represent any of a substituted or unsubstituted carbazolyl group, a substituted or unsubstituted dibenzofuranyl group, and a substituted or unsubstituted dibenzothiophenyl group; B represents a substituted or unsubstituted dibenzo[f,h]quinoxalinyl group; Ar represents an aromatic hydrocarbon group having 6 to 13 carbon atoms; the aromatic hydrocarbon group may have a substituent; and substituents of the aromatic hydrocarbon group may be bonded to each other to form a ring.

Another embodiment of the present invention is a heterocyclic compound represented by the following general formula (G2).

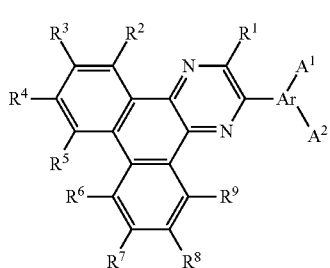

(G2)

In the general formula (G2), $A^1$ and $A^2$ each independently represent any of a substituted or unsubstituted carbazolyl group, a substituted or unsubstituted dibenzofuranyl group, and a substituted or unsubstituted dibenzothiophenyl group; Ar represents an aromatic hydrocarbon group having 6 to 13 carbon atoms; the aromatic hydrocarbon group may have a substituent; substituents of the aromatic hydrocarbon group may be bonded to each other to form a ring; and $R^1$ to $R^9$ each independently represent any of hydrogen, an alkyl group having 1 to 4 carbon atoms, and a substituted or unsubstituted aryl group having 6 to 13 carbon atoms.

Another embodiment of the present invention is a heterocyclic compound represented by the following general formula (G3-1).

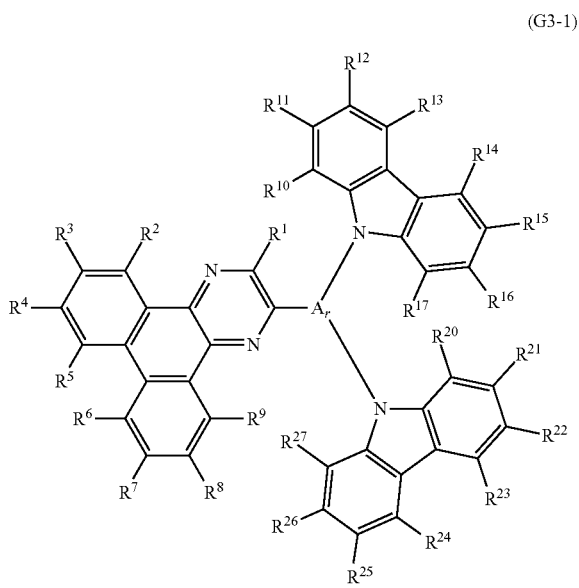

(G3-1)

In the general formula (G3-1), Ar represents an aromatic hydrocarbon group having 6 to 13 carbon atoms; the aromatic hydrocarbon group may have a substituent; substituents of the aromatic hydrocarbon group may be bonded to each other to form a ring; and $R^1$ to $R^9$, $R^{10}$ to $R^{17}$, and $R^{20}$ to $R^{27}$ each independently represent any of hydrogen, an alkyl group having 1 to 4 carbon atoms, and a substituted or unsubstituted aryl group having 6 to 13 carbon atoms.

Another embodiment of the present invention is a heterocyclic compound represented by the following general formula (G3-2).

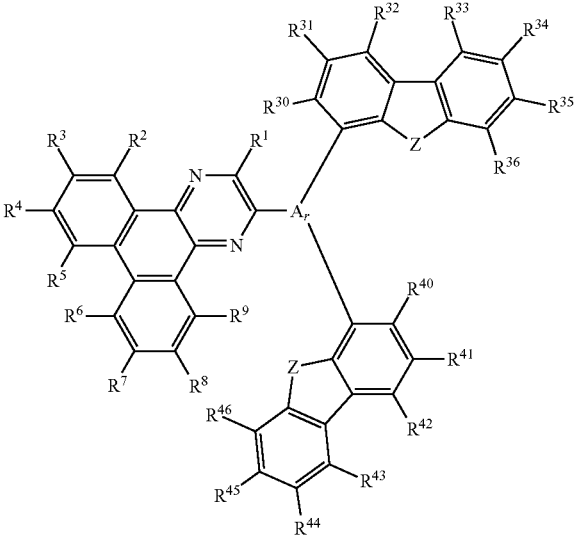

(G3-2)

In the general formula (G3-2), Ar represents an aromatic hydrocarbon group having 6 to 13 carbon atoms; the aromatic hydrocarbon group may have a substituent; substituents of the aromatic hydrocarbon group may be bonded to each other to form a ring; $R^1$ to $R^9$, $R^{30}$ to $R^{36}$, and $R^{40}$ to $R^{46}$ each independently represent any of hydrogen, an alkyl group having 1 to 4 carbon atoms, and a substituted or unsubstituted aryl group having 6 to 13 carbon atoms; and Z represents oxygen or sulfur.

In the general formulae (G3-1) and (G3-2), Ar is preferably either a substituted or unsubstituted benzenetriyl group or a substituted or unsubstituted biphenyltriyl group. In particular, Ar is preferably a substituted or unsubstituted benzenetriyl group. Furthermore, Ar is preferably a 1,3,5-benzenetriyl group.

Another embodiment of the present invention is a heterocyclic compound represented by the following general formula (G4-1).

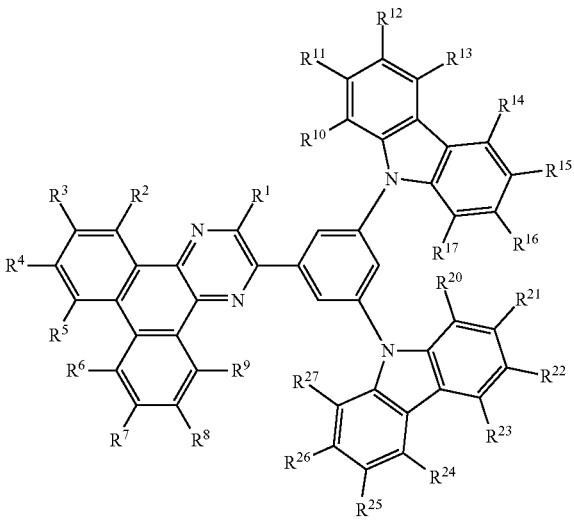

(G4-1)

In the general formula (G4-1), $R^1$ to $R^9$, $R^{10}$ to $R^{17}$, and $R^{20}$ to $R^{27}$ each independently represent any of hydrogen, an alkyl group having 1 to 4 carbon atoms, and a substituted or unsubstituted aryl group having 6 to 13 carbon atoms.

Another embodiment of the present invention is a heterocyclic compound represented by the following general formula (G4-2).

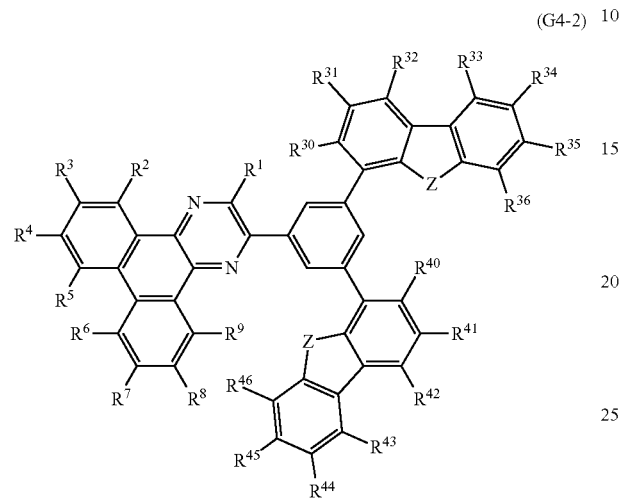

(G4-2)

In the general formula (G4-2), $R^1$ to $R^9$, $R^{30}$ to $R^{36}$, and $R^{40}$ to $R^{46}$ each independently represent any of hydrogen, an alkyl group having 1 to 4 carbon atoms, and a substituted or unsubstituted aryl group having 6 to 13 carbon atoms; and Z represents oxygen or sulfur.

Another embodiment of the present invention is a heterocyclic compound represented by the following general formula (G5-1).

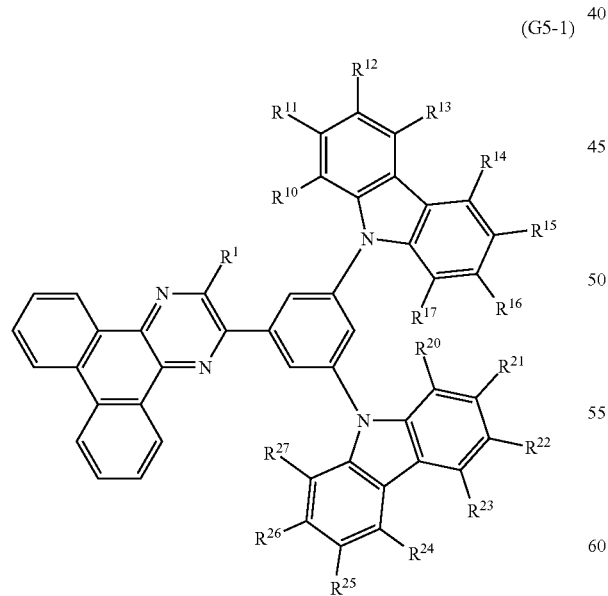

(G5-1)

In the general formula (G5-1), $R^1$, $R^{10}$ to $R^{17}$, and $R^{20}$ to $R^{27}$ each independently represent any of hydrogen, an alkyl group having 1 to 4 carbon atoms, and a substituted or unsubstituted aryl group having 6 to 13 carbon atoms.

Another embodiment of the present invention is a heterocyclic compound represented by the following general formula (G5-2).

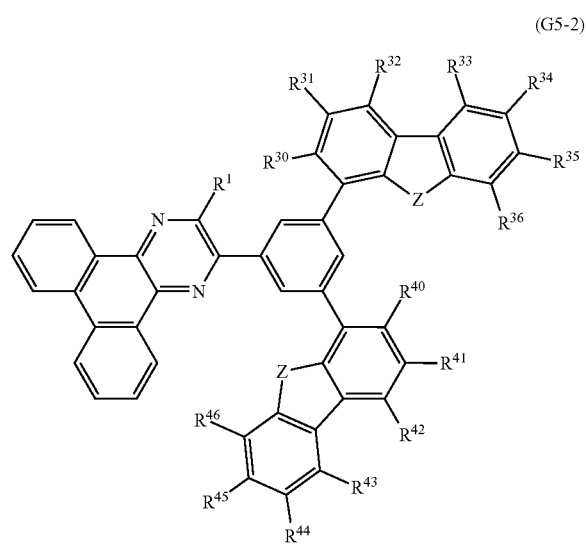

(G5-2)

In the general formula (G5-2), $R^1$, $R^{30}$ to $R^{36}$, and $R^{40}$ to $R^{46}$ each independently represent any of hydrogen, an alkyl group having 1 to 4 carbon atoms, and a substituted or unsubstituted aryl group having 6 to 13 carbon atoms; and Z represents oxygen or sulfur.

Another embodiment of the present invention is a heterocyclic compound represented by the following general formula (G6).

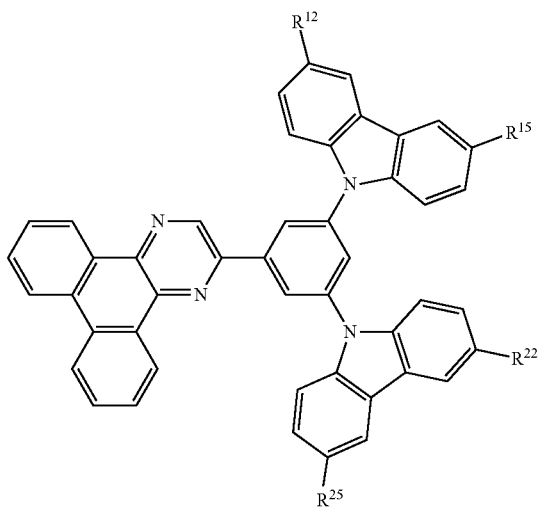

(G6)

In the general formula (G6), $R^{12}$, $R^{15}$, $R^{22}$, and $R^{25}$ each independently represent any of hydrogen, an alkyl group having 1 to 4 carbon atoms, and a substituted or unsubstituted aryl group having 6 to 13 carbon atoms.

The heterocyclic compound can be expressed as a compound comprising a dibenzo[f,h]quinoxaline ring and two hole-transport skeletons, where the dibenzo[f,h]quinoxaline ring and the two hole-transport skeletons are bonded to an aromatic hydrocarbon group; therefore, one embodiment of the present invention includes a light-emitting element including the heterocyclic compound. One embodiment of the present invention also includes a light-emitting device, an electronic device, and a lighting device each including the light-emitting element.

As specific structures of Ar in the general formulae (G1), (G2), (G3-1), and (G3-2), for example, substituents shown in the following structural formulae (1-1) to (1-6) are given.

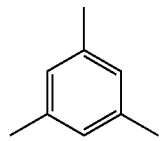
(1-1)

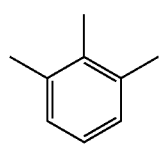
(1-2)

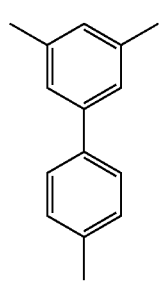
(1-3)

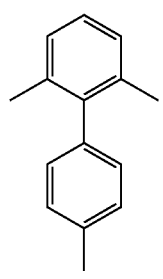
(1-4)

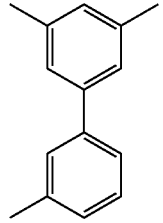
(1-5)

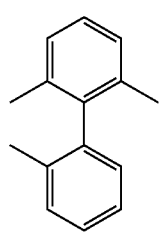
(1-6)

As specific structures of $R^1$ to $R^9$, $R^{10}$ to $R^{17}$, $R^{20}$ to $R^{27}$, $R^{30}$ to $R^{36}$, and $R^{40}$ to $R^{46}$ in the general formulae (G1), (G2), (G3-1), (G3-2), (G4-1), (G4-2), (G5-1), (G5-2), and (G6), for example, substituents shown in the following structural formulae (2-1) to (2-23) are given.

(2-1)

(2-2)

(2-3)

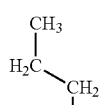
(2-4)

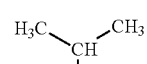
(2-5)

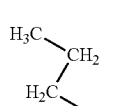
(2-6)

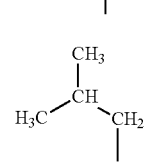
(2-7)

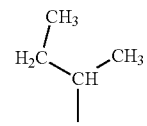
(2-8)

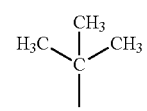
(2-9)

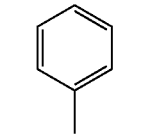
(2-10)

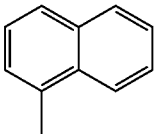
(2-11)

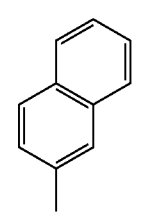
(2-12)

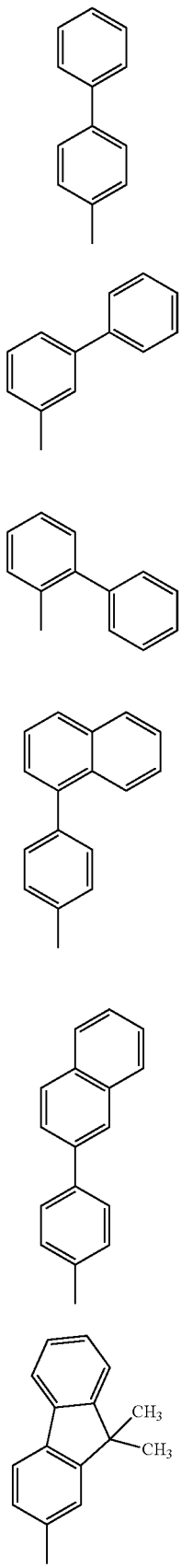
(2-13)
(2-14)
(2-15)
(2-16)
(2-17)
(2-18)
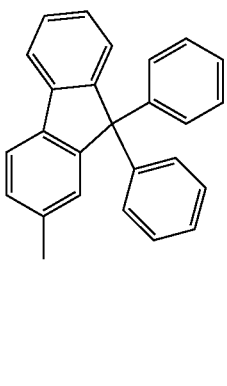
(2-19)
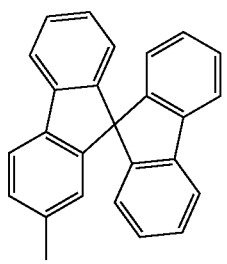
(2-20)
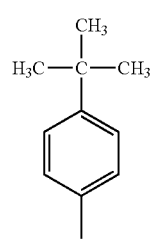
(2-21)
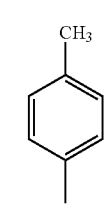
(2-22)
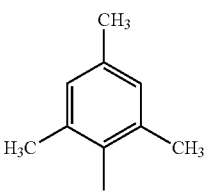
(2-23)
Specific examples of the heterocyclic compound represented by the general formula (G1) include heterocyclic compounds represented by the structural formulae (100) to (155), (200) to (253), and (300) to (353). Note that the present invention is not limited thereto.

(100)
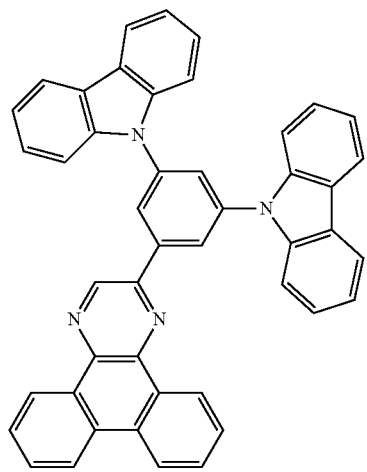
(101)
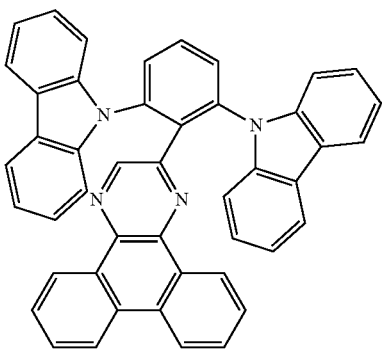
(102)
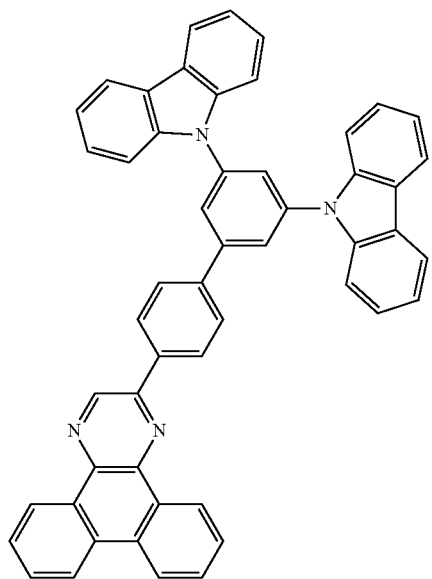
(103)
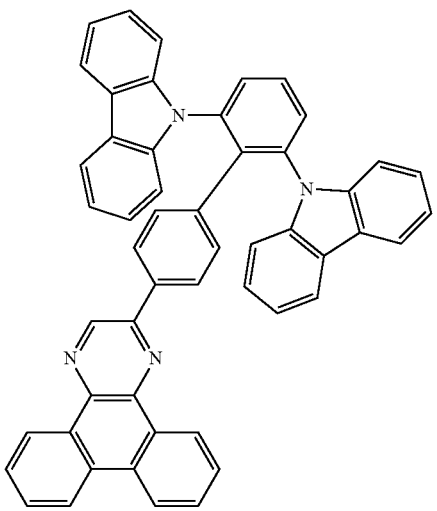
(104)
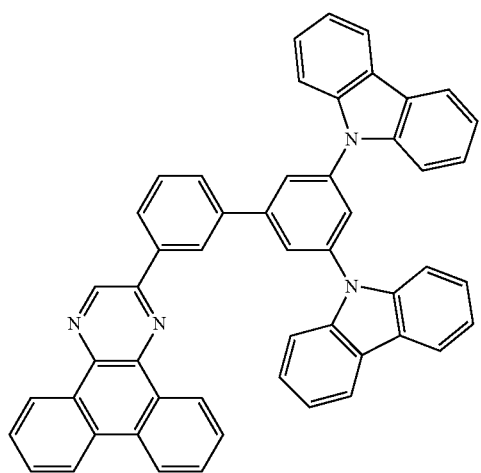
(105)
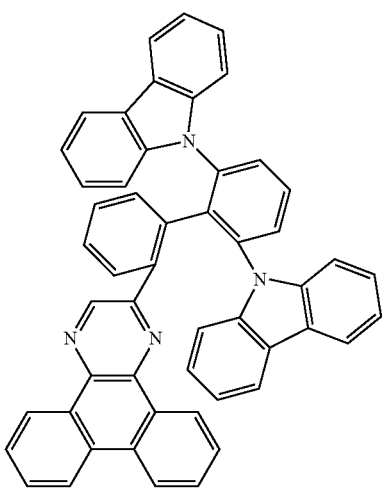

-continued
(107)
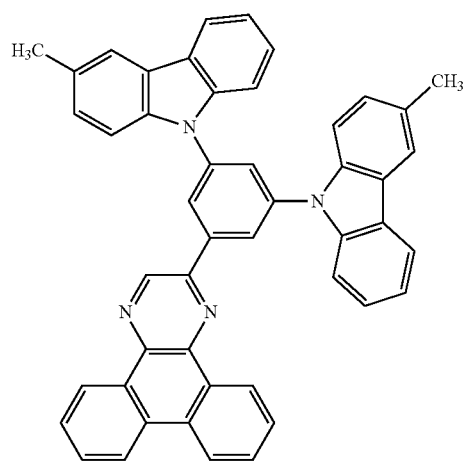
(106)
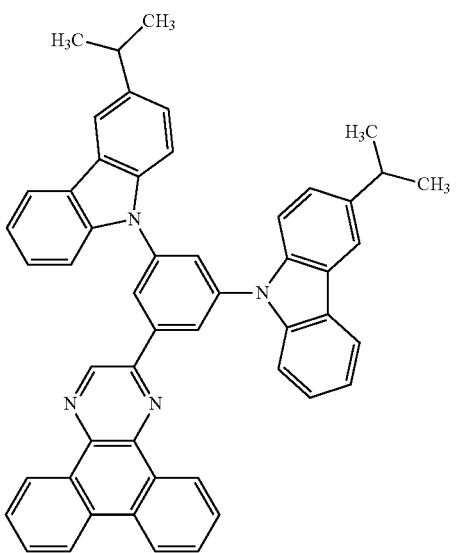
(108)
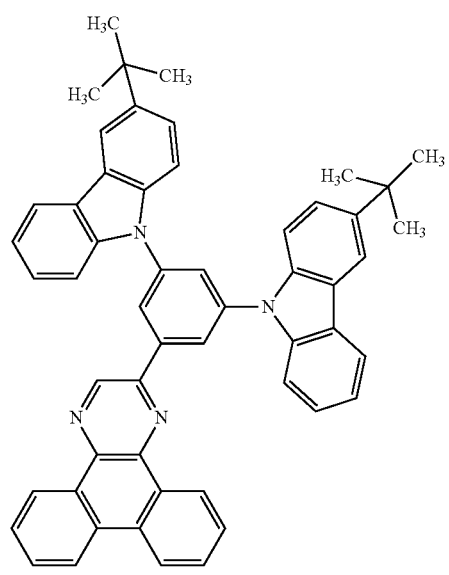
(109)
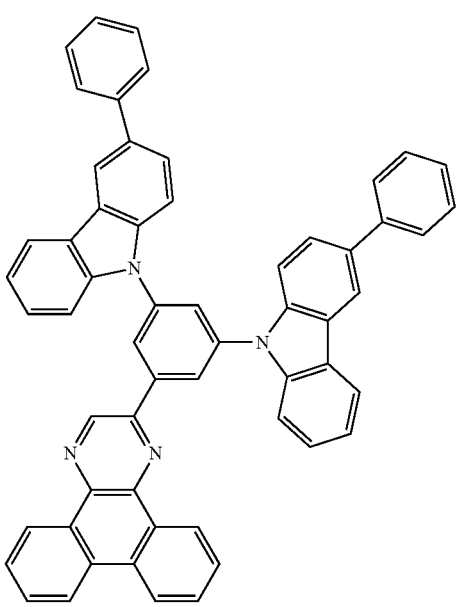

-continued
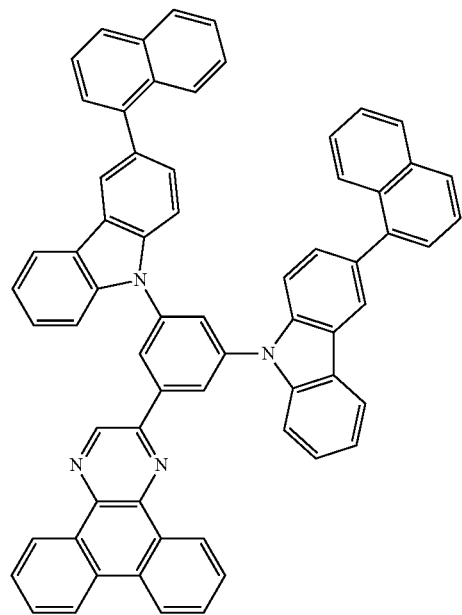
(110)
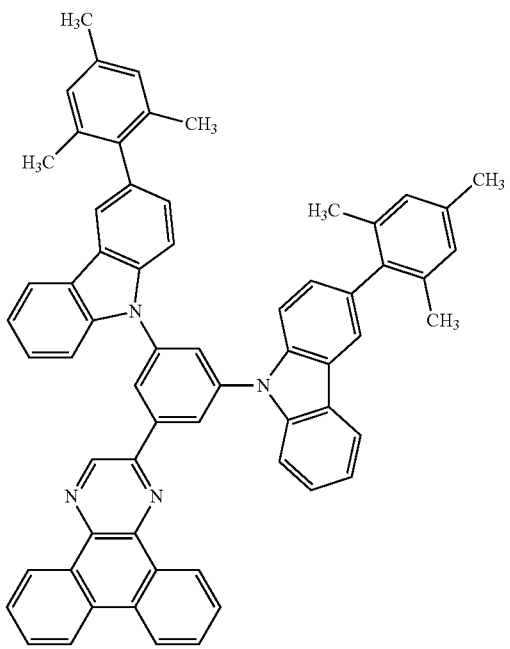
(111)
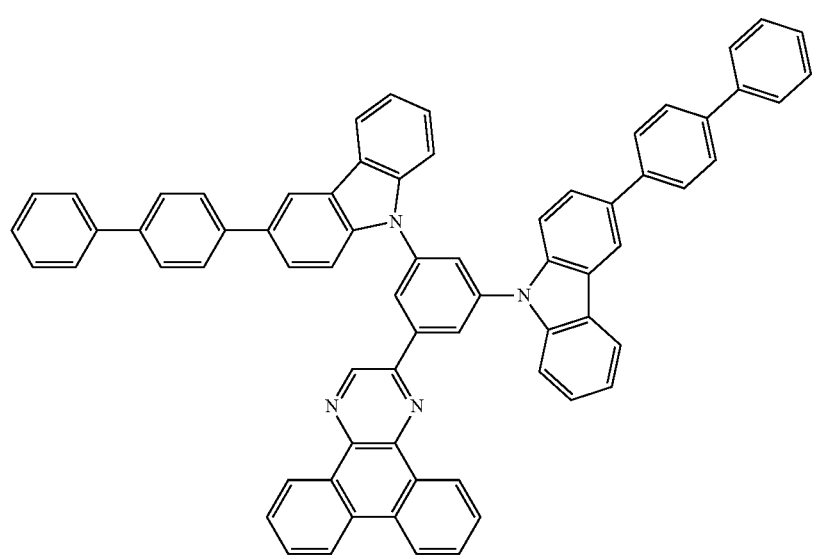
(112)

-continued
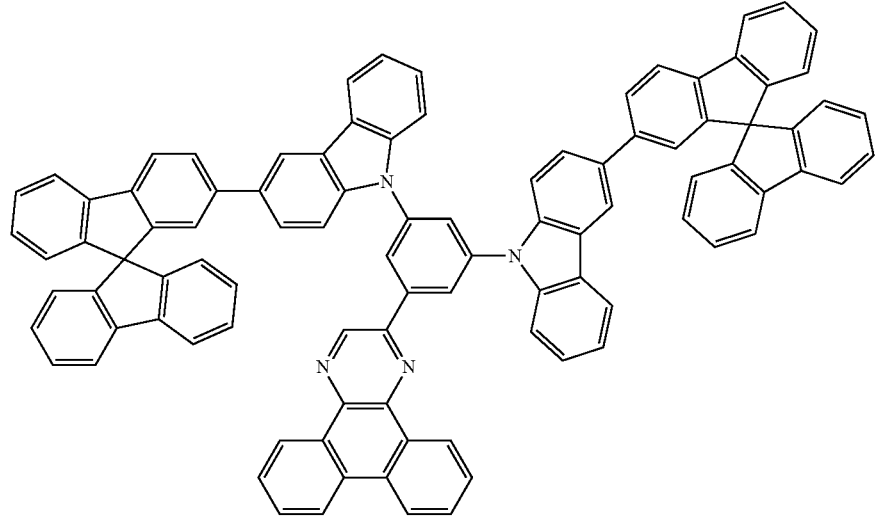
(113)
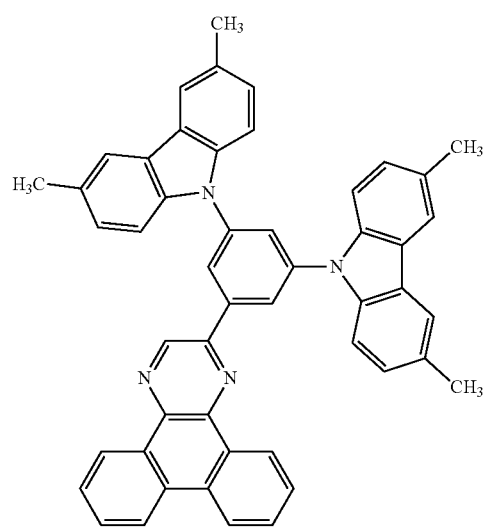
(114)
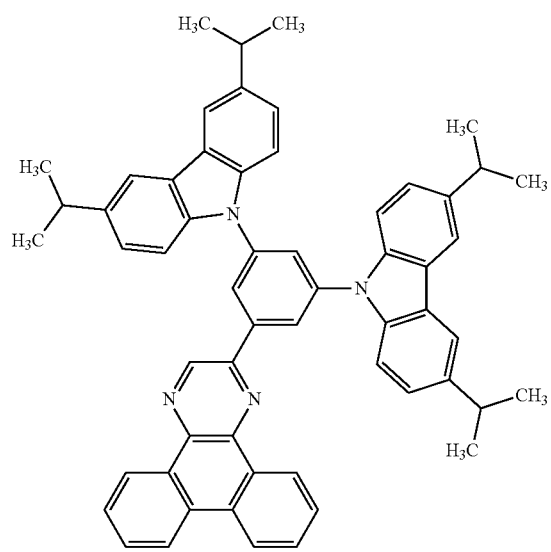
(115)

(116)
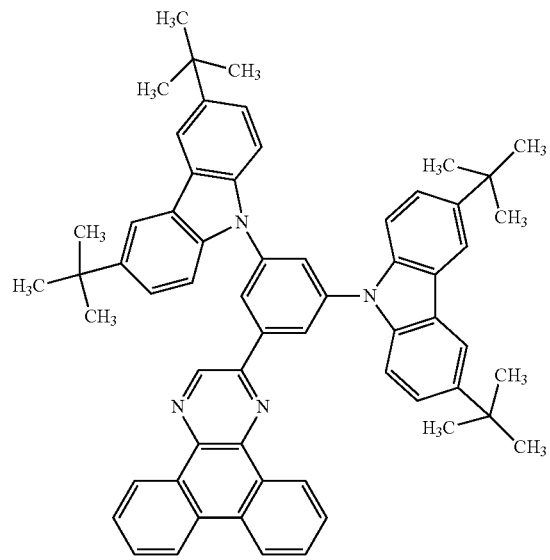
(117)
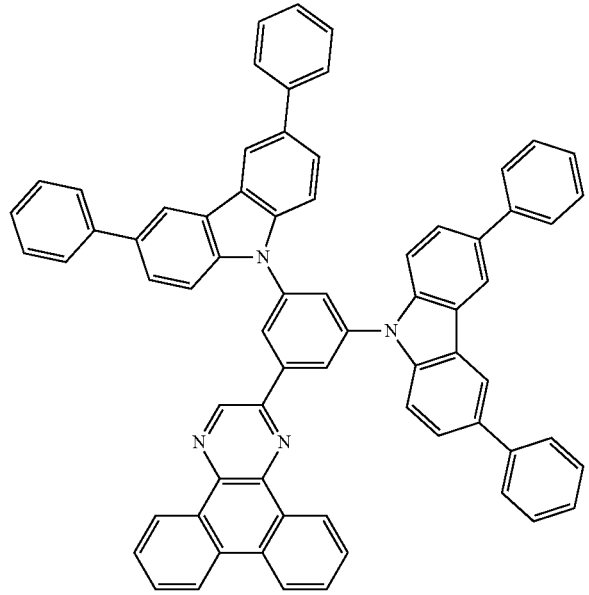
(118)
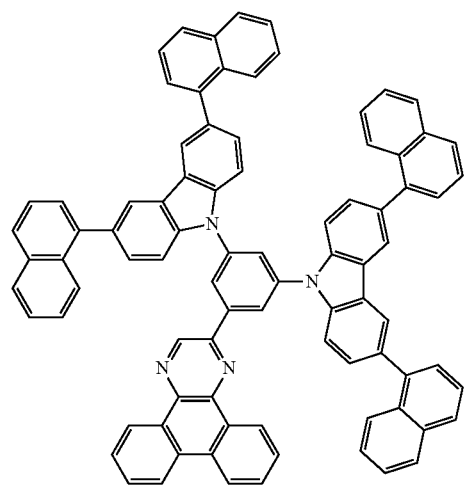
(119)
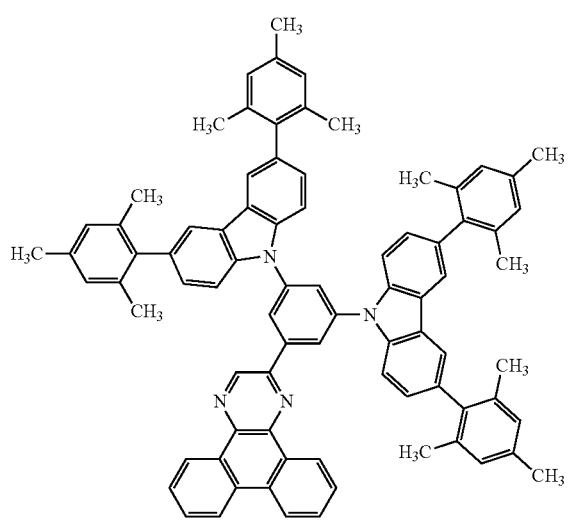

-continued
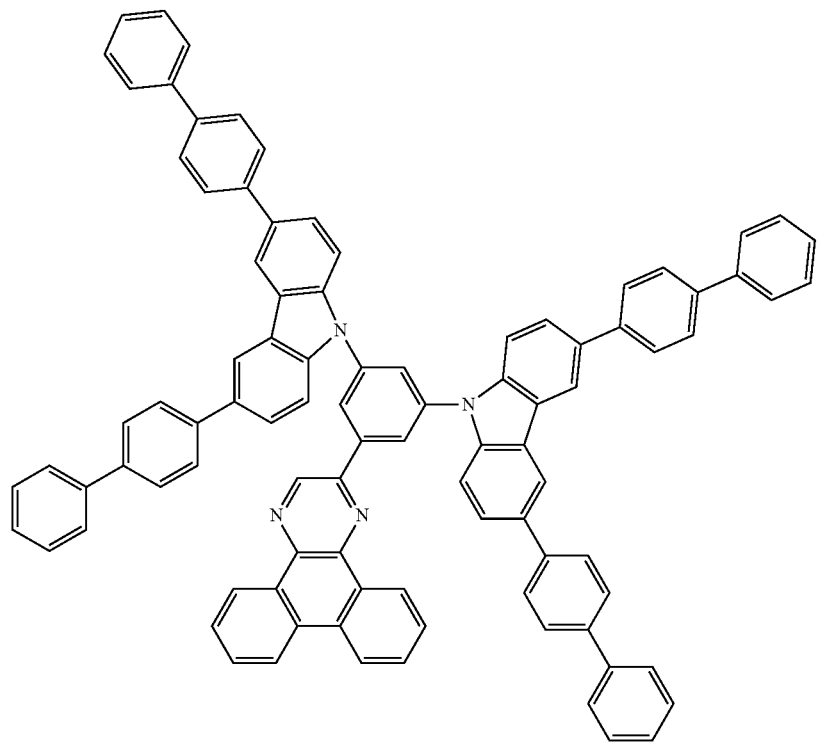
(120)
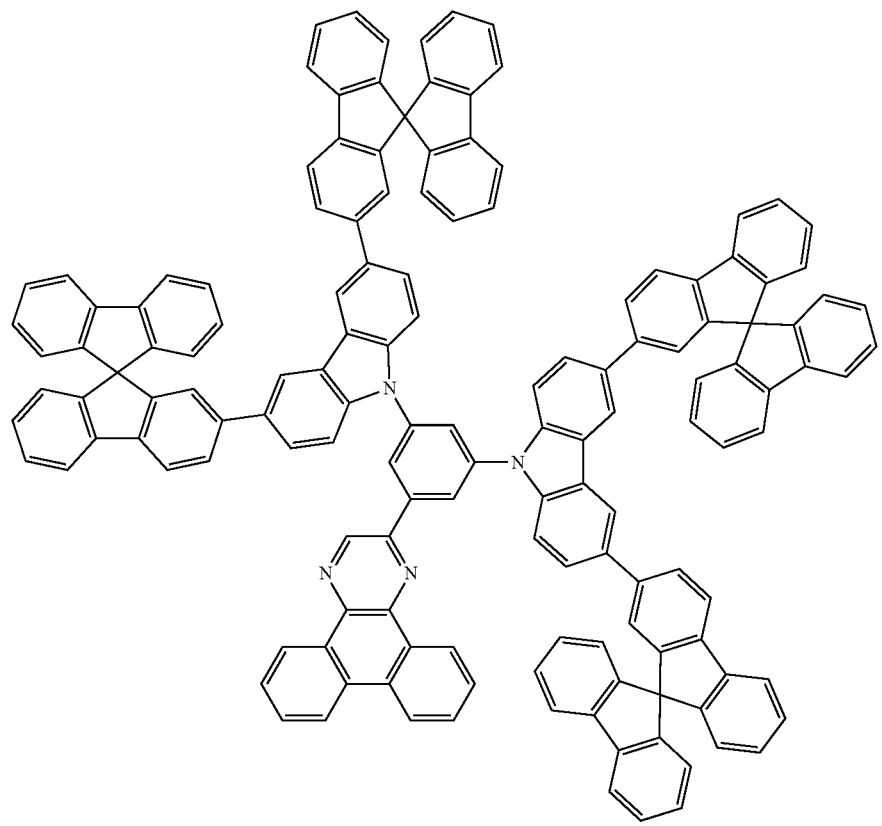
(121)

-continued
(122)
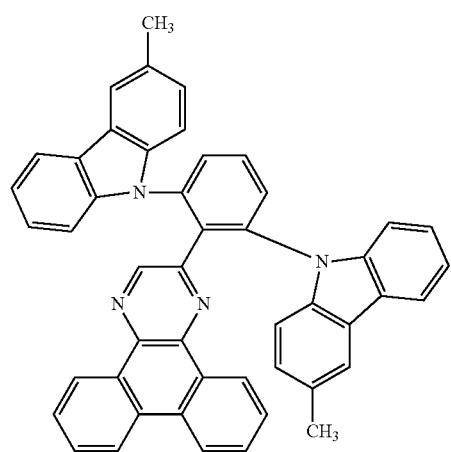
(123)
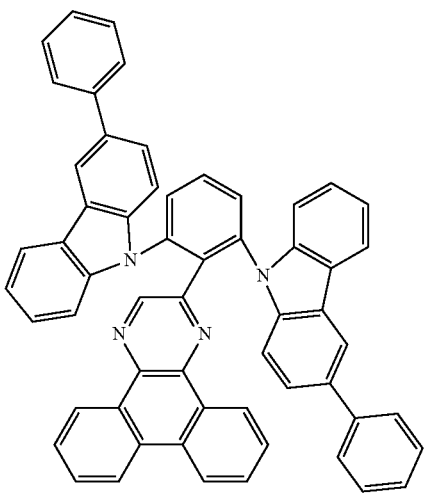
(124)
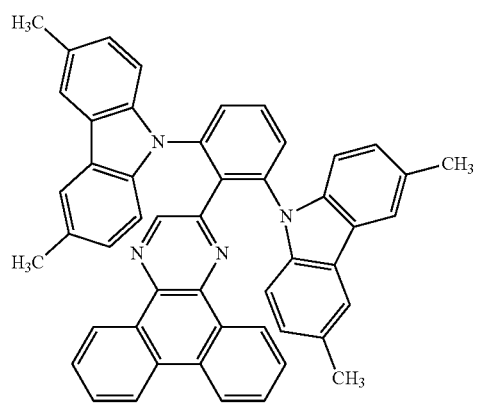
(125)
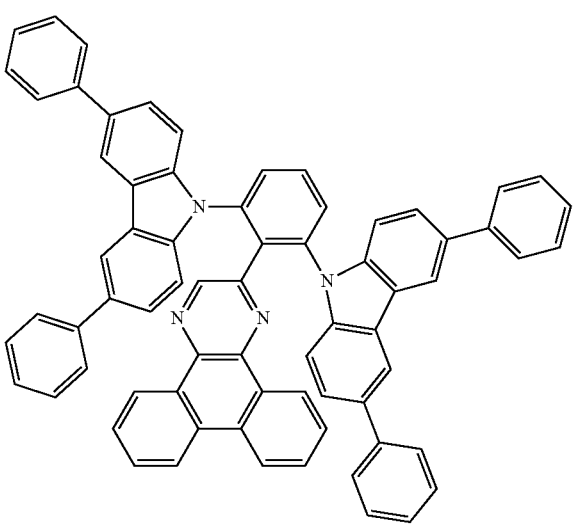
(126)
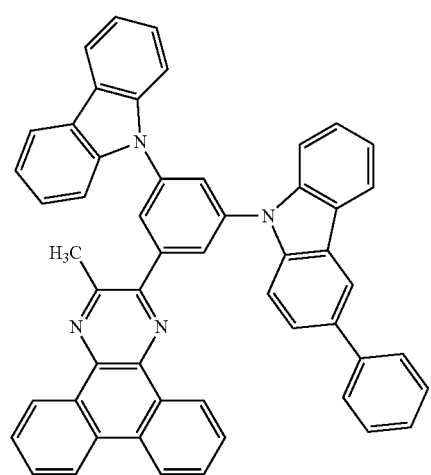
(127)
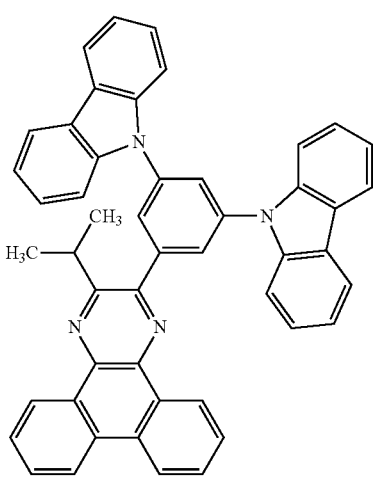

-continued
(128)
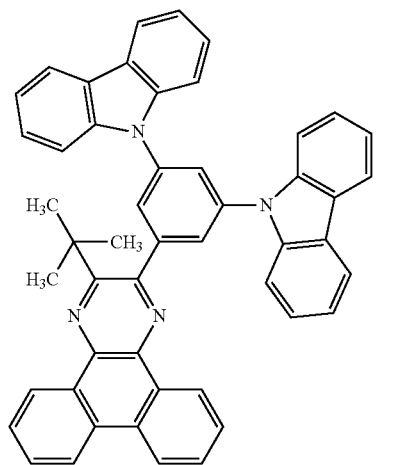
(129)
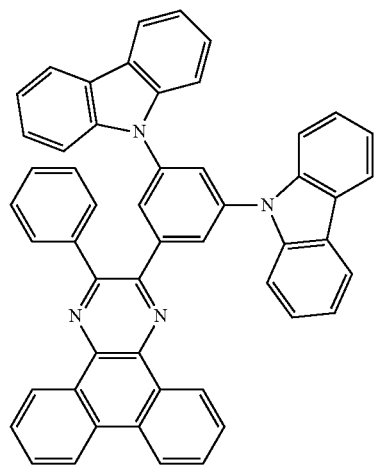
(130)
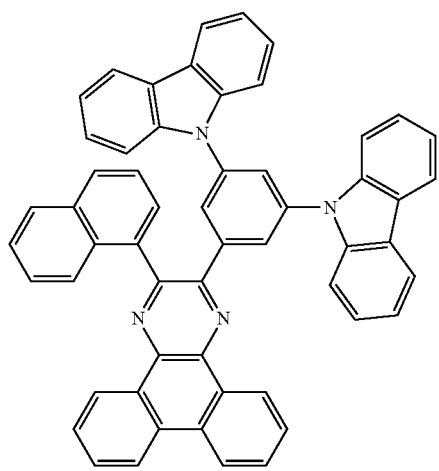
(131)
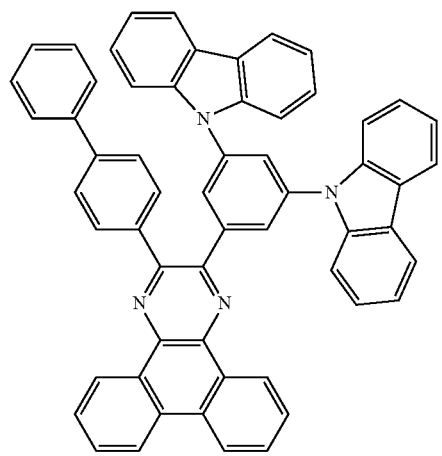
(132)
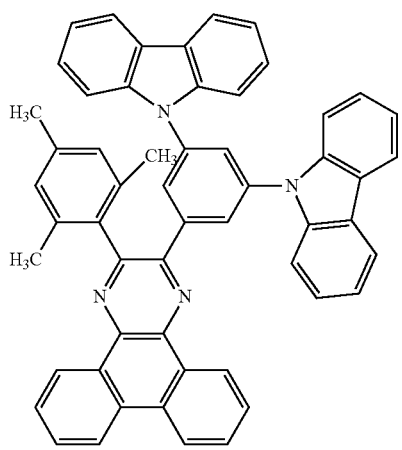
(133)
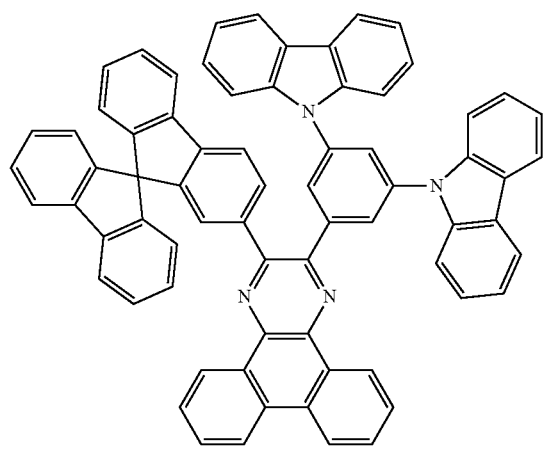

-continued
(134)
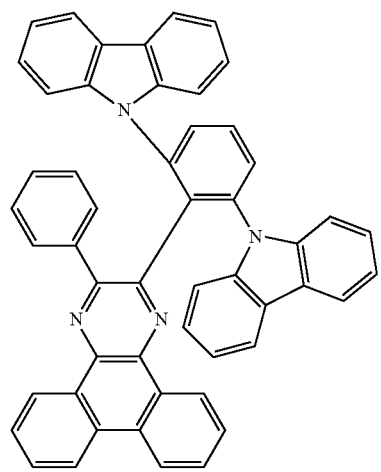
(135)
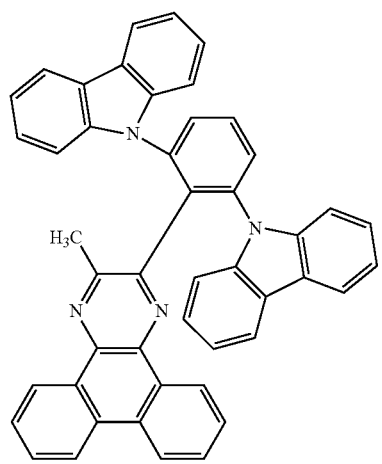
(136)
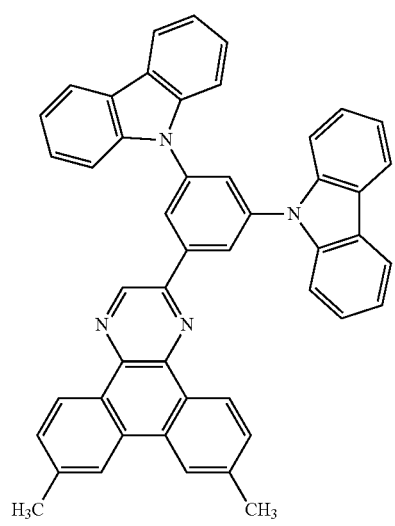
(137)
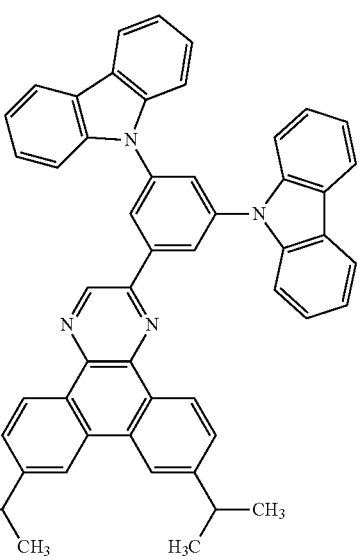
(138)
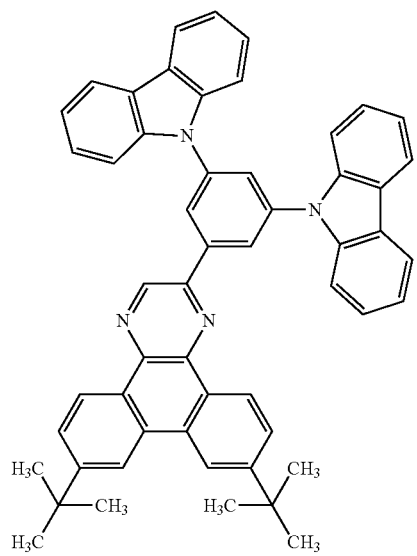
(139)
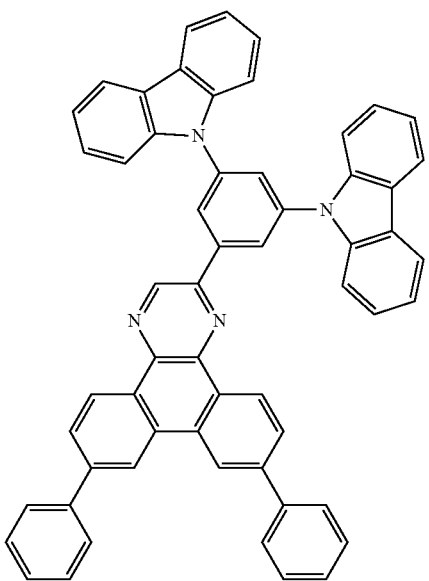

-continued
(140)
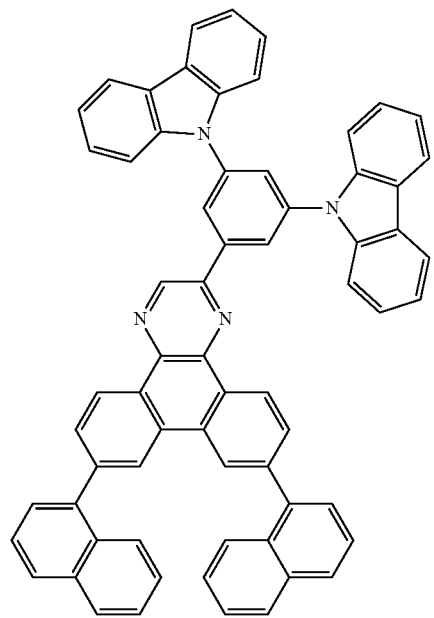
(141)
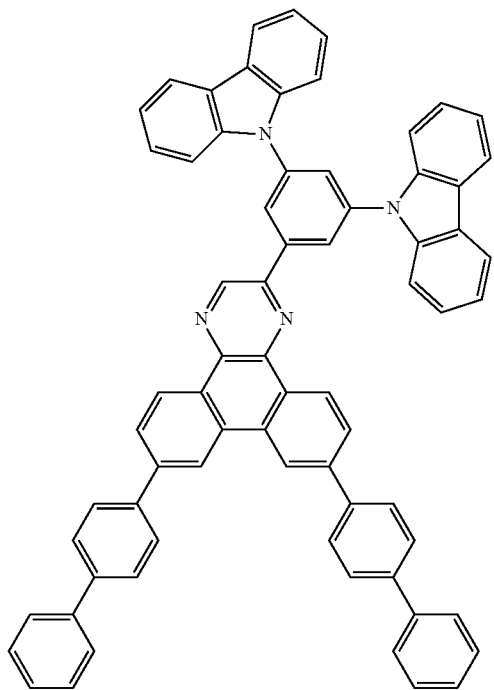
(142)
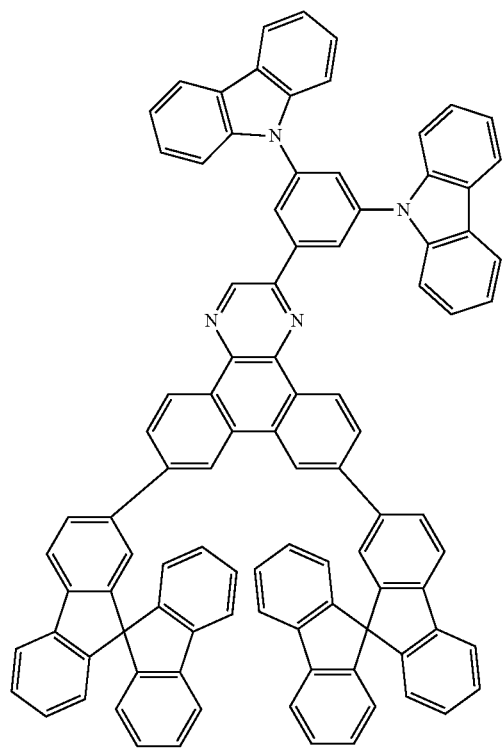
(143)
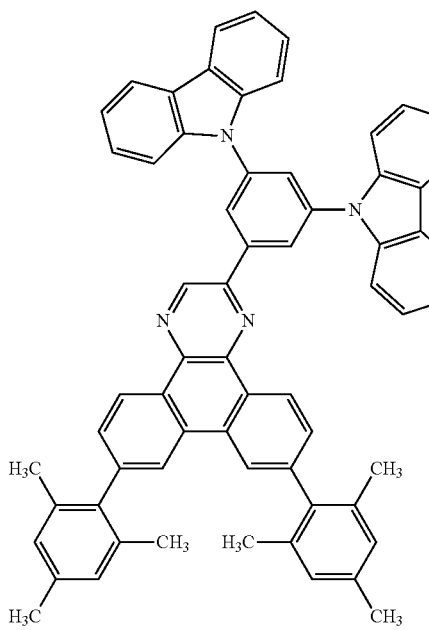

-continued
(144)
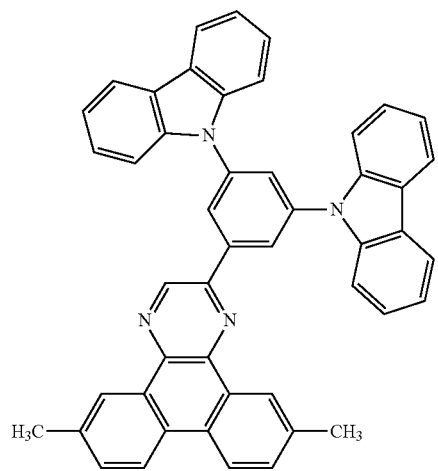
(145)
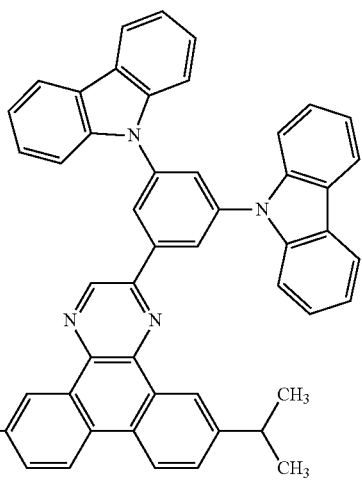
(146)
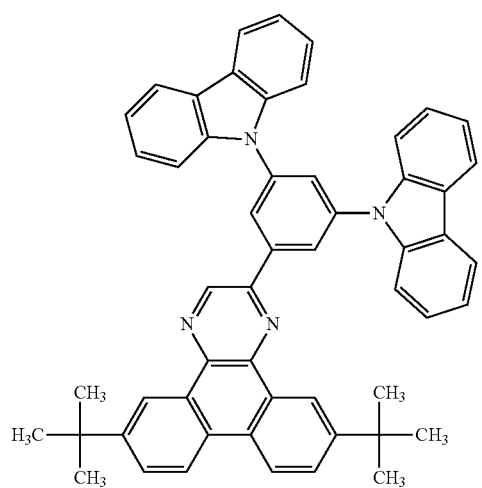
(147)
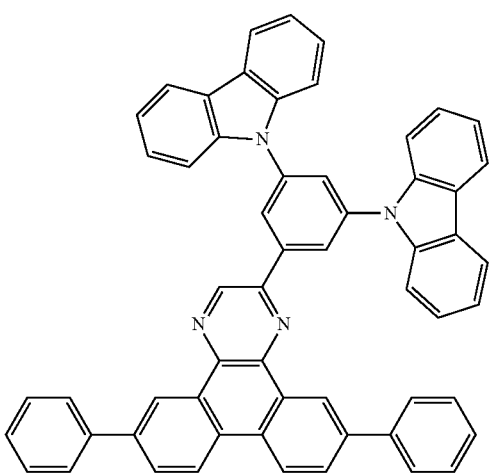
(148)
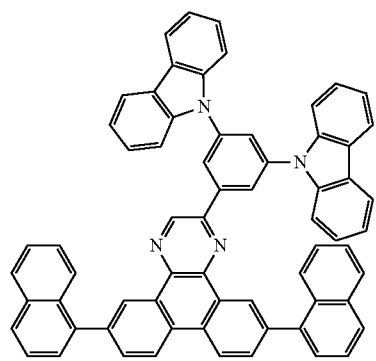
(149)
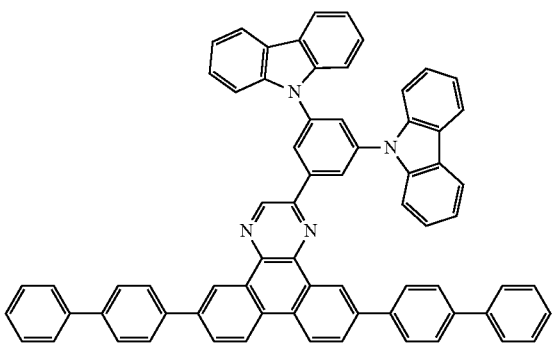

-continued
(150)
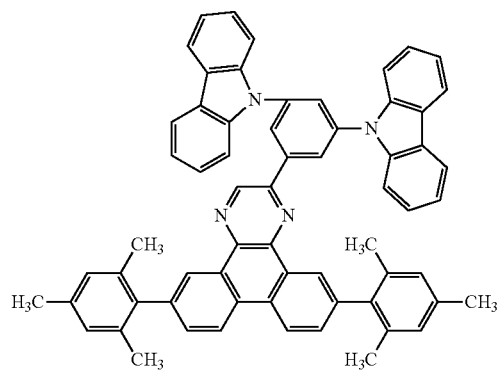
(151)
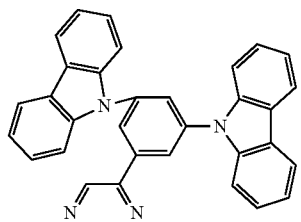
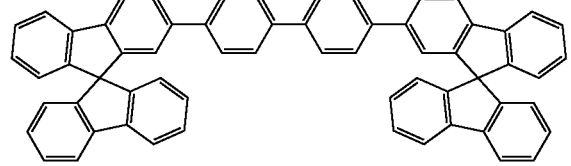
(152)
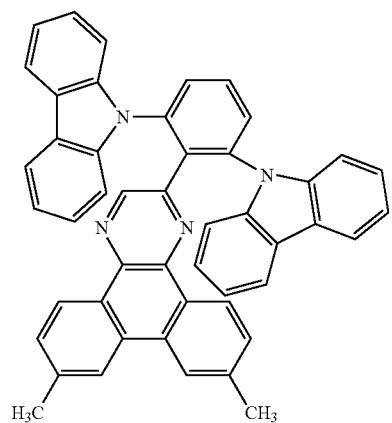
(153)
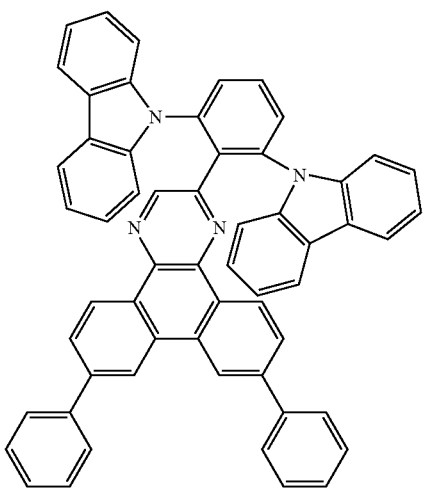
(154)
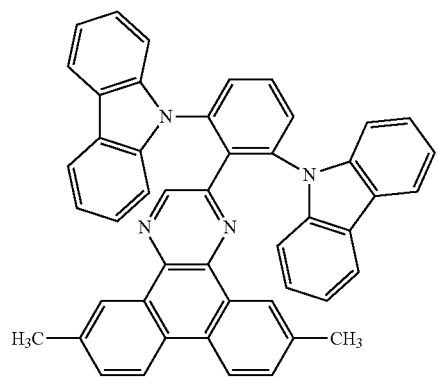
(155)
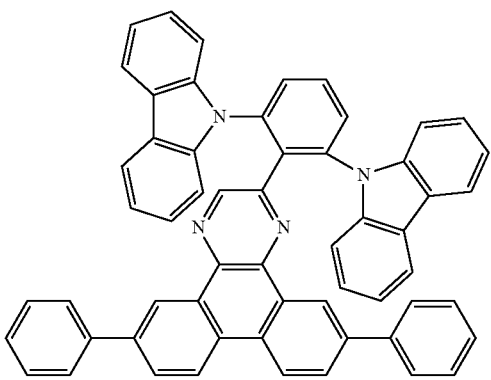

-continued
(200)
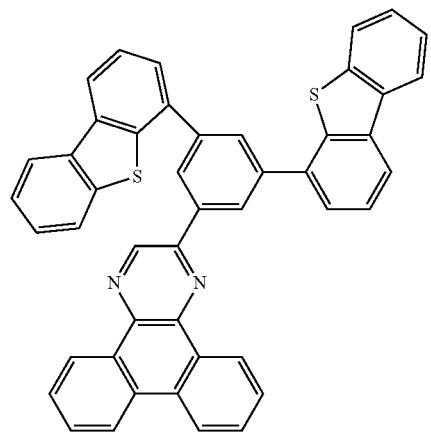
(201)
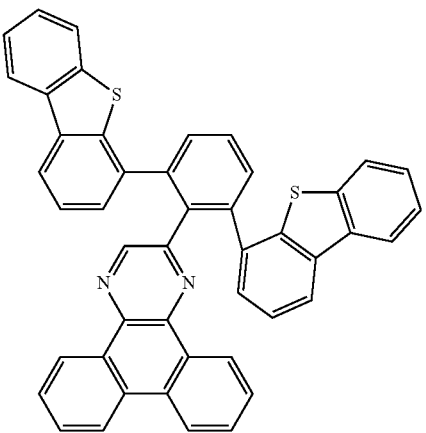
(202)
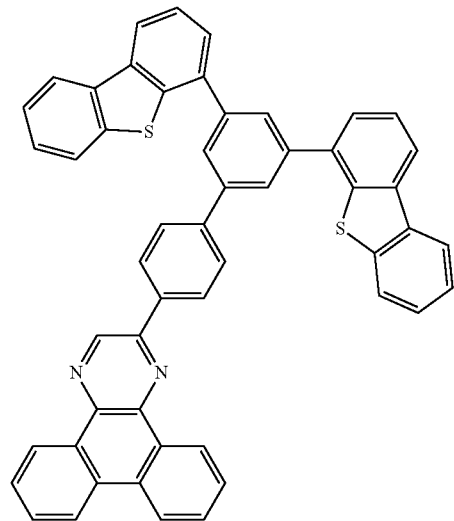
(203)
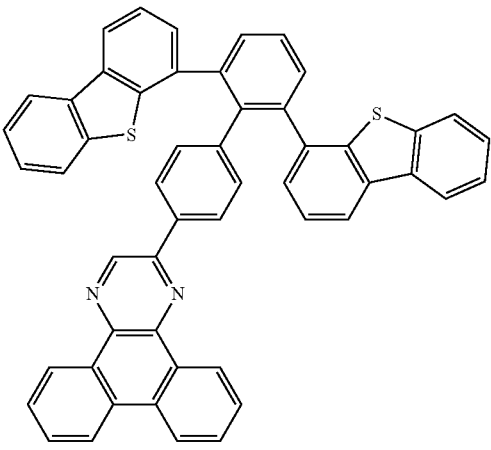
(204)
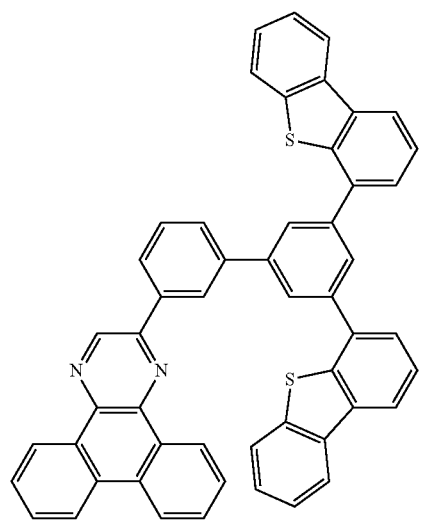
(205)
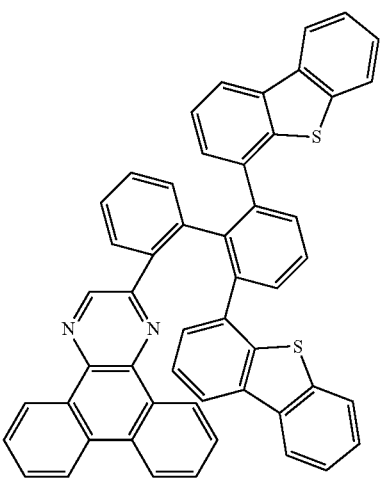

-continued
(206)
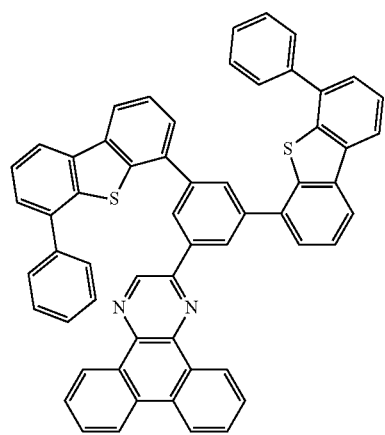
(207)
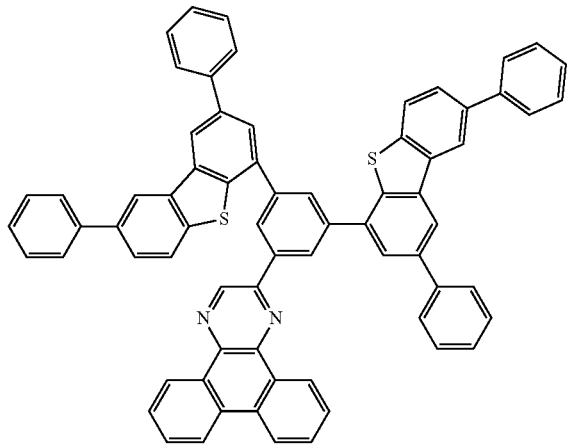
(209)
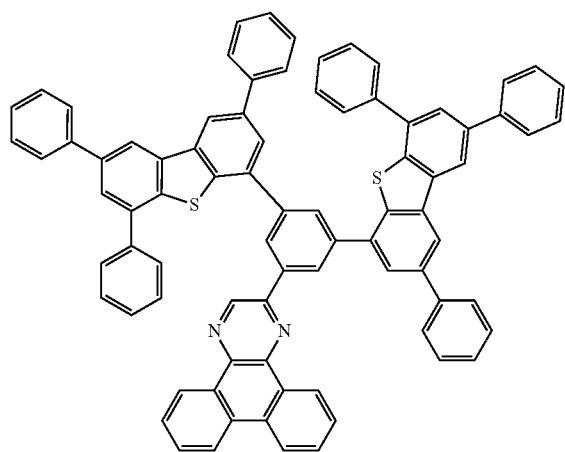
(208)
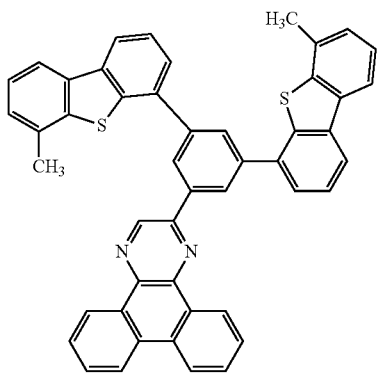
(210)
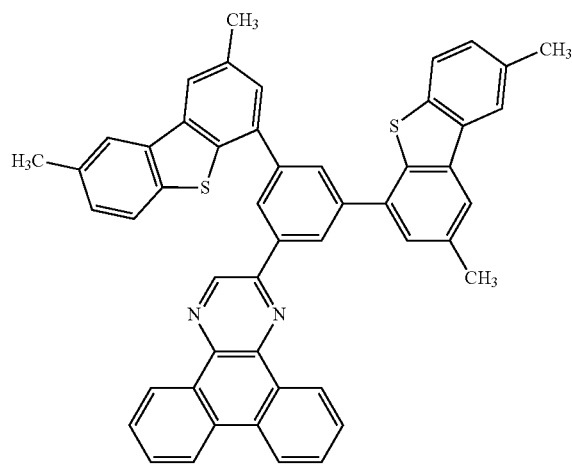
(211)
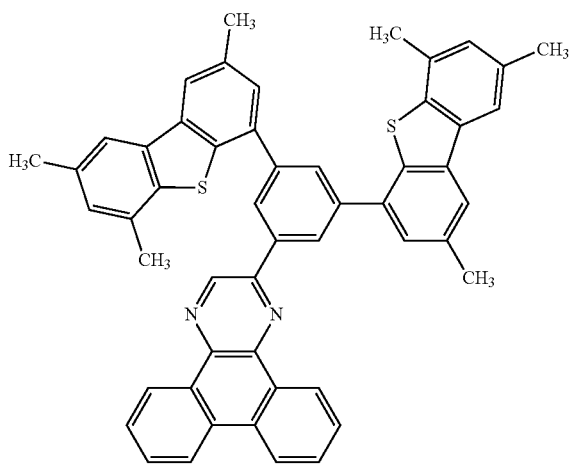

-continued
(212)
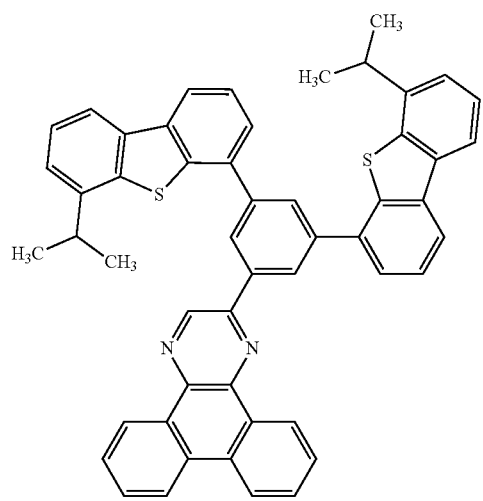
(213)
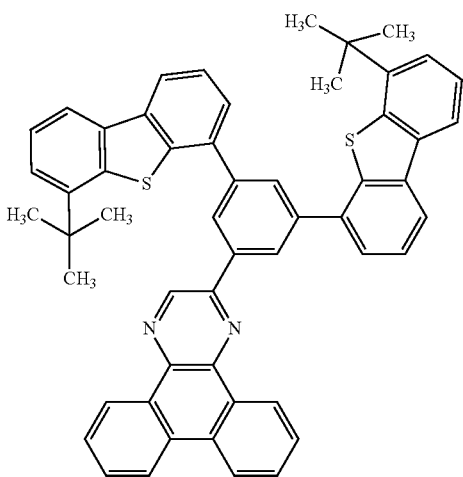
(214)
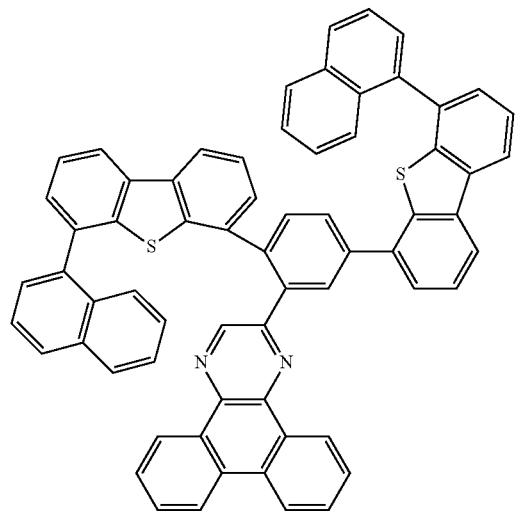
(215)
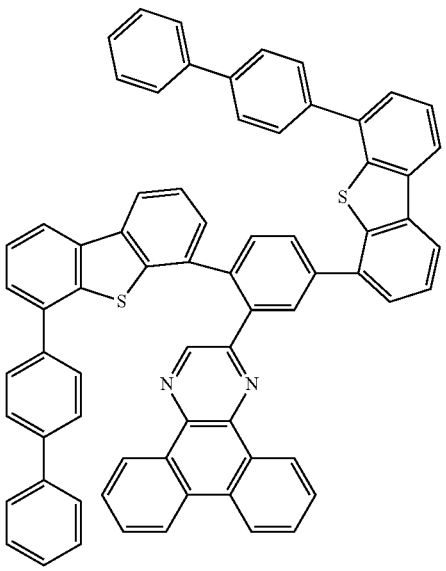
(216)
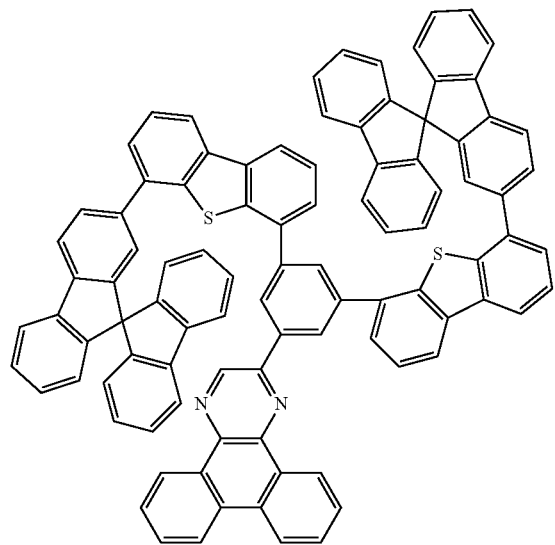
(217)
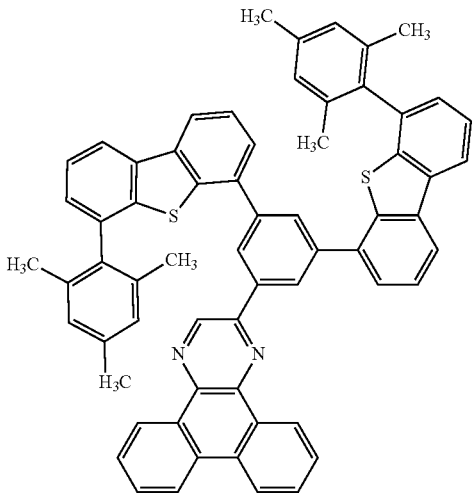

(218)
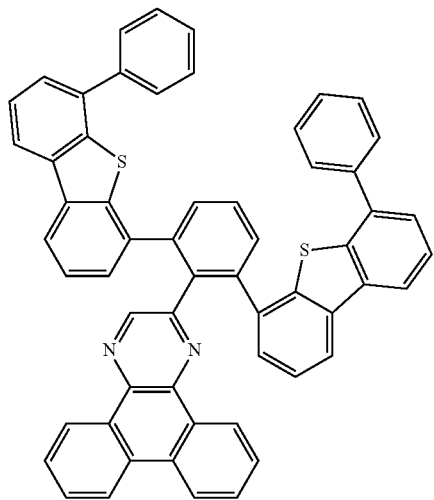
(219)
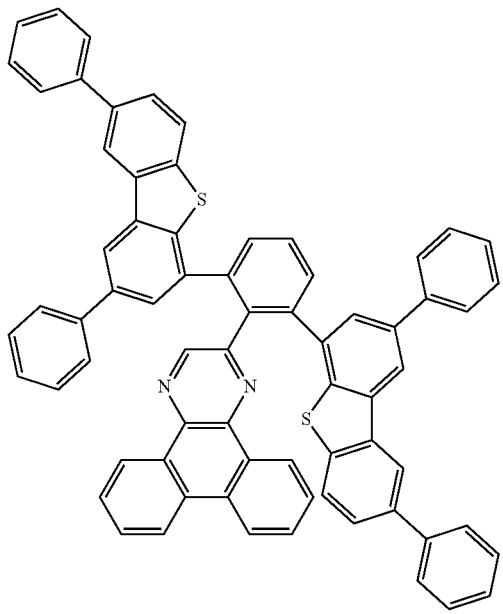
(220)
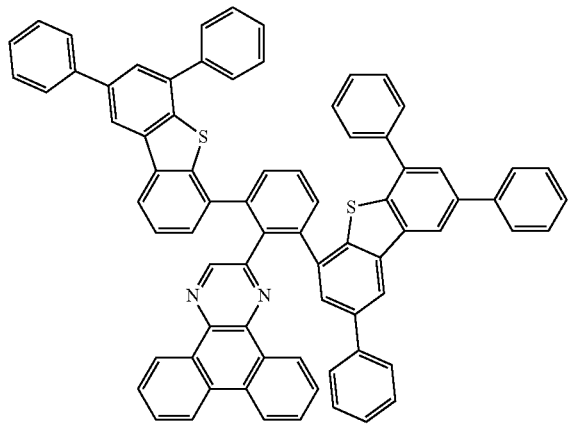
(221)
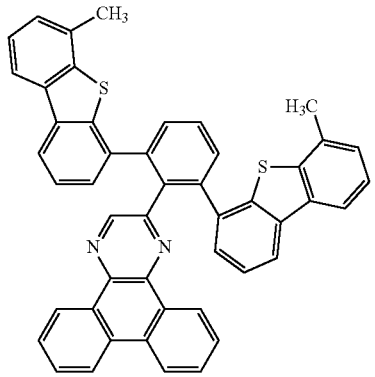
(222)
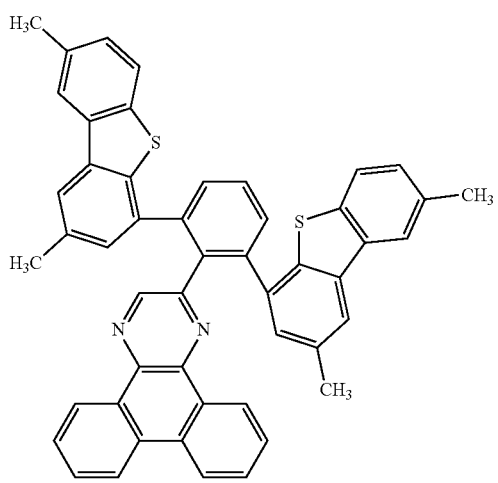
(223)
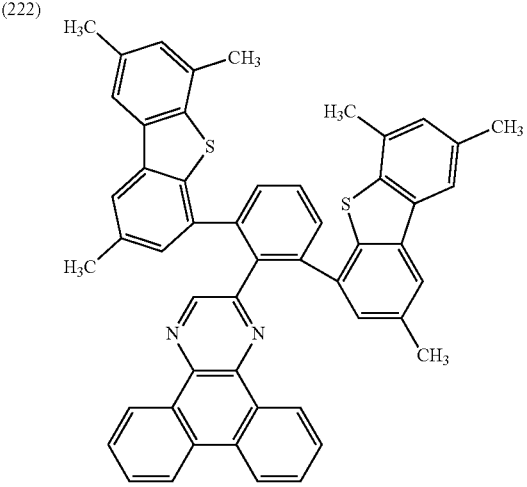

-continued
(224)
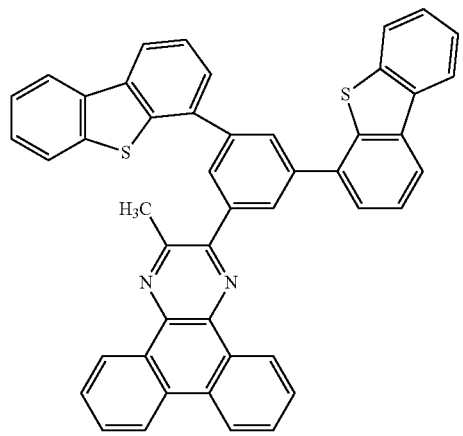
(225)
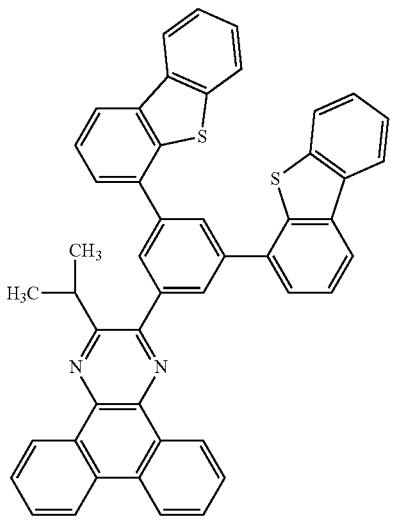
(226)
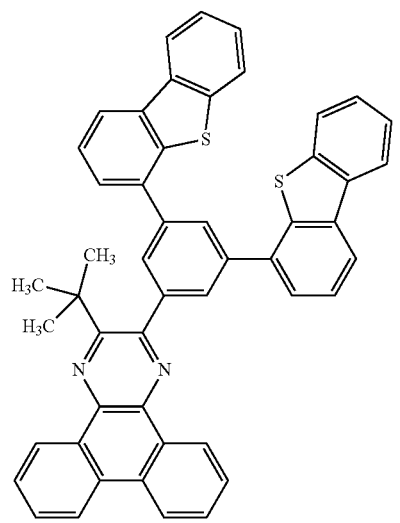
(227)
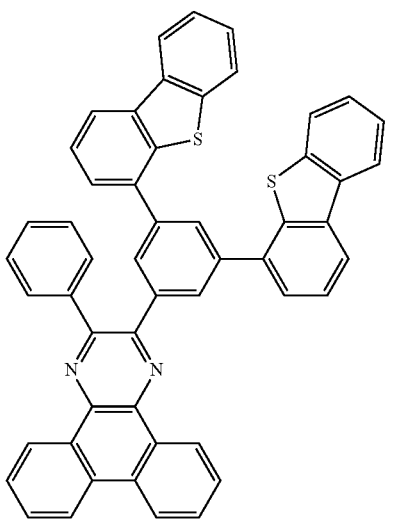
(228)
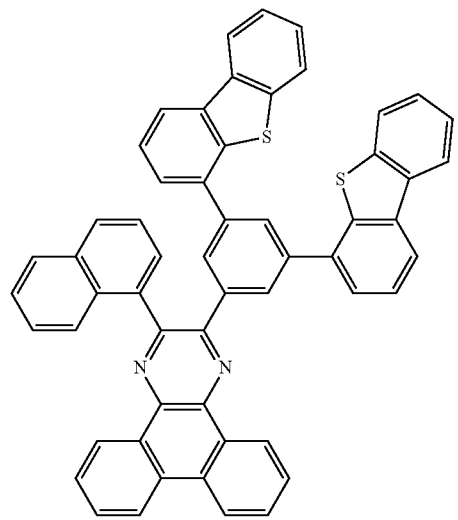
(229)
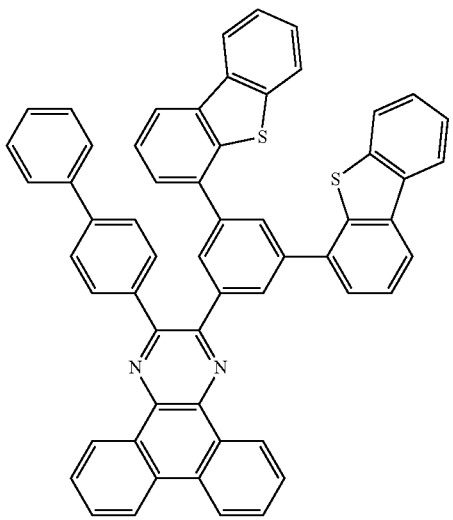

-continued
(230)
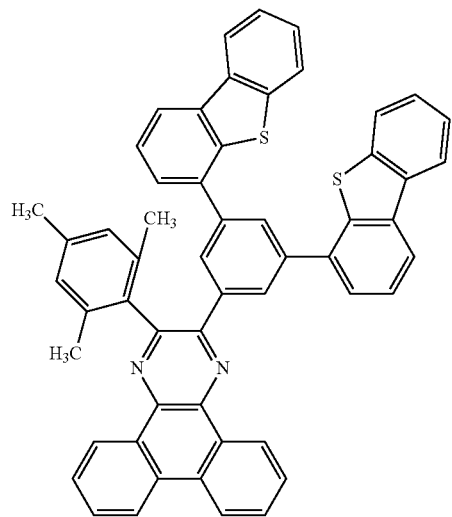
(231)
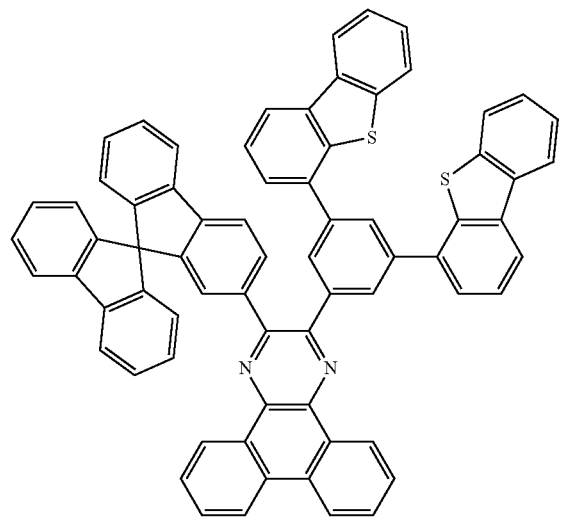
(232)
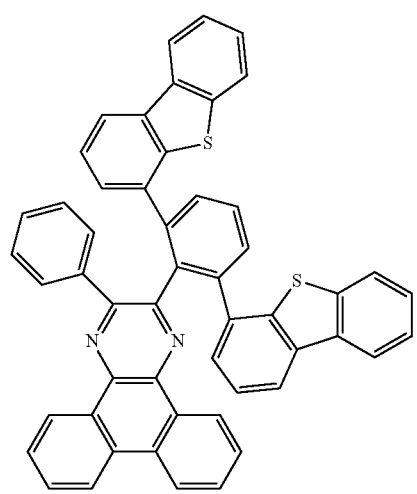
(233)
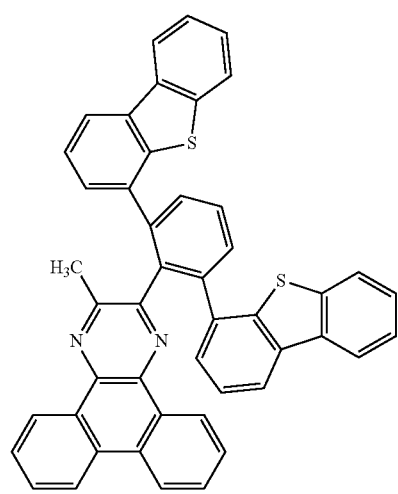
(234)
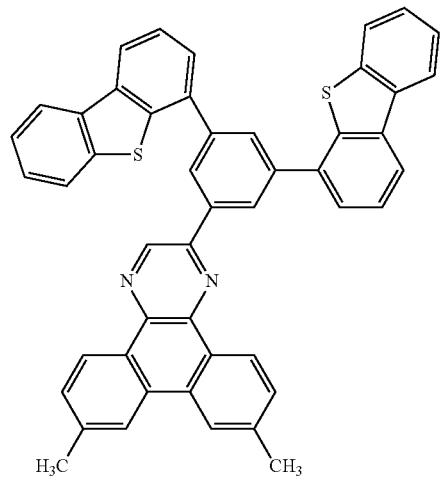
(235)
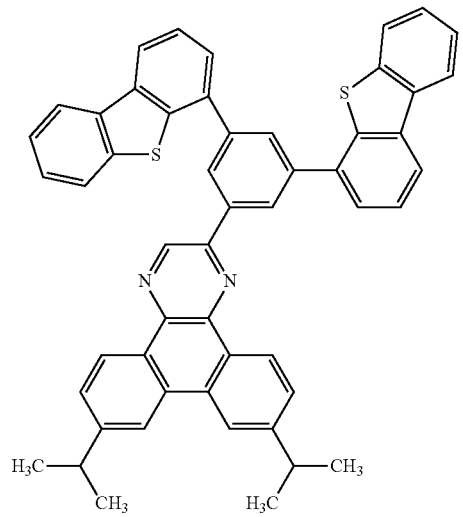

-continued
(236)
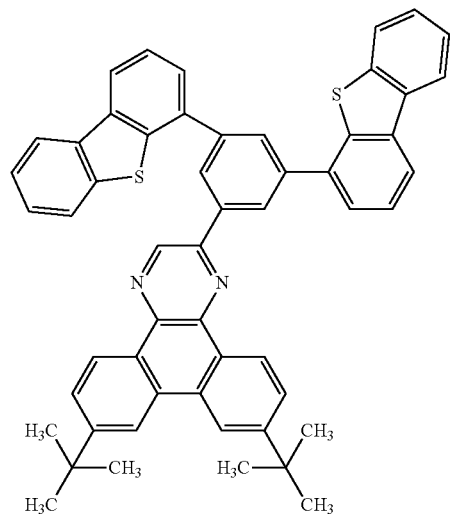
(237)
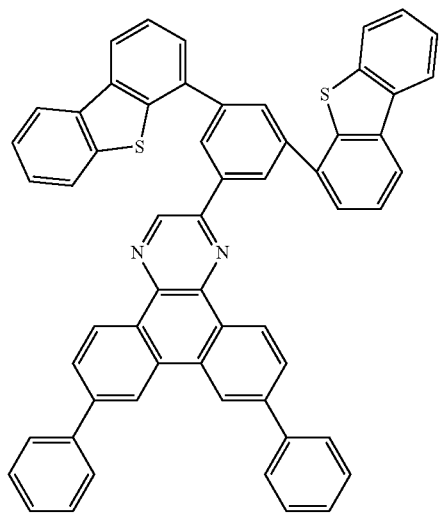
(238)
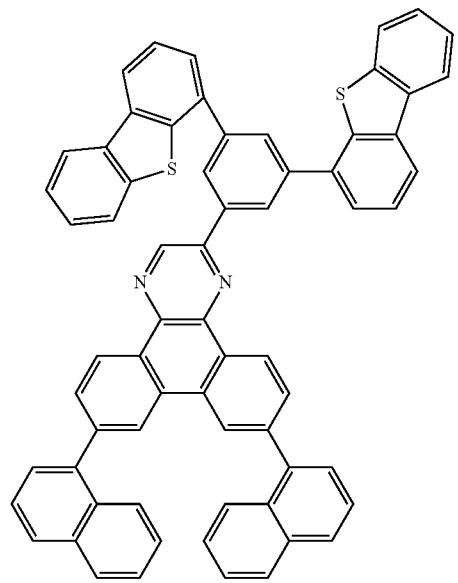
(239)
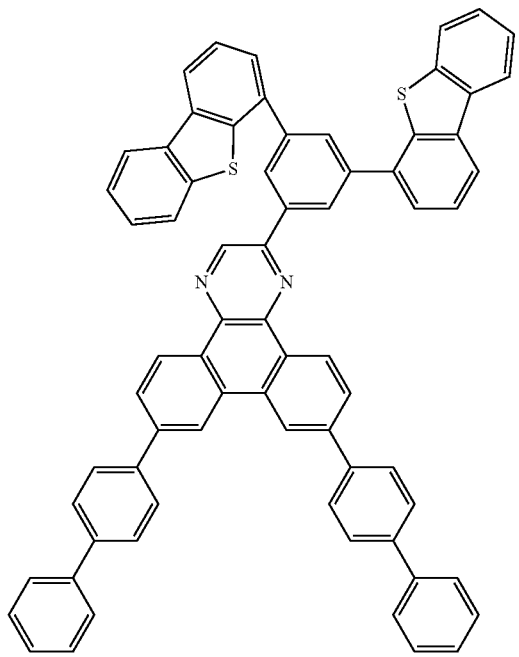

-continued
(240)
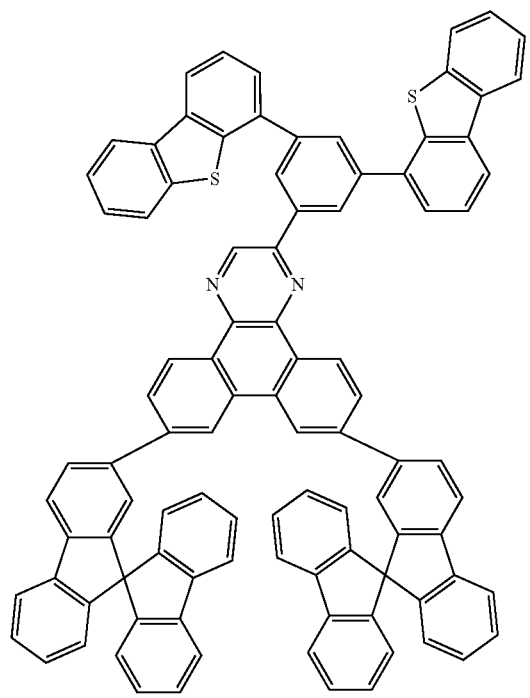
(241)
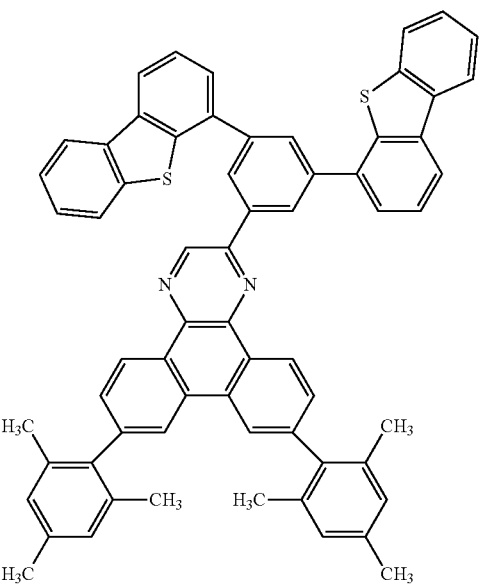
(242)
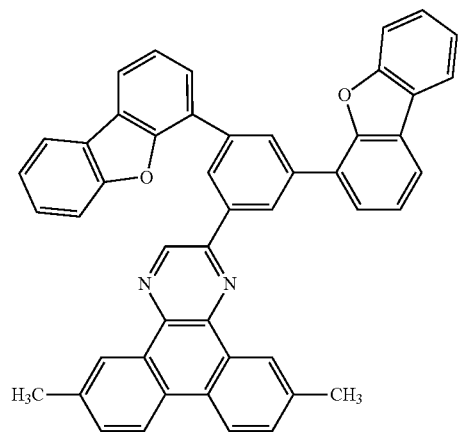
(243)
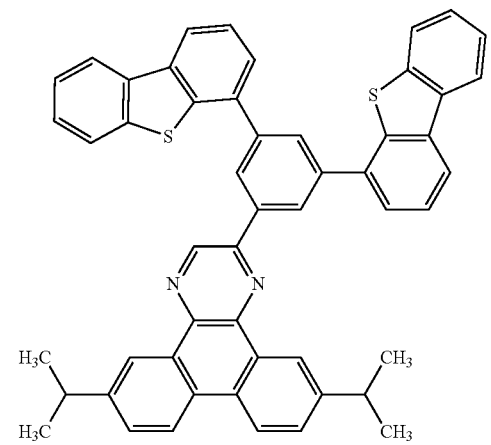
(244)
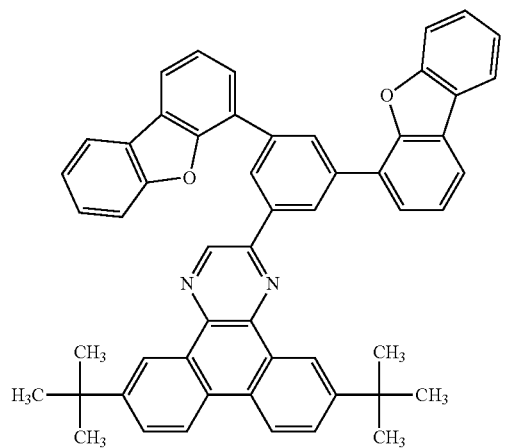
(245)
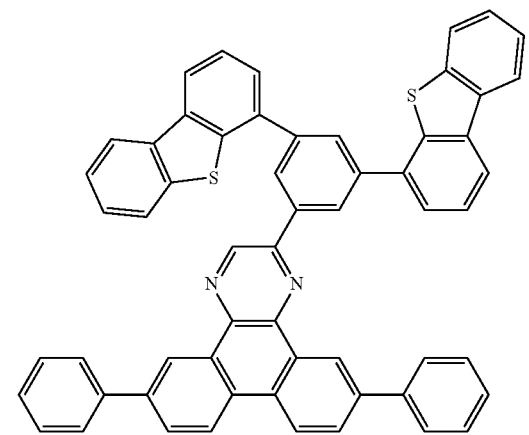

-continued
(246)
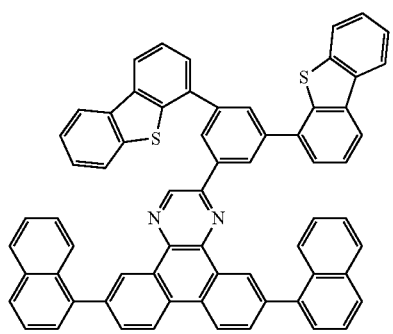
(247)
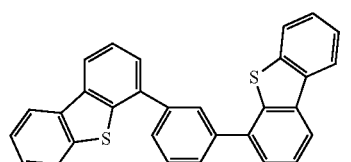
(248)
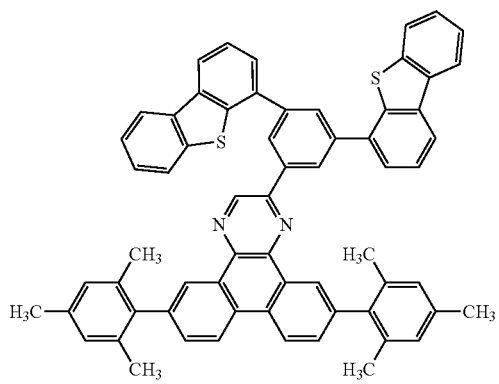
(249)
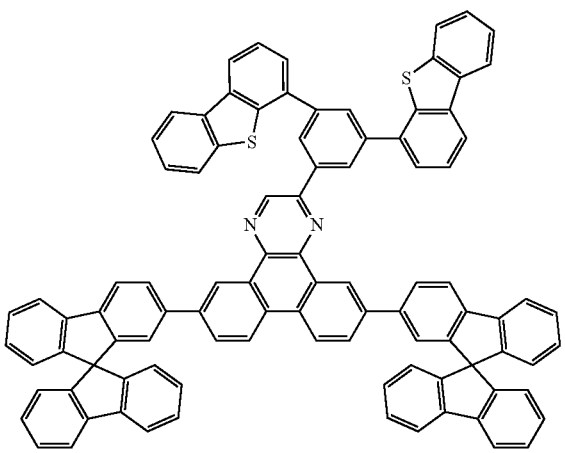
(250)
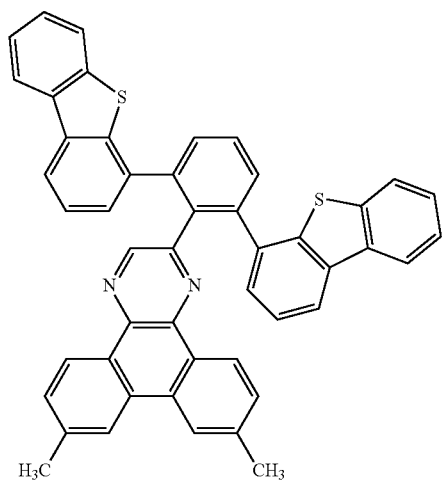
(251)
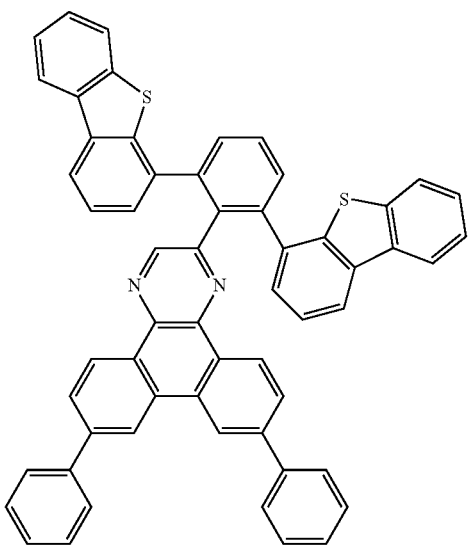

-continued
(252)
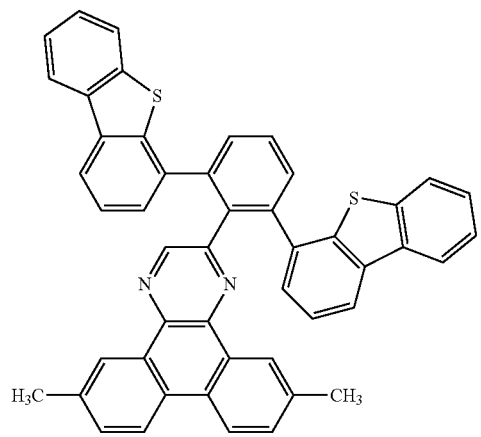
(253)
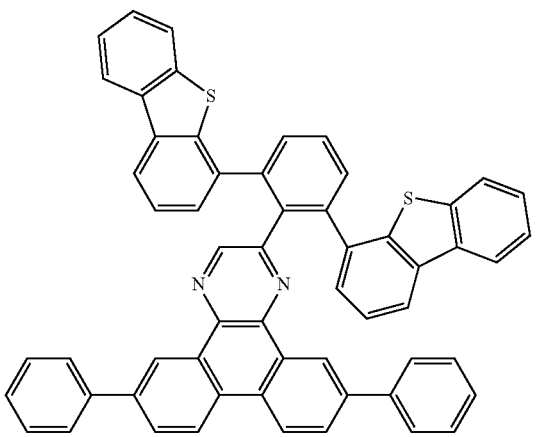
(300)
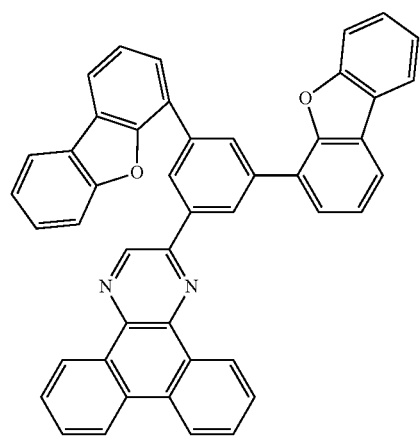
(301)
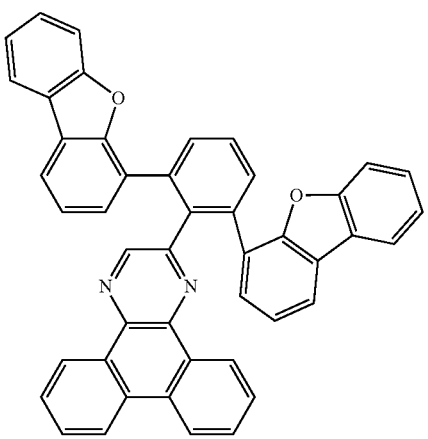
(302)
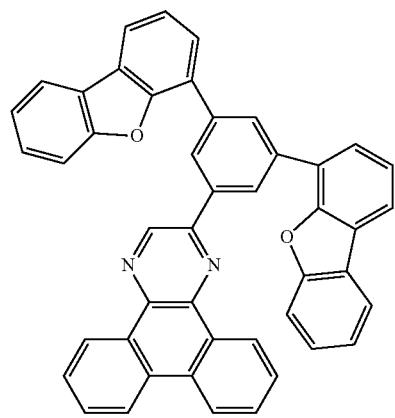
(303)
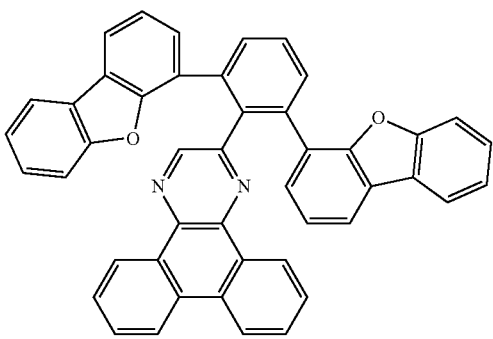

-continued
(304)
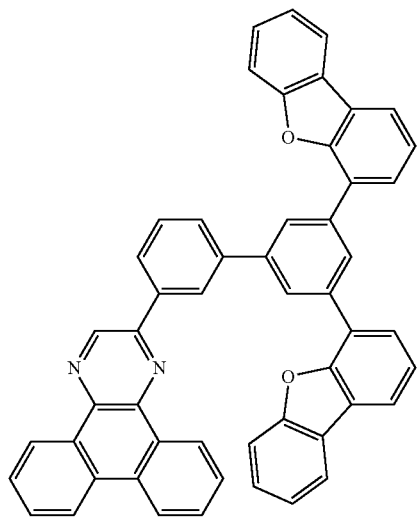
(305)
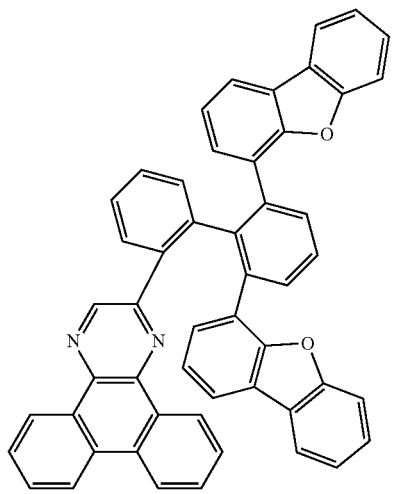
(306)
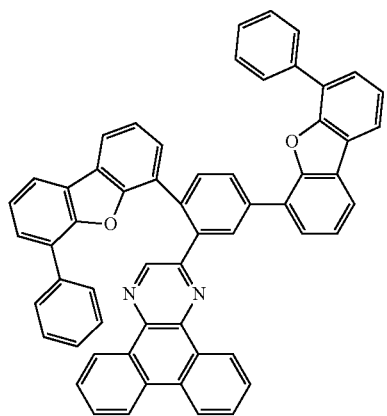
(307)
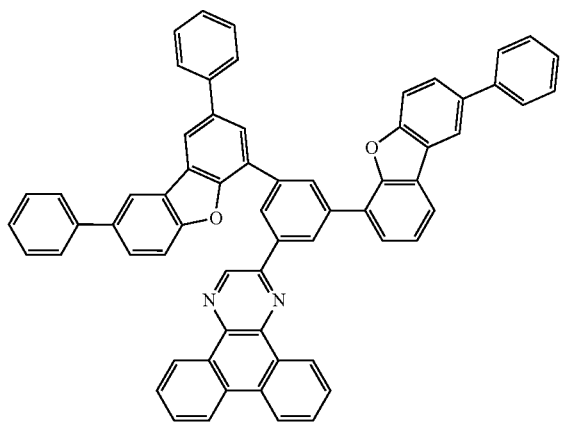
(308)
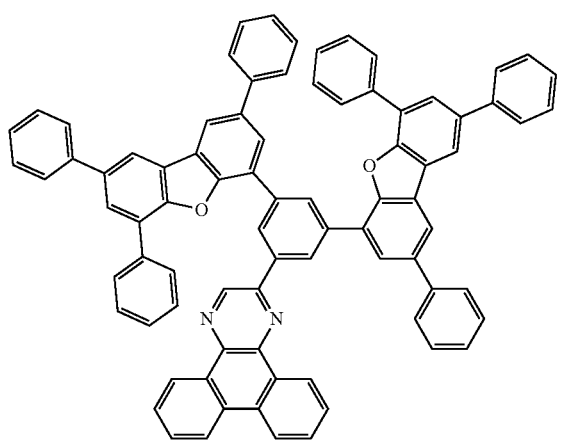
(309)
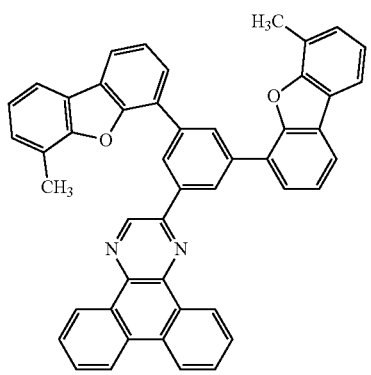

-continued
(310)
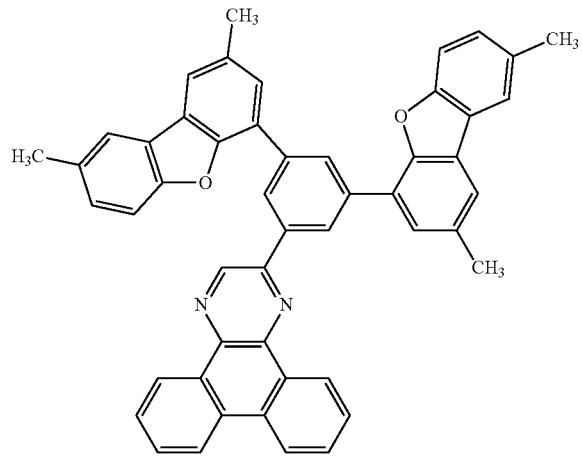
(311)
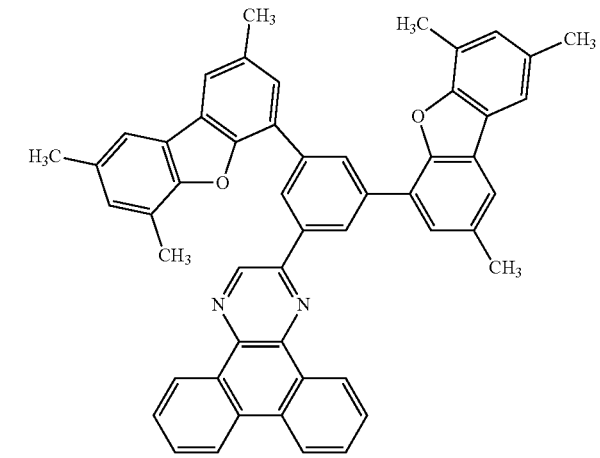
(312)
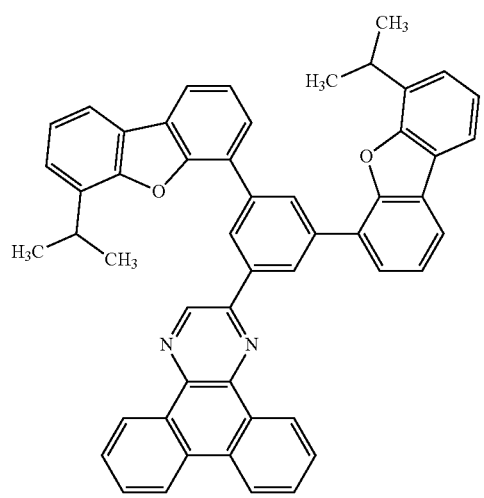
(313)
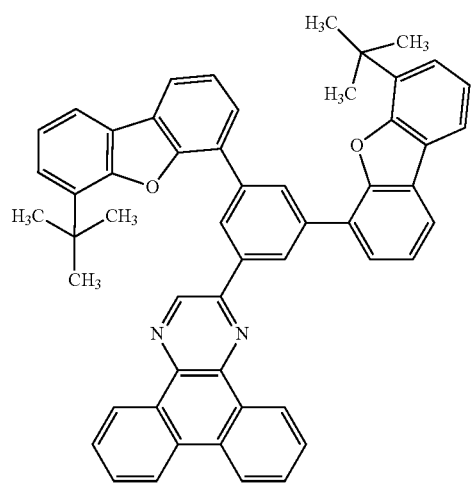
(314)
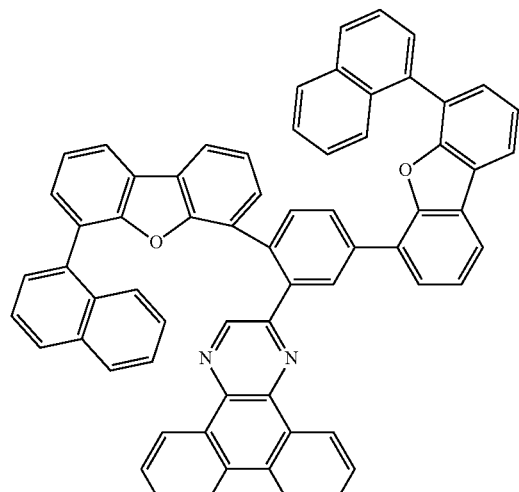
(315)
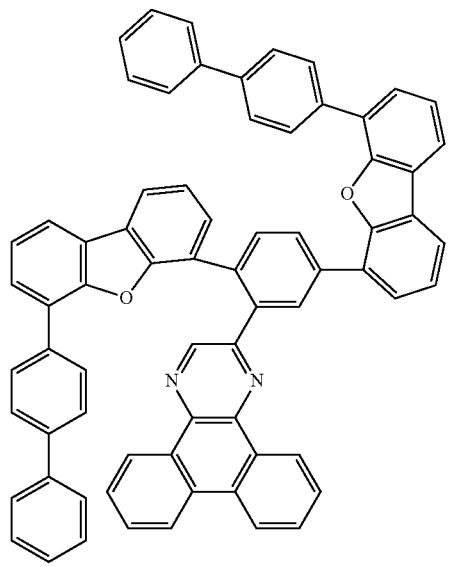

-continued
(316)
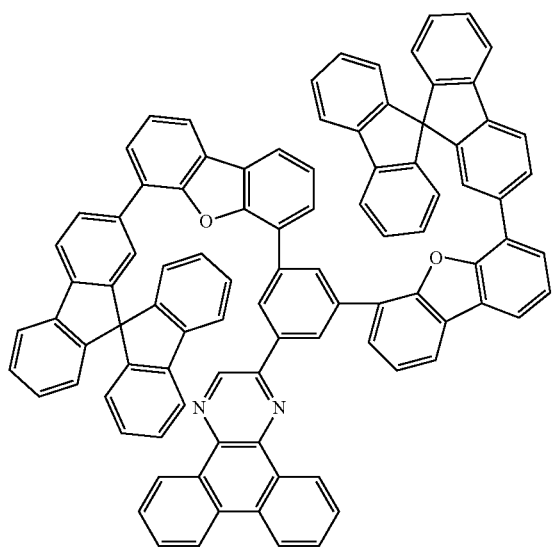
(317)
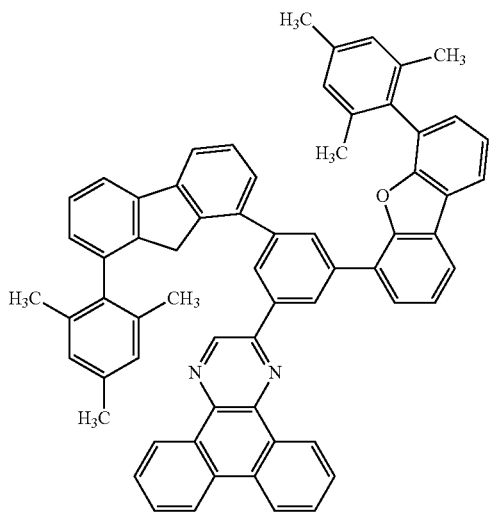
(318)
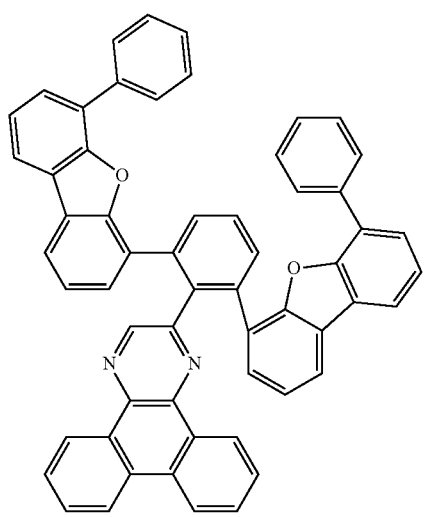
(319)
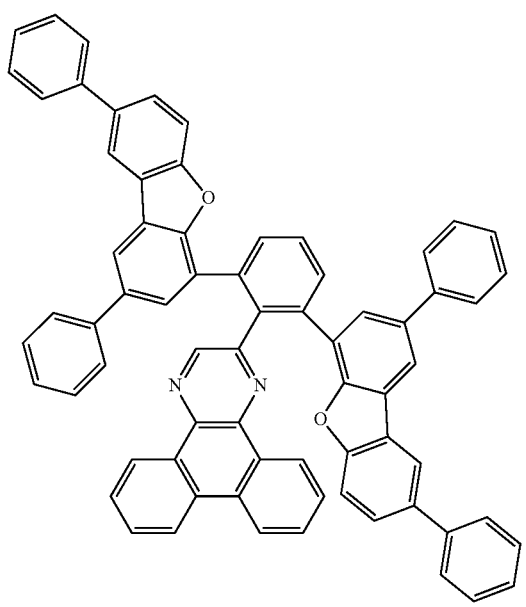
(320)
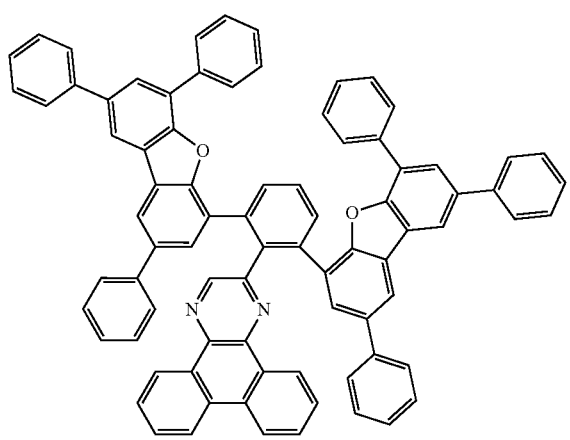
(321)
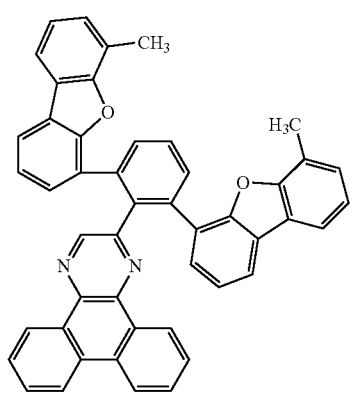

-continued
(322)
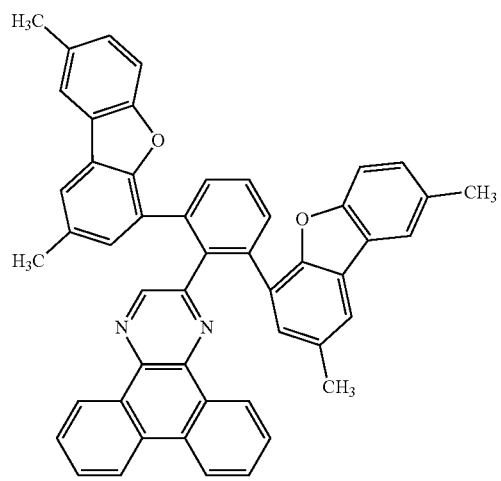
(323)
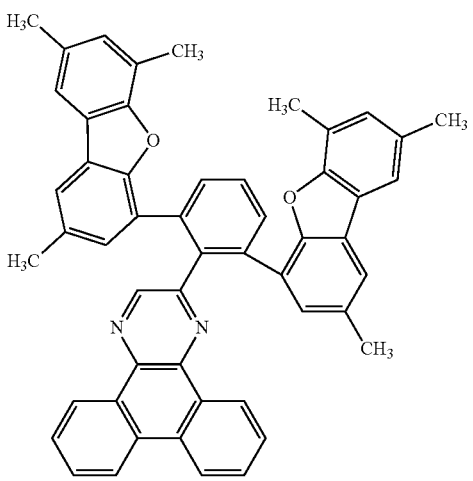
(324)
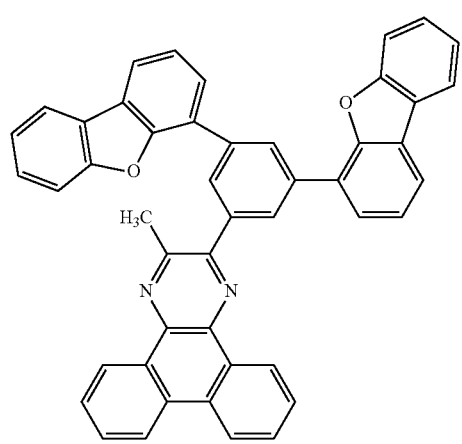
(325)
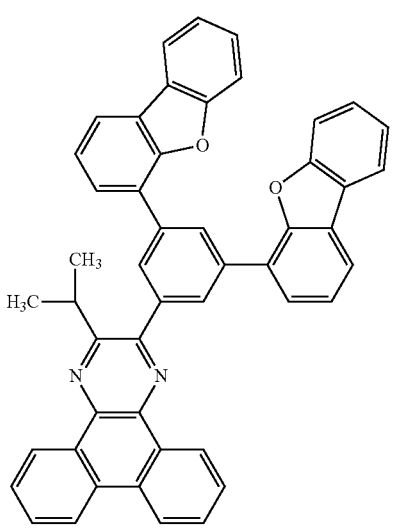
(326)
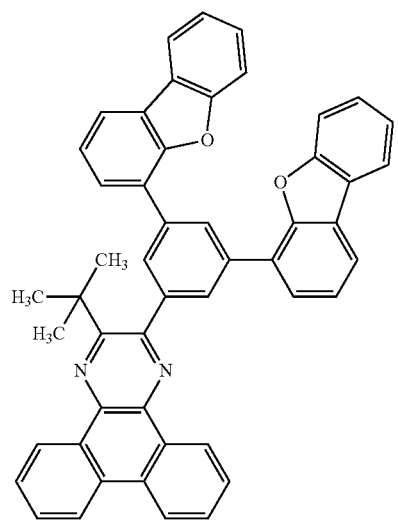
(327)
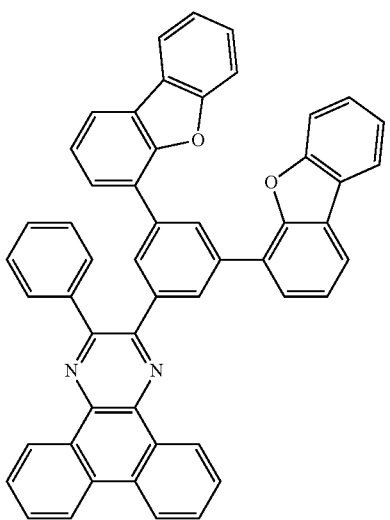

-continued
(328)
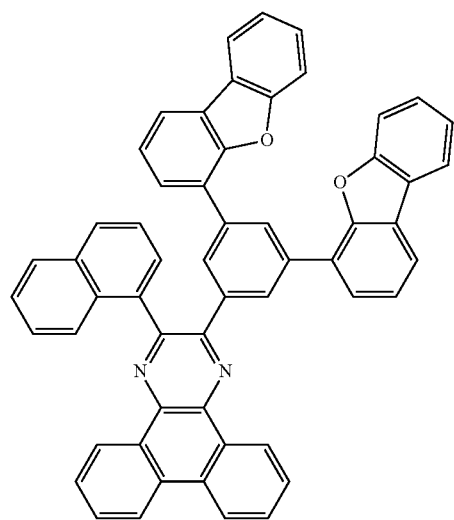
(329)
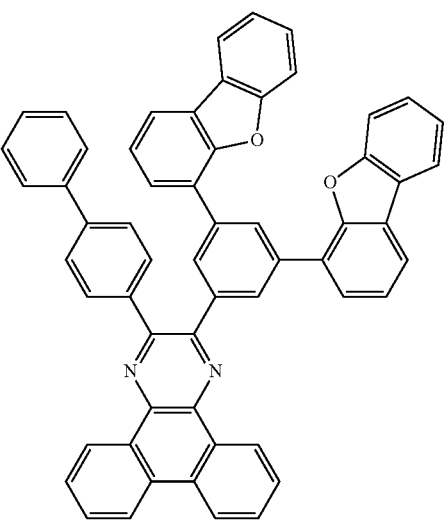
(330)
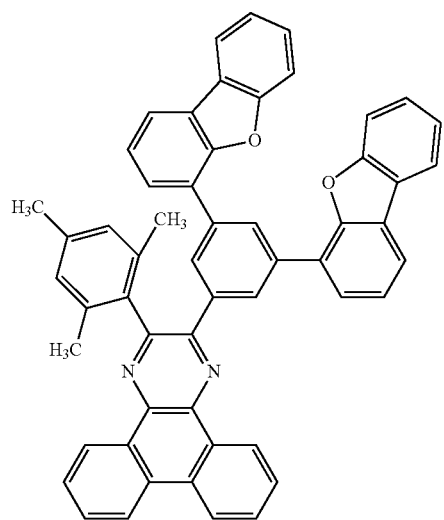
(331)
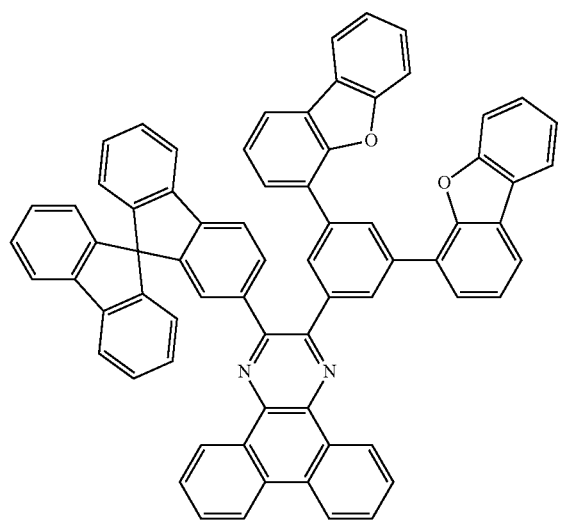
(332)
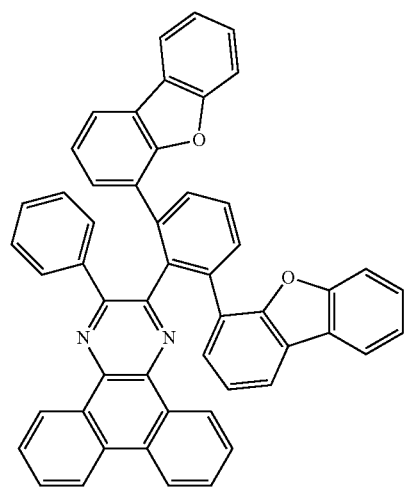
(333)
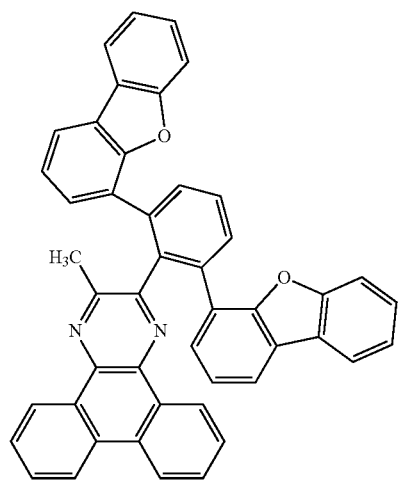

-continued
(334)
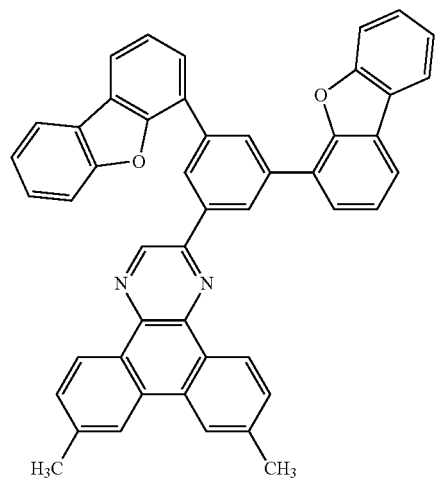
(335)
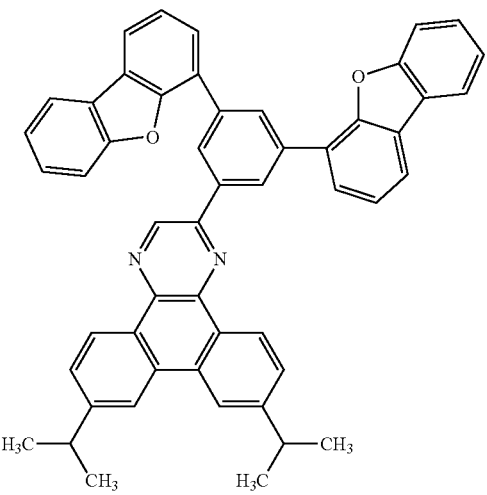
(336)
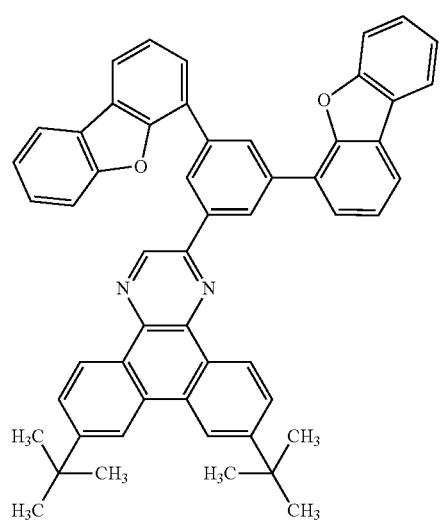
(337)
(338)
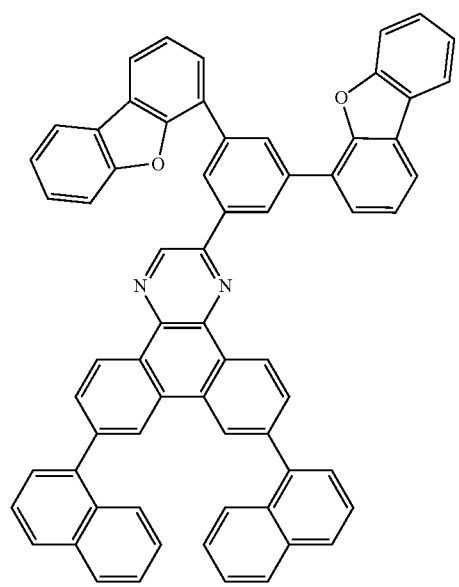
(339)
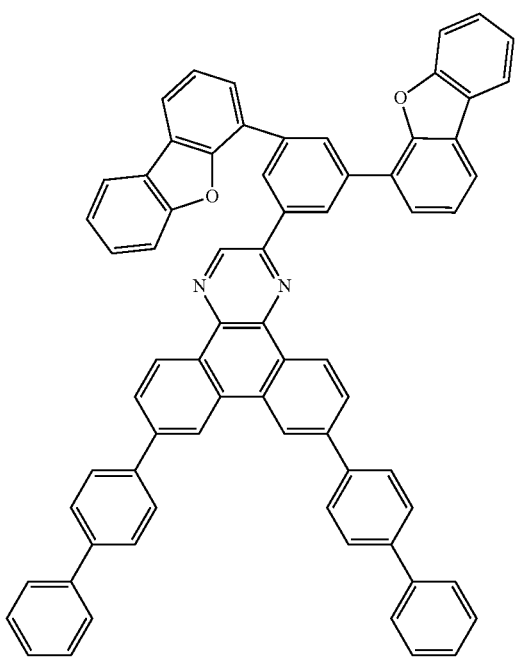

-continued
(340)
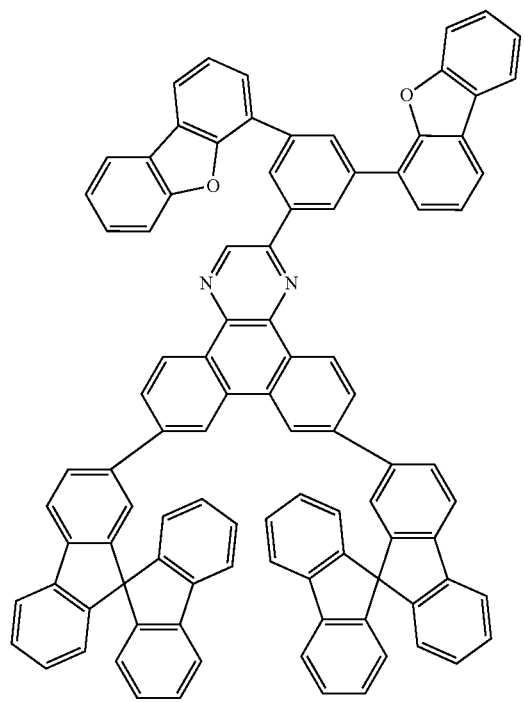
(341)
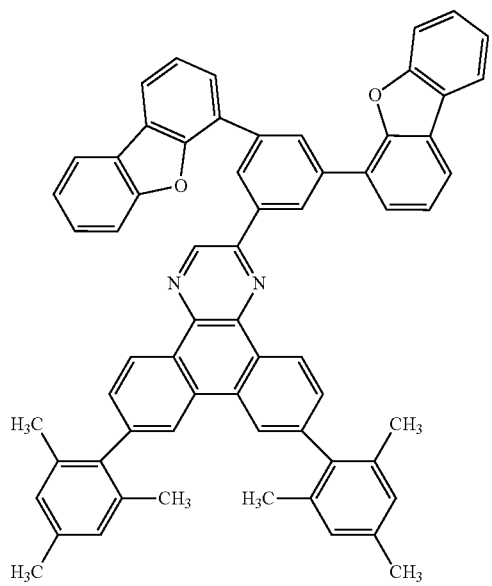
(342)
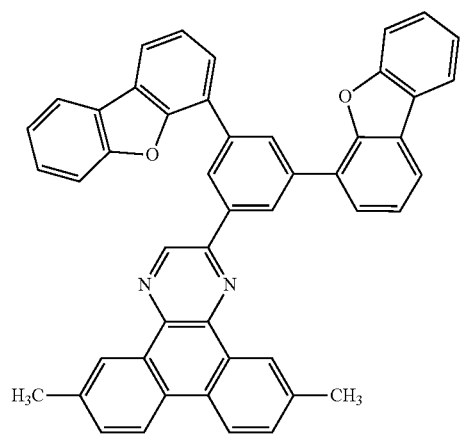
(343)
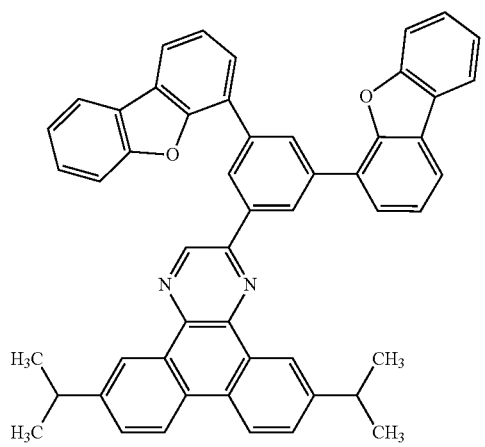
(344)
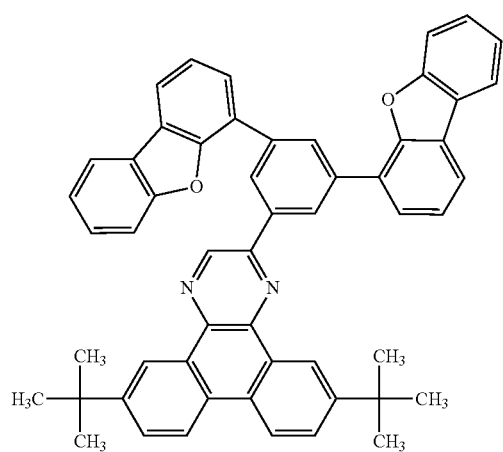
(345)
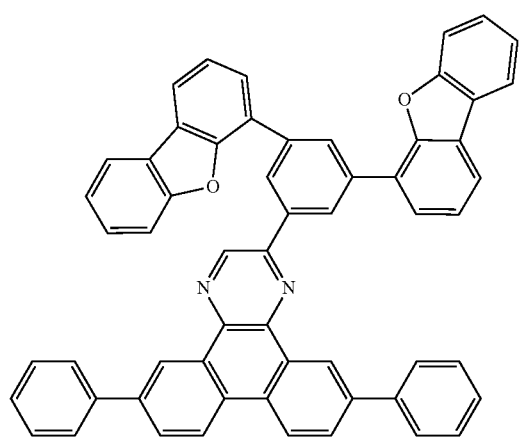

-continued
(346)
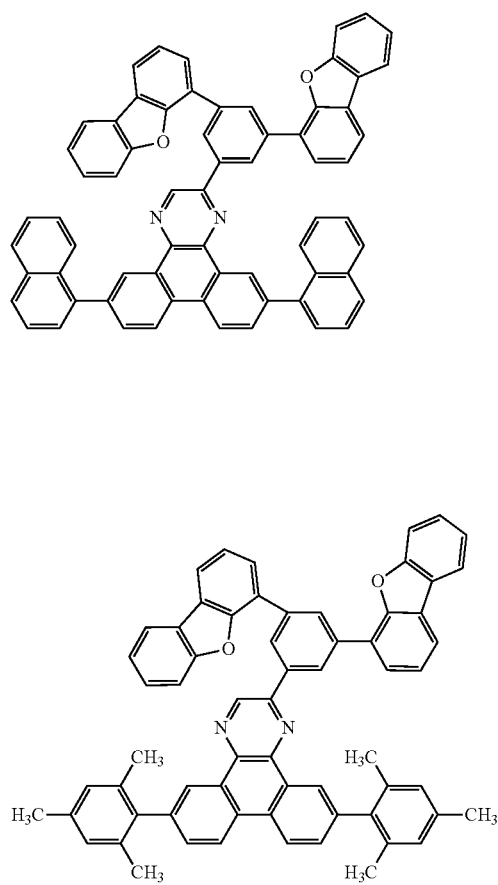
(347)
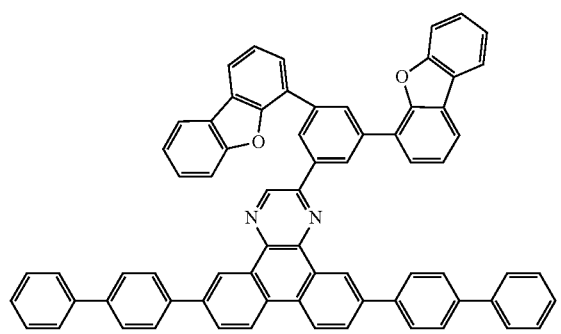
(348)
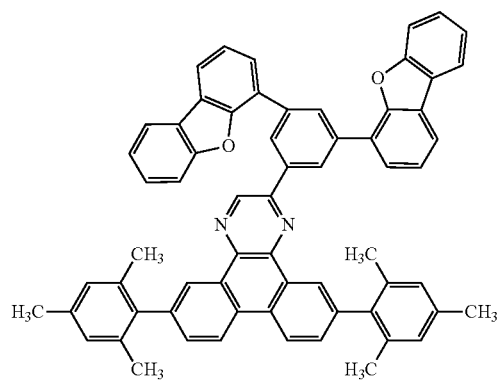
(349)
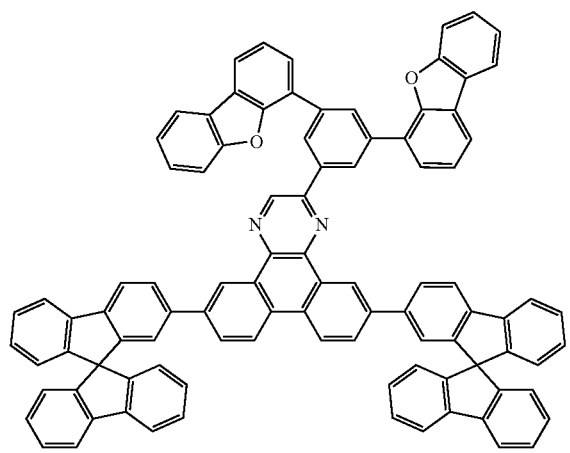
(350)
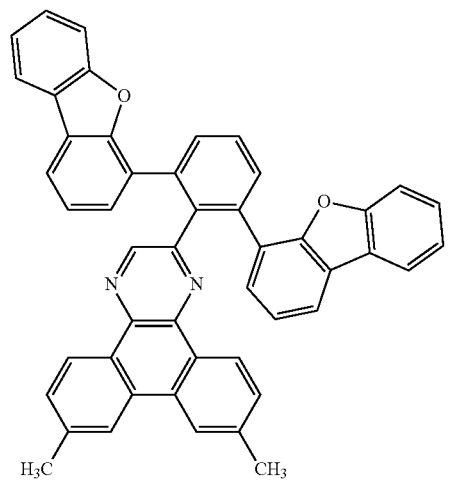
(351)
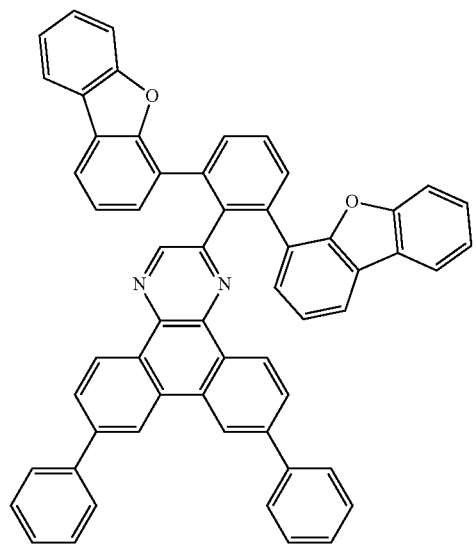

-continued

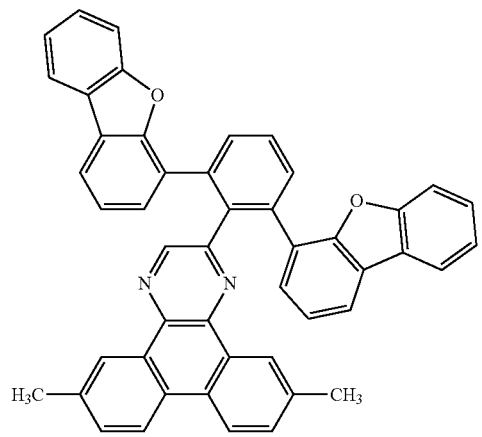

(352)

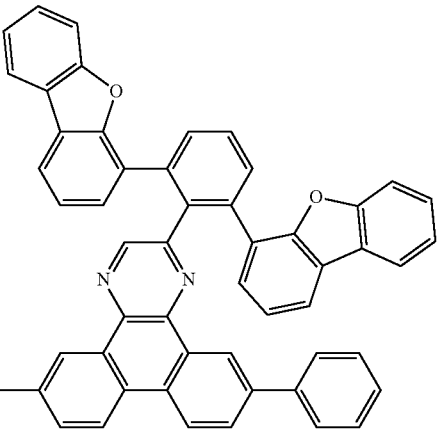

(353)

A variety of reactions can be applied to the method of synthesizing the heterocyclic compounds. For example, through the following synthesis reactions, the heterocyclic compounds described in this embodiment can be synthesized. Note that the methods of synthesizing the heterocyclic compounds, which are each one embodiment of the present invention, are not limited to the synthesis methods below. Although description of the synthesis method is made using the general formula (G2), the heterocyclic compounds represented by the other general formulae in this embodiment can be synthesized in the similar manner.

<<Synthesis Method 1>>

First, the synthesis scheme (A-1) is shown below.

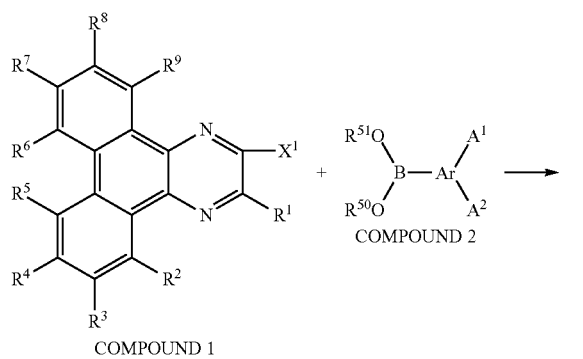

(A-1)

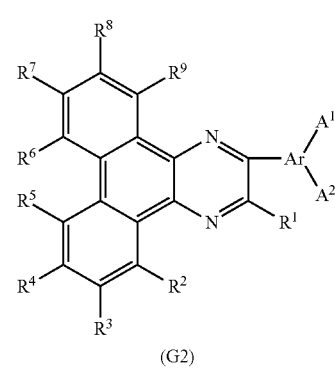

(G2)

The heterocyclic compound (G2) of one embodiment of the present invention can be synthesized according to the synthesis scheme (A-1). Specifically, a halide of a dibenzo[f,h]quinoxaline derivative (Compound 1) is coupled with an organoboron compound or boronic acid of a carbazole derivative, a dibenzofuran derivative, or a dibenzothiophene derivative (Compound 2) by a Suzuki-Miyaura reaction, whereby the heterocyclic compound (G2) described in this embodiment can be obtained.

In the synthesis scheme (A-1), $A^1$ and $A^2$ each independently represent any of a substituted or unsubstituted carbazolyl group, a substituted or unsubstituted dibenzothiophenyl group, and a substituted or unsubstituted dibenzofuranyl group; Ar represents an aromatic hydrocarbon group having 6 to 13 carbon atoms; the aromatic hydrocarbon group may have a substituent; substituents of the aromatic hydrocarbon group may be bonded to each other to form a ring; $R^1$ to $R^9$ each independently represent any of hydrogen, an alkyl group having 1 to 4 carbon atoms, and a substituted or unsubstituted aryl group having 6 to 13 carbon atoms; $R^{50}$ and $R^{51}$ each independently represent hydrogen or an alkyl group having 1 to 6 carbon atoms; $R^{50}$ and $R^{51}$ may be bonded to each other to form a ring; and $X^1$ represents a halogen.

Examples of the palladium catalyst that can be used in the synthesis scheme (A-1) include, but are not limited to, palladium(II)acetate, tetrakis(triphenylphosphine)palladium(0), and bis(triphenylphosphine)palladium(II)dichloride.

Examples of the ligand of the palladium catalyst that can be used in the synthesis scheme (A-1) include, but are not limited to, tri(o-tolyl)phosphine, triphenylphosphine, and tricyclohexylphosphine.

Examples of the base that can be used in the synthesis scheme (A-1) include, but are not limited to, an organic base such as sodium tert-butoxide, inorganic bases such as potassium carbonate and sodium carbonate.

Examples of the solvent that can be used in the synthesis scheme (A-1) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of an ether such as ethylene glycol dimethyl ether and water. A mixed solvent of toluene and water; a mixed solvent of toluene, ethanol, and water; or a mixed solvent of ether such as ethylene glycol dimethyl ether and water is preferable.

As a coupling reaction shown in the synthesis scheme (A-1), the Suzuki-Miyaura Coupling Reaction using the organoboron compound or boronic acid represented by Compound 2 may be replaced with a cross coupling reaction using an organoaluminum compound, an organozirconium compound, an organozinc compound, an organotin compound, or the like. Note that the present invention is not limited thereto.

In the reaction shown in the synthesis scheme (A-1), an organoboron compound or boronic acid of a dibenzo[f,h]quinoxaline derivative may be coupled with a halide of a carbazole derivative, a dibenzofuran derivative, or a dibenzothiophene derivative or with a carbazole derivative, a dibenzofuran derivative, or a dibenzothiophene derivative which has a triflate group as a substituent, by the Suzuki-Miyaura reaction.

Thus, the heterocyclic compound of this embodiment can be synthesized.

<<Synthesis Method 2>>

A method of synthesizing a heterocyclic compound of this embodiment, which is different from Synthesis Method 1, is described below. First, the synthesis scheme (B-1) in which a boron compound of $A^1$ and $A^2$ is used as a material is shown below.

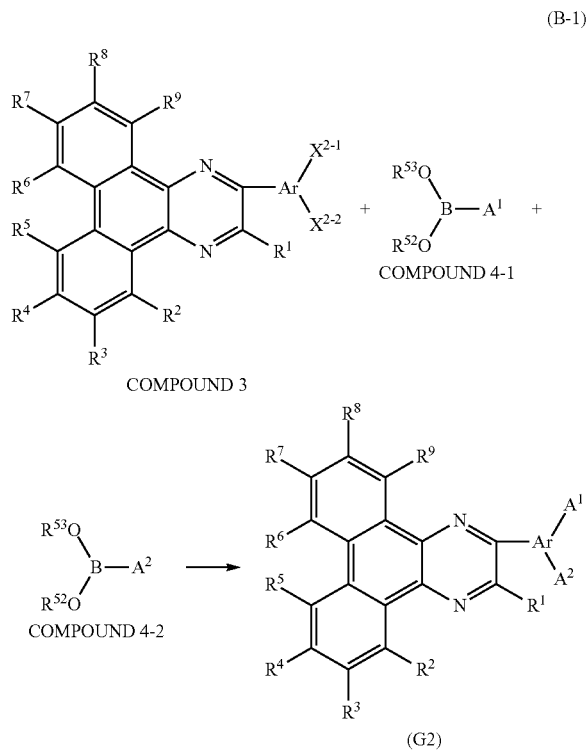

As shown in the synthesis scheme (B-1), a dihalide of a dibenzo[f,h]quinoxaline derivative (Compound 3) is coupled with an organoboron compound or boronic acid of a carbazole derivative, a dibenzofuran derivative, or a dibenzothiophene derivative (Compound 4-1 and Compound 4-2) by a Suzuki-Miyaura reaction, whereby the heterocyclic compound (G2) described in this embodiment can be obtained.

In the synthesis scheme (B-1), $A^1$ and $A^2$ each independently represent any of a substituted or unsubstituted carbazolyl group, a substituted or unsubstituted dibenzothiophenyl group, and a substituted or unsubstituted dibenzofuranyl group; Ar represents an aromatic hydrocarbon group having 6 to 13 carbon atoms; the aromatic hydrocarbon group may have a substituent; substituents of the aromatic hydrocarbon group may be bonded to each other to form a ring; $R^1$ to $R^9$ each independently represent any of hydrogen, an alkyl group having 1 to 4 carbon atoms, and a substituted or unsubstituted aryl group having 6 to 13 carbon atoms; $R^{52}$ and $R^{53}$ each independently represent hydrogen or an alkyl group having 1 to 6 carbon atoms; $R^{52}$ and $R^{53}$ may be bonded to each other to form a ring; $X^{2-1}$ and $X^{2-2}$ each independently represent a halogen or a triflate group; and the halogen is preferably iodine or bromine.

Examples of the palladium catalyst that can be used in the synthesis scheme (B-1) include, but are not limited to, palladium(II)acetate, tetrakis(triphenylphosphine)palladium(0), and bis(triphenylphosphine)palladium(II)dichloride.

Examples of the ligand of the palladium catalyst that can be used in the synthesis scheme (B-1) include, but are not limited to, tri(o-tolyl)phosphine, triphenylphosphine, and tricyclohexylphosphine.

Examples of the base that can be used in the synthesis scheme (B-1) include, but are not limited to, an organic base such as sodium tert-butoxide, inorganic bases such as potassium carbonate and sodium carbonate.

Examples of the solvent that can be used in the synthesis scheme (B-1) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of an ether such as ethylene glycol dimethyl ether and water. A mixed solvent of toluene and water; a mixed solvent of toluene, ethanol, and water; or a mixed solvent of ether such as ethylene glycol dimethyl ether and water is preferable.

As a coupling reaction shown in the synthesis scheme (B-1), the Suzuki-Miyaura Coupling Reaction using the organoboron compound or boronic acid represented by Compound 4 may be replaced with a cross coupling reaction using an organoaluminum compound, an organozirconium compound, an organozinc compound, an organotin compound, or the like. Note that the present invention is not limited thereto. In this coupling, a triflate group or the like may be used other than halogen; however, the present invention is not limited thereto.

In the reaction shown in the synthesis scheme (B-1), an organoboron compound or boronic acid of a dibenzo[f,h]quinoxaline derivative may be coupled with a halide of a carbazole derivative, a dibenzofuran derivative, or a dibenzothiophene derivative or with a carbazole derivative, a dibenzofuran derivative, or a dibenzothiophene derivative which has a triflate group as a substituent, by the Suzuki-Miyaura reaction.

Note that in the synthesis scheme (B-1), $X^{2-1}$ and $X^{2-2}$ may be different substituents, and Compound 4-1 and Compound 4-2 may be introduced one by one in two steps.

To synthesize the heterocyclic compound represented by the general formula (G2) in which A is a substituted or unsubstituted N-carbazolyl group, the following synthesis scheme (B-2) is employed, thereby obtaining the heterocyclic compound represented by the general formula (G3-1).

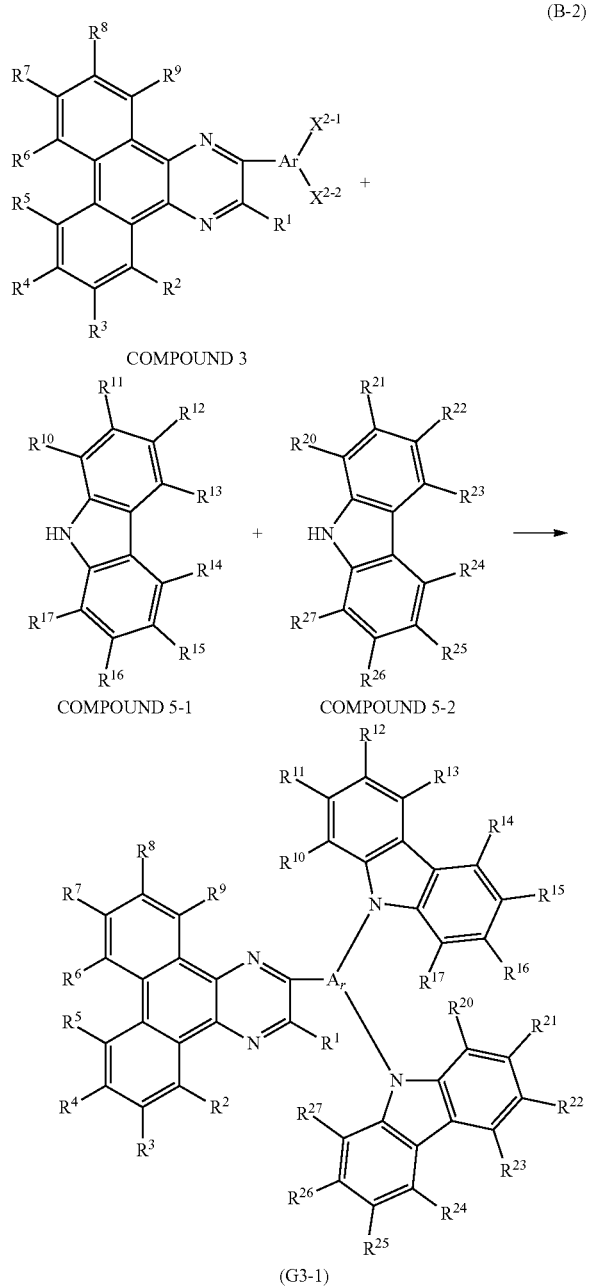

COMPOUND 3

COMPOUND 5-1    COMPOUND 5-2

(G3-1)

As shown in the synthesis scheme (B-2), a dihalide of a dibenzo[f,h]quinoxaline derivative (Compound 3) is coupled with a 9H-carbazole derivative (Compound 5-1 and Compound 5-2) using a metal catalyst, metal, or a metal compound in the presence of a base, whereby the heterocyclic compound (G3-1) described in this embodiment can be obtained.

In the synthesis scheme (B-2), $R^1$ to $R^9$ each independently represent any of hydrogen, an alkyl group having 1 to 4 carbon atoms, and a substituted or unsubstituted aryl group having 6 to 13 carbon atoms; Ar represents an aromatic hydrocarbon group having 6 to 13 carbon atoms; the aromatic hydrocarbon group may have a substituent; substituents of the aromatic hydrocarbon group may be bonded to each other to form a ring; $R^{10}$ to $R^{17}$ and $R^{20}$ to $R^{27}$ each independently represent any of hydrogen, an alkyl group having 1 to 4 carbon atoms, and a substituted or unsubstituted aryl group having 6 to 13 carbon atoms; $X^{3-1}$ and $X^{3-2}$ each independently represent a halogen or a triflate group; and the halogen is preferably iodine or bromine.

In the case where the Hartwig-Buchwald reaction is performed in the synthesis scheme (B-2), bis(dibenzylideneacetone)palladium(0), palladium(II)acetate, or the like is given as the palladium catalyst that can be used.

Examples of the ligand of the palladium catalyst that can be used in the synthesis scheme (B-2) include tri(tert-butyl)phosphine, tri(n-hexyl)phosphine, and tricyclohexylphosphine.

Examples of the base that can be used in the synthesis scheme (B-2) include an organic base such as sodium tert-butoxide and an inorganic base such as potassium carbonate.

Examples of the solvent that can be used in the synthesis scheme (B-2) include toluene, xylene, benzene, and tetrahydrofuran.

In order to synthesize the heterocyclic compound of this embodiment, the Ullmann reaction or the like may be employed instead of the Hartwig-Buchwald reaction, but the present invention is not limited to these.

Note that in the synthesis scheme (B-1), $X^{3-1}$ and $X^{3-2}$ may be different substituents, and Compound 5-1 and Compound 5-2 may be introduced one by one in two steps.

Thus, the heterocyclic compound of this embodiment can be synthesized.

The heterocyclic compound of this embodiment has a wide band gap. Accordingly, by the use of such a heterocyclic compound as a host material, in which a light-emitting substance is dispersed, of a light-emitting layer in a light-emitting element, the light-emitting element can have high current efficiency. In particular, the heterocyclic compound of this embodiment is suitably used as a host material in which a phosphorescent compound is dispersed. Further, since the heterocyclic compound of this embodiment has a high electron-transport property, it can be suitably used as a material for an electron-transport layer in a light-emitting element. By the use of the heterocyclic compound of this embodiment, a light-emitting element having low driving voltage can be achieved. A light-emitting element having high current efficiency can be achieved. A light-emitting element having a long lifetime can be achieved. Furthermore, by the use of this light-emitting element, a light-emitting device, an electronic device, and a lighting device each having reduced power consumption can be obtained.

Embodiment 2

In this embodiment, a light-emitting element of one embodiment of the present invention is described with reference to FIGS. 1A and 1B.

Accordingly, one embodiment of the present invention is a light-emitting element including a compound comprising a dibenzo[f,h]quinoxaline ring and two hole-transport skeletons, where the dibenzo[f,h]quinoxaline ring and the two hole-transport skeletons are bonded to an aromatic hydrocarbon group.

A compound with a quinoxaline skeleton has a high electron-transport property, and use of such a compound for a light-emitting element enables the element to have low driving voltage. However, a quinoxaline skeleton has a planar structure. Since a compound having a planar structure is easily crystallized when formed into a film, use of such a compound for a light-emitting element causes the element to have a short lifetime. Furthermore, a quinoxaline skeleton is poor at accepting holes. When a compound that cannot easily accept holes is used as a host material of a light-emitting layer, the region of electron-hole recombination concentrates on an interface on the anode side of the light-emitting layer, leading to a reduction in the lifetime of the light-emitting element. It is likely that these problems will be solved by introduction of a hole-transport skeleton into the molecule. However, if a hole-transport skeleton is directly bonded to a quinoxaline skeleton, the conjugated system extends to cause a decrease in band gap and a decrease in triplet excitation energy.

Nevertheless, the present inventors have found that the above problems can be solved by using, for a light-emitting element, a compound comprising a dibenzo[f,h]quinoxaline ring and two hole-transport skeletons, where the dibenzo[f,h]quinoxaline ring and the two hole-transport skeletons are bonded to an aromatic hydrocarbon group.

The compound includes two hole-transport skeletons in addition to a dibenzo[f,h]quinoxaline ring, making it easy to accept holes. Accordingly, by use of the compound as a host material of a light-emitting layer, electrons and holes recombine in the light-emitting layer, so that the reduction in the lifetime of the light-emitting element, which is caused by concentration on the interface on the anode side in the light-emitting region, can be prevented. Furthermore, the introduction of two hole-transport skeletons enables the compound to have a sterically bulky structure, and the compound is difficult to crystallize when formed into a film. By the use of the compound for a light-emitting element, the element can have a long lifetime. Moreover, in this compound, since an aromatic hydrocarbon group exists between a dibenzo[f,h]quinoxaline ring and two hole-transport skeletons, the decrease in band gap and the decrease in triplet excitation energy can be prevented as compared with a compound in which a dibenzo[f,h]quinoxaline ring and a hole-transport skeleton are directly bonded. By the use of the compound for a light-emitting element, the element can have high current efficiency.

Thus, the compound described above can be suitably used as a material for an organic device such as a light-emitting element or an organic transistor.

Note that the aromatic hydrocarbon group to which two hole-transport skeletons are bonded is preferably bonded to the 2-position of the dibenzo[f,h]quinoxaline ring.

As the hole-transport skeleton, a π-electron rich heteroaromatic ring is preferable. As the π-electron rich heteroaromatic ring, a carbazole ring, a dibenzofuran ring, or a dibenzothiophene ring is preferable. As the aromatic hydrocarbon group, any of a substituted or unsubstituted benzene skeleton and a substituted or unsubstituted biphenyl skeleton is preferable.

The heterocyclic compound described in Embodiment 1 is also an example of the compound comprising a dibenzo[f,h]quinoxaline ring and two hole-transport skeletons, where the dibenzo[f,h]quinoxaline ring and the two hole-transport skeletons are bonded to an aromatic hydrocarbon group.

Next, a light-emitting element of this embodiment is described in detail with reference to FIGS. 1A and 1B. The light-emitting element of this embodiment includes a plurality of layers between a pair of electrodes. In this embodiment, the light-emitting element includes a first electrode 101, a second electrode 102, and an EL layer 103 provided between the first electrode 101 and the second electrode 102. Note that in this embodiment, the first electrode 101 functions as an anode and the second electrode 102 functions as a cathode. In other words, when a voltage is applied between the first electrode 101 and the second electrode 102 so that the voltage of the first electrode 101 is higher than that of the second electrode 102, light emission can be obtained.

A substrate is used as a support of the light-emitting element. As the substrate, glass, plastic or the like can be used, for example. Note that a material other than glass or plastic can be used as far as it can function as a support of the light-emitting element.

For the first electrode 101, any of metal, an alloy, an electrically conductive compound, which have a high work function (specifically, a work function of 4.0 eV or more), and a mixture thereof or the like is preferably used. Specifically, for example, indium oxide-tin oxide (ITO: indium tin oxide), indium oxide-tin oxide containing silicon or silicon oxide, indium oxide-zinc oxide, and indium oxide containing tungsten oxide and zinc oxide are given. Films of these electrically conductive metal oxides are usually formed by sputtering but may be formed by application of a sol-gel method or the like. For example, indium oxide-zinc oxide can be formed by a sputtering method using a target in which zinc oxide is added to indium oxide at 1 wt % to 20 wt %. Moreover, indium oxide containing tungsten oxide and zinc oxide can be formed by a sputtering method using a target in which tungsten oxide is added to indium oxide at 0.5 wt % to 5 wt % and zinc oxide is added to indium oxide at 0.1 wt % to 1 wt %. Besides, gold (Au), platinum (Pt), nickel (Ni), tungsten (W), chromium (Cr), molybdenum (Mo), iron (Fe), cobalt (Co), copper (Cu), palladium (Pd), nitrides of metal materials (e.g., titanium nitride), and the like are given. Furthermore, graphene may be used.

There is no particular limitation on a stacked structure of the EL layer 103. The EL layer 103 can be formed by combining a layer that contains a substance having a high electron-transport property, a layer that contains a substance having a high hole-transport property, a layer that contains a substance having a high electron-injection property, a layer that contains a substance having a high hole-injection property, a layer that contains a bipolar substance (a substance having a high electron-transport property and a hole-transport property), and the like as appropriate. For example, the EL layer 103 can be formed by combining a hole-injection layer, a hole-transport layer, a light-emitting layer, an electron-transport layer, an electron-injection layer, and the like as appropriate. In this embodiment, a structure in which the EL layer 103 includes a hole-injection layer 111, a hole-transport layer 112, a light-emitting layer 113, an electron-transport layer 114, and an electron-injection layer 115 stacked in this order from the first electrode 101 functioning as an anode is described. Note that in the case where the second electrode 102 is an electrode functioning as an anode, in a layer containing an organic compound having a structure similar to the above, the hole-injection layer 111, the hole-transport layer 112, the light-emitting layer 113, the electron-transport layer 114, and the electron-injection layer 115 are stacked in this order from the second electrode 102. Materials included in the layers are specifically given below.

The hole-injection layer 111 is a layer containing a substance having a high hole-injection property. Molybdenum oxide, vanadium oxide, ruthenium oxide, tungsten oxide, manganese oxide, or the like can be used. Alternatively, the hole-injection layer 111 can be formed with a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis[4-[bis(3-methylphenyl)amino]phenyl]-N,N'-diphenyl-[1,1'-biphenyl]-4,4'-diamine (abbreviation: DNTPD), a high molecule such as poly(ethylenedioxythiophene)/poly(styrenesulfonic acid) (PEDOT/PSS), or the like.

Alternatively, a composite material in which a substance having a high hole-transport property contains an acceptor substance can be used for the hole-injection layer 111. In this specification, the composite material refers to not a material in which two materials are simply mixed but a material in the state where charge transfer between the materials can be caused by a mixture of a plurality of materials. This charge transfer includes the charge transfer that is realized only when an electric field exists.

Note that the use of such a substance having a high hole-transport property which contains an acceptor substance enables selection of a material for an electrode regardless of its work function. In other words, besides a material having a high work function, a material having a low work function can also be used for the first electrode 101.

As the substance having an acceptor property, 7,7,8,8-tetracyano-2,3,5,6-tetrafluoroquinodimethane (abbreviation: $F_4$-TCNQ), chloranil, and the like are given. In addition, transition metal oxides are given. Oxides of the metals that belong to Group 4 to Group 8 of the periodic table are given. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air and its hygroscopic property is low and is easily treated.

As the substance having a high hole-transport property used for the composite material, any of a variety of organic compounds such as aromatic amine compounds, carbazole compounds, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ cm$^2$/Vs or more is preferably used. Further, other than these substances, any substance that has a property of transporting more holes than electrons may be used. Organic compounds that can be used as the substance having a high hole-transport property in the composite material are specifically given below.

Examples of the aromatic amine compounds include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis[4-[bis(3-methylphenyl)amino]phenyl]-N,N'-diphenyl-[1,1'-biphenyl]-4,4'-diamine (abbreviation: DNTPD), and 1,3,5-tris[N-(4-diphenylaminophenyl)-N-phenylamino]benzene (abbreviation: DPA3B).

Examples of the carbazole compounds that can be used for the composite material specifically include 3-[N-(9-phenyl-carbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Examples of the carbazole compounds that can be used for the composite material also include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Examples of the aromatic hydrocarbons that can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, or the like can also be used. Thus, an aromatic hydrocarbon having 14 to 42 carbon atoms and having a hole mobility of $1 \times 10^{-6}$ cm$^2$/Vs or more is preferably used.

Note that the aromatic hydrocarbons that can be used for the composite material may have a vinyl skeleton. Examples of the aromatic hydrocarbons having a vinyl group include 4,4'-bis(2,2-diphenylvinyl)biphenyl (abbreviation: DPVBi), and 9,10-bis[4-(2,2-diphenylvinyl)phenyl]anthracene (abbreviation: DPVPA).

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis(4-butylphenyl)-N,N'-bis(phenyl)benzidine] (abbreviation: poly-TPD) can also be used.

The hole-transport layer 112 is a layer that contains a substance having a high hole-transport property. As the substance having a high hole-transport property, the substances given as the substances having a high hole-transport property which can be used for the above composite material can also be used. Note that a detailed explanation is omitted to avoid repetition. Refer to the explanation of the composite material.

The light-emitting layer 113 is a layer containing a light-emitting substance. The light-emitting layer 113 may be formed with a film containing only a light-emitting substance or a film in which an emission center substance is dispersed into a host material.

There is no particular limitation on a material that can be used as the light-emitting substance or the emission center substance in the light-emitting layer 113, and light emitted from the material may be either fluorescence or phosphorescence. Examples of the above light-emitting substance or emission center substance include the following substances: fluorescent substances such as N,N'-bis[4-(9-phenyl-9H-fluoren-9-yl)phenyl]-N,N'-diphenyl-pyrene-1,6-diamine (abbreviation: 1,6-FLPAPrn), N,N'-bis[4-(9H-carbazol-9-yl) phenyl]-N,N'-diphenylstilbene-4,4'-diamine (abbreviation: YGA2S), 4-(9H-carbazol-9-yl)-4'-(10-phenyl-9-anthryl) triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl) phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM); and phosphorescent substances such as bis[2-(3',5'-bistrifluoromethylphenyl)pyridinato-N,$C^{2'}$]iridium(III) picolinate (abbreviation: Ir($CF_3$ppy)$_2$(pic)), bis[2-(4',6'-difluorophenyl)pyridinato-N,$C^{2'}$]iridium(III) acetylacetonate (abbreviation: FIracac), tris(2-phenylpyridinato-N,$C^{2'}$)iridium(III) (abbreviation: Ir(ppy)$_3$), bis(2-phenylpyridinato-N,$C^{2'}$)iridium(III) acetylacetonate (abbreviation: Ir(ppy)$_2$acac), bis(1,2-diphenyl-1H-benzimidazolato)iridium(III) acetylacetonate (abbreviation: Ir(pbi)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), bis(2,4-diphenyl-1,3-oxazolato-N,$C^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,$C^{2'}$)iridium(III) acetylacetonate (abbreviation: Ir(bt)$_2$(acac)), (acetylacetonato)bis[2,3-bis(4-fluorophenyl)-5-methylpyrazinato]iridium(III) (abbreviation: Ir(Fdppr-Me)$_2$(acac)), (acetylacetonato)bis[2-(4-methoxyphenyl)-3,5-dimethylpyrazinato]iridium(III) (abbreviation: Ir(dmmoppr)$_2$(acac)), tris(2-phenylquinolinato-N,$C^{2'}$)iridium(III) (abbreviation: Ir(pq)$_3$), bis(2-phenylquinolinato-N,$C^{2'}$)iridium(III) (acetylacetonate) (abbreviation: Ir(pq)$_2$(acac)), (acetylacetonato)bis(3,5-dimethyl-2-phenylpyrazinato)iridium(III) (abbreviation: Ir(mppr-Me)$_2$(acac)), (acetylacetonato)bis(5-isopropyl-3-methyl-2-phenylpyrazinato)iridium(III) (abbreviation: Ir(mppr-iPr)$_2$(acac)), bis[2-(2'-benzo[4,5-α]thienyl)pyridinato-N,$C^{3'}$]iridium(III)(acetylacetonate) (abbreviation: Ir(btp)$_2$(acac)), bis(1-phenylisoquinolinato-N,$C^{2'}$)iridium(III) acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphine platinum(II) (abbreviation: PtOEP), tris(acetylacetonato)(monophenanthroline)terbium(III) (abbreviation: [Tb(acac)$_3$(Phen)]), tris(1,3-diphenyl-1,3-propanedionato)(monophenanthroline)europium(III) (abbreviation: [Eu(DBM)$_3$(Phen)]), and tris[1-(2-thenyl)-3,3,3-trifluoroacetonato](monophenanthroline)europium(III) (abbreviation: [Eu(TTA)$_3$(Phen)]). Note that the carbazole compounds according to the present invention, typical examples of which include the carbazole compound represented by the general formula (G1) described in Embodiment 1, emit light in the blue to ultraviolet region, and therefore can also be used as an emission center substance. Note that the heterocyclic compound described in Embodiment 1 can be also used as an emission center material.

The compound comprising a dibenzo[f,h]quinoxaline ring and two hole-transport skeletons, where the dibenzo[f,h]quinoxaline ring and the two hole-transport skeletons are bonded to an aromatic hydrocarbon group can be suitably used as a host material in which the emission center substance is dispersed. The compound may be used as a material for a carrier-transport layer that is adjacent to the light-emitting layer. Note that in the case where the compound is used as a host material, the emission center material is preferably a substance having a smaller band gap than the carbazole compound when the emission center material is a fluorescent light-emitting material, and the emission center material is preferably a substance having a smaller triplet triplet excitation energy than the carbazole compound when the emission center material is a phosphorescent light-emitting material; however, the material is not limited thereto.

The above-described compound has two hole-transport skeletons in addition to a dibenzo[f,h]quinoxaline ring, making it easy to accept holes. Accordingly, by use of the compound as a host material of a light-emitting layer, electrons and holes recombine in the light-emitting layer, so that it is possible to suppress the decrease in the lifetime of the light-emitting element. Furthermore, the introduction of two hole-transport skeletons enables the compound to have a sterically bulky structure, and the compound is difficult to crystallize when formed into a film. By the use of the compound for a light-emitting element, the element can have a long lifetime. Moreover, in this compound, since an aromatic hydrocarbon group exists between a dibenzo[f,h]quinoxaline ring and two hole-transport skeletons, decreases in band gap and triplet excitation energy can be prevented as compared with a compound in which a dibenzo[f,h]quinoxaline ring and a hole-transport skeleton are directly bonded. By the use of the compound for a light-emitting element, the element can have high current efficiency.

A compound in which an aryl group to which two hole-transport skeletons are bonded is bonded to a dibenzo[f,h]quinoxaline ring is considered as a skeleton where the LUMO level is predominantly located. Further, the compound has a deep LUMO level of at least −2.8 eV or less, specifically −2.9 eV or less on the basis of cyclic voltammetry (CV) measurements. For example, the LUMO level of 2mDBTPDBq-II is found to be −2.96 eV by CV measurements. Furthermore, the LUMO level of a phosphorescent compound having a diazine skeleton, which is typified by the above-described phosphorescent compound having a pyrazine skeleton, such as [Ir(mppr-Me)$_2$(acac)], [Ir(mppr-iPr)$_2$(acac)], [Ir(tppr)$_2$(acac)], or [Ir(tppr)$_2$(dpm)] or the above-described phosphorescent compound having a pyrimidine skeleton such as [Ir (tBuppm)$_2$(acac)] or [Ir(dppm)$_2$(acac)], is substantially as deep as the LUMO level of the compound in which an aryl group to which two hole-transport skeletons are bonded is bonded to a dibenzo[f,h]quinoxaline ring. Therefore, when a light-emitting layer includes a compound of one embodiment of the present invention as a host material, and a phosphorescent compound having a diazine skeleton (especially, a pyrazine skeleton or a pyrimidine skeleton) as a guest material, a light-emitting element in which traps for electrons in the light-emitting layer can be reduced to a minimum and driving voltage is extremely low can be realized.

When the compound comprising a dibenzo[f,h]quinoxaline ring and two hole-transport skeletons, where the dibenzo[f,h]quinoxaline ring and the two hole-transport skeletons are bonded to an aromatic hydrocarbon group is not used as the above host material, any of the following substances can be used for the host material: metal complex such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(II) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[g,p]chrysene derivatives are given, and specific examples are 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N",N",N'",N'"-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), and the like. Other than these, known materials can be used.

Note that the light-emitting layer 113 can also be a stack of two or more layers. For example, in the case where the light-emitting layer 113 is formed by stacking a first light-emitting layer and a second light-emitting layer in that order over the hole-transport layer, for example, a substance having a hole-transport property is used for the host material of the first light-emitting layer and a substance having an electron-transport property is used for the host material of the second light-emitting layer.

In the case where the light-emitting layer having the above-described structure includes a plurality of materials, co-evaporation by a vacuum evaporation method can be used, or alternatively an inkjet method, a spin coating method, a dip coating method, or the like with a solution of the materials can be used.

The electron-transport layer 114 is a layer containing a substance having a high electron-transport property: for example, a layer containing a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq). Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here mainly have an electron mobility of $10^{-6}$ cm$^2$/Vs or more. Note that other than these substances, any substance that has a property of transporting more electrons than holes may be used.

The compound comprising a dibenzo[f,h]quinoxaline ring and two hole-transport skeletons, where the dibenzo[f,h]quinoxaline ring and the two hole-transport skeletons are bonded to an aromatic hydrocarbon group has an excellent electron-transport property, and can be suitably used as a material for the electron-transport layer 114. The introduction of two hole-transport skeletons enables the compound to have a bulky structure, and the compound is difficult to crystallize when formed into a film. By the use of the compound for a light-emitting element, the element can have a long lifetime. Moreover, in this compound, since an aromatic hydrocarbon group exists between a dibenzo[f,h]quinoxaline ring and two hole-transport skeletons, decreases in band gap and triplet excitation energy can be prevented as compared with a compound in which a dibenzo[f,h]quinoxaline ring and a hole-transport skeleton are directly bonded. By the use of the compound for a light-emitting element, the element can have high current efficiency.

Furthermore, the electron-transport layer 114 is not limited to a single layer and may be a stack of two or more layers containing any of the above substances.

Between the electron-transport layer 114 and the light-emitting layer 113, a layer that controls transport of electron carriers may be provided. This is a layer formed by addition of a small amount of a substance having a high electron-trapping property to a material having a high electron-transport property as described above, and capable of adjusting carrier balance by suppressing transport of electron carriers. Such a structure is very effective in preventing a problem (such as a reduction in element lifetime) caused when electrons pass through the light-emitting layer.

In addition, an electron-injection layer may be provided in contact with the second electrode 102 between the electron-transport layer 114 and the second electrode 102. For the electron-injection layer, an alkali metal, an alkaline earth metal, or a compound thereof such as lithium fluoride (LiF), cesium fluoride (CsF), or calcium fluoride ($CaF_2$) can be used. For example, a layer that is formed with a substance having an electron-transport property and contains an alkali metal, an alkaline earth metal, magnesium (Mg), or a compound thereof, such as an Alq layer containing magnesium (Mg), can be used. Note that electron injection from the second electrode 102 is efficiently performed by the use of a layer that is formed with a substance having an electron-transport property and contains an alkali metal or an alkaline earth metal as the electron-injection layer, which is preferable.

For the second electrode 102, any of metals, alloys, electrically conductive compounds, and mixtures thereof which have a low work function (specifically, a work function of 3.8 eV or less) or the like can be used. Specific examples of such a cathode material include elements that belong to Groups 1 and 2 in the periodic table, i.e., alkali metals such as lithium (Li) and cesium (Cs), alkaline earth metals such as calcium (Ca) and strontium (Sr), magnesium (Mg), alloys thereof (e.g., MgAg or AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these electrically conductive materials can be formed by a sputtering method, an inkjet method, a spin coating method, or the like.

Further, any of a variety of methods can be used to form the EL layer 103 regardless whether it is a dry process or a wet process. For example, a vacuum evaporation method, an inkjet method, a spin coating method or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

In the light-emitting element having the above-described structure, a current flows due to a potential difference between the first electrode 101 and the second electrode 102, and a hole and an electron recombine in the light-emitting layer 113 which contains a substance having a high light-emitting property, so that light is emitted. That is, a light-emitting region is formed in the light-emitting layer 113.

Light emission is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light emission is extracted from the substrate side through the first electrode 101. In the case where only the second electrode 102 is a light-transmitting electrode, light emission is extracted from the side opposite to the substrate side through the second electrode 102. In the case where each of the first electrode 101 and the second electrode 102 is a light-transmitting electrode, light emission is extracted from both the substrate side and the side opposite to the substrate through the first electrode 101 and the second electrode 102.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented. The order of stacking the layers is not limited to the above structure and may be the following order obtained by reversing the order shown in FIG. 1A: the second electrode, the electron-injection layer, the electron-transport layer, the light-emitting layer, the hole-transport layer, the hole-injection layer, and the first electrode from the substrate side.

Further, in order that transfer of energy from an exciton generated in the light-emitting layer is prevented, it is preferable that the hole-transport layer 112 and the electron-transport layer 114 which are directly in contact with the light-emitting layer, particularly a carrier-transport layer in contact with a side closer to the light-emitting region in the light-emitting layer 113 be formed with a substance having a larger energy gap than the light-emitting substance of the light-emitting layer or the emission center substance included in the light-emitting layer.

Any layer of the light-emitting element of this embodiment includes a compound comprising a dibenzo[f,h]quinoxaline ring and two hole-transport skeletons, where the dibenzo[f,h]quinoxaline ring and the two hole-transport skeletons are bonded to an aromatic hydrocarbon group. The compound has two hole-transport skeletons in addition to a dibenzo[f,h]quinoxaline ring, making it easy to accept holes. Accordingly, by use of the compound as a host material of a light-emitting layer, electrons and holes recombine in the light-emitting layer, so that the decrease in the lifetime of the light-emitting element can be prevented. Furthermore, the introduction of two hole-transport skeletons enables the compound to have a sterically bulky structure, and the compound is difficult to crystallize when formed into a film. By the use of the compound for a host material or an electron-transport material in the light-emitting layer, the element can have a long lifetime. Moreover, in this compound, since an aromatic hydrocarbon group exists between a dibenzo[f,h]quinoxaline ring and two hole-transport skeletons, decreases in band gap and triplet excitation energy can be prevented as compared with a compound in which a dibenzo[f,h]quinoxaline ring and a hole-transport skeleton are directly bonded. By the use of the compound for a host material or an electron-transport material in the light-emitting layer, the element can have high current efficiency.

In this embodiment, the light-emitting element is formed over a substrate formed of glass, plastic, or the like. With a plurality of such light-emitting elements over one substrate, a passive matrix light-emitting device can be fabricated. In addition, a light-emitting element may be formed over an electrode electrically connected to a thin film transistor (TFT) which is formed over a substrate formed of glass, plastic, or the like; thus, an active matrix light-emitting device in which the TFT controls the drive of the light-emitting element can be fabricated. Note that there is no particular limitation on the structure of the TFT, which may be a staggered TFT or an inverted staggered TFT. In addition, crystallinity of a semiconductor used for the TFT is not particularly limited either;

an amorphous semiconductor or a crystalline semiconductor may be used. In addition, a driver circuit formed in a TFT substrate may be formed with an n-type TFT and a p-type TFT, or with either an n-type TFT or a p-type TFT.

Embodiment 3

In this embodiment, one mode of a light-emitting element (hereinafter, also referred to as a stacked-type element) having a structure in which a plurality of light-emitting units is stacked is described with reference to FIG. 1B. This light-emitting element is a light-emitting element including a plurality of light-emitting units between a first electrode and a second electrode. Each light-emitting unit can have the same structure as the EL layer 103 described in Embodiment 2. In other words, it can be said that the light-emitting element described in Embodiment 2 is a light-emitting element having one light-emitting unit and the light-emitting element of this embodiment is a light-emitting element having a plurality of light-emitting units.

Figure 1B:
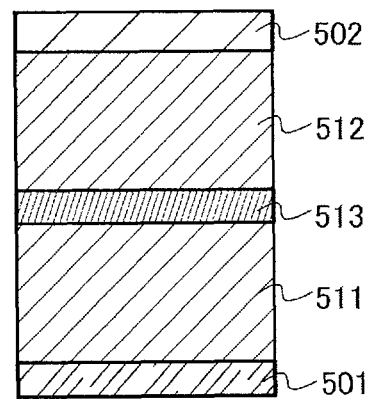

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond, respectively, to the first electrode 101 and the second electrode 102 according to Embodiment 2, and materials described in Embodiment 2 can be used. Further, the structures of the first light-emitting unit 511 and the second light-emitting unit 512 may be the same or different.

The charge generation layer 513 contains a composite material of an organic compound and a metal oxide. This composite material of an organic compound and a metal oxide is the composite material described in Embodiment 2, and contains an organic compound and a metal oxide such as vanadium oxide, molybdenum oxide, or tungsten oxide. As the organic compound, any of a variety of compounds such as aromatic amine compounds, carbazole compounds, aromatic hydrocarbons, and high molecular compounds (oligomers, dendrimers, polymers, or the like) can be used. Note that as the organic compound, the one having a hole mobility of $10^{-6}$ $cm^2/Vs$ or more as an organic compound having a hole-transport property is preferably used. Further, other than these substances, any substance that has a property of transporting more holes than electrons may be used. Since a composite of an organic compound and a metal oxide is excellent in carrier-injection property and carrier-transport property, low voltage driving and low current driving can be realized.

The charge generation layer 513 may be formed in such a way that a layer containing the composite material of an organic compound and a metal oxide is combined with a layer containing another material, for example, with a layer that contains a compound selected from substances having an electron-donating property and a compound having a high electron-transport property. The charge generation layer 513 may be formed in such a way that a layer containing the composite material of an organic compound and a metal oxide is combined with a transparent conductive film.

The charge generation layer 513 interposed between the first light-emitting unit 511 and the second light-emitting unit 512 may have any structure as far as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as far as the layer injects electrons into the first light-emitting unit 511 and holes into the second light-emitting unit 512 when a voltage is applied such that the voltage of the first electrode is higher than that of the second electrode.

Although the light-emitting element having two light-emitting units is described in this embodiment, the present invention can be similarly applied to a light-emitting element in which three or more light-emitting units are stacked. By arrangement of a plurality of light-emitting units, which are partitioned by the charge-generation layer between a pair of electrodes, as in the light-emitting element of this embodiment, light emission in a high luminance region can be realized with current density kept low, thus a light-emitting element having a long lifetime can be realized. Further, in application to lighting devices, since a voltage drop due to resistance of an electrode material can be reduced, light emission in a large area is possible. Moreover, a light-emitting device having low driving voltage and having lower power consumption can be realized.

By making emission colors of the light-emitting units different from each other, light emission with a desired color can be obtained from the light-emitting element as a whole. For example, in a light-emitting element including two light-emitting units, the emission colors of the first light-emitting unit and the second light-emitting unit are made complementary, so that the light-emitting element which emits white light as the whole element can be obtained. Note that the term "complementary" means color relationship in which an achromatic color is obtained when colors are mixed. That is, a mixture of light emissions with complementary colors gives white light emission. The same can be applied to a light-emitting element including three light-emitting units. For example, the light-emitting element as a whole can emit white light when the emission color of the first light-emitting unit is red, the emission color of the second light-emitting unit is green, and the emission color of the third light-emitting unit is blue.

Since the light-emitting element of this embodiment includes a compound comprising a dibenzo[f,h]quinoxaline ring and two hole-transport skeletons, where the dibenzo[f,h]quinoxaline ring and the two hole-transport skeletons are bonded to an aromatic hydrocarbon group, the light-emitting element can have high emission efficiency, a long lifetime, and/or low driving voltage.

Note that this embodiment can be combined with any of the other embodiments as appropriate.

Embodiment 4

In this embodiment, description is given of a light-emitting device in which a light-emitting element including a compound comprising a dibenzo[f,h]quinoxaline ring and two hole-transport skeletons, where the dibenzo[f,h]quinoxaline ring and the two hole-transport skeletons are bonded to an aromatic hydrocarbon group is used.

In this embodiment, an example of the light-emitting device fabricated using a light-emitting element including the compound comprising a dibenzo[f,h]quinoxaline ring and two hole-transport skeletons, where the dibenzo[f,h]quinoxaline ring and the two hole-transport skeletons are bonded to an aromatic hydrocarbon group is described with reference to FIGS. 2A and 2B. Note that FIG. 2A is a top view illustrating the light-emitting device and FIG. 2B is a cross-sectional view of FIG. 2A taken along lines A-B and C-D. This light-emitting device includes a driver circuit portion (source driver circuit) 601, a pixel portion 602, and a driver circuit portion (gate driver circuit) 603, which are to control light emission of the light-emitting element and illustrated with dotted lines. Moreover, a reference numeral 604 denotes a sealing substrate; 625, a desiccant; 605, a sealing material; and 607, a space surrounded by the sealing material 605.

Reference numeral 608 denotes a wiring for transmitting signals to be inputted into the source driver circuit 601 and the gate driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is described with reference to FIG. 2B. The driver circuit portion and the pixel portion are formed over an element substrate 610; the source driver circuit 601, which is a driver circuit portion, and one of the pixels in the pixel portion 602 are illustrated here.

As the source driver circuit 601, a CMOS circuit in which an n-channel TFT 623 and a p-channel TFT 624 are combined is formed. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit may not necessarily be formed over the substrate, and the driver circuit can be formed outside, not over the substrate.

The pixel portion 602 includes a plurality of pixels including a switching TFT 611, a current controlling TFT 612, and a first electrode 613 electrically connected to a drain of the current controlling TFT. Note that to cover an end portion of the first electrode 613, an insulator 614 is formed, for which a positive type photosensitive acrylic resin film is used here.

In order to improve coverage, the insulator 614 is formed to have a curved surface with curvature at its upper or lower end portion. For example, in the case where positive photosensitive acrylic is used for a material of the insulator 614, only the upper end portion of the insulator 614 preferably has a curved surface with a curvature radius (0.2 µm to 3 µm). As the insulator 614, either a negative type photosensitive resin or a positive type photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. Note that when the stacked structure is used, the first electrode 613 has low resistance as a wiring, forms a favorable ohmic contact, and can function as an anode.

In addition, the EL layer 616 containing an organic compound is formed by any of a variety of methods such as an evaporation method using a shadow mask, an inkjet method, and a spin coating method. The EL layer 616 includes the compound comprising a dibenzo[f,h]quinoxaline ring and two hole-transport skeletons, where the dibenzo[f,h]quinoxaline ring and the two hole-transport skeletons are bonded to an aromatic hydrocarbon group. Further, another material included in the EL layer 616 is not limited, and may be a low molecular compound or a high molecular compound (which may be an oligomer and a dendrimer).

Furthermore, a material having a small work function described in Embodiment 2 is preferably used as a material used for the second electrode 617 which is formed over the EL layer 616 and functions as a cathode. In the case where light generated in the EL layer 616 passes through the second electrode 617, the second electrode 617 is preferably a stack of a thin metal film and a transparent conductive film (such as ITO, indium oxide containing zinc oxide at 2 wt % to 20 wt %, indium tin oxide containing silicon, or zinc oxide (ZnO)).

Note that the light-emitting element is formed with the first electrode 613, the EL layer 616, and the second electrode 617. The light-emitting element has any of the structures described in Embodiment 2 or 3. In the light-emitting device of this embodiment, the pixel portion, which includes a plurality of light-emitting elements, may include both the light-emitting element with any of the structures described in Embodiments 2 and 3 and a light-emitting element with a structure other than those.

Further, the sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with filler, and may be filled with an inert gas (such as nitrogen or argon), or the sealing material 605.

Note that an epoxy-based resin is preferably used for the sealing material 605. It is desirable that such a material do not transmit moisture or oxygen as much as possible. As a material for the sealing substrate 604, a plastic substrate formed of FRP (fiberglass-reinforced plastics), PVF (polyvinyl fluoride), polyester, acrylic, or the like can be used besides a glass substrate or a quartz substrate.

As described above, the light-emitting device fabricated using the light-emitting element including the compound comprising a dibenzo[f,h]quinoxaline ring and two hole-transport skeletons, where the dibenzo[f,h]quinoxaline ring and the two hole-transport skeletons are bonded to an aromatic hydrocarbon group can be obtained.

The light-emitting element including the compound comprising a dibenzo[f,h]quinoxaline ring and two hole-transport skeletons, where the dibenzo[f,h]quinoxaline ring and the two hole-transport skeletons are bonded to an aromatic hydrocarbon group is used in the light-emitting device of this embodiment, and thus the light-emitting device can have favorable characteristics. Specifically, in the compound comprising a dibenzo[f,h]quinoxaline ring and two hole-transport skeletons, where the dibenzo[f,h]quinoxaline ring and the two hole-transport skeletons are bonded to an aromatic hydrocarbon group, a decrease in band gap and triplet excitation energy is prevented; accordingly, energy transfer from a light-emitting substance to a host material or a transport layer can be prevented. Therefore, a light-emitting element having high emission efficiency can be provided, so that a light-emitting device having reduced power consumption can be provided. In addition, a light-emitting element having low driving voltage can be provided, so that a light-emitting device having low driving voltage can be provided. Furthermore, a light-emitting element having a long lifetime can be provided, so that a highly reliable light-emitting device can be provided.

Figure 3A:
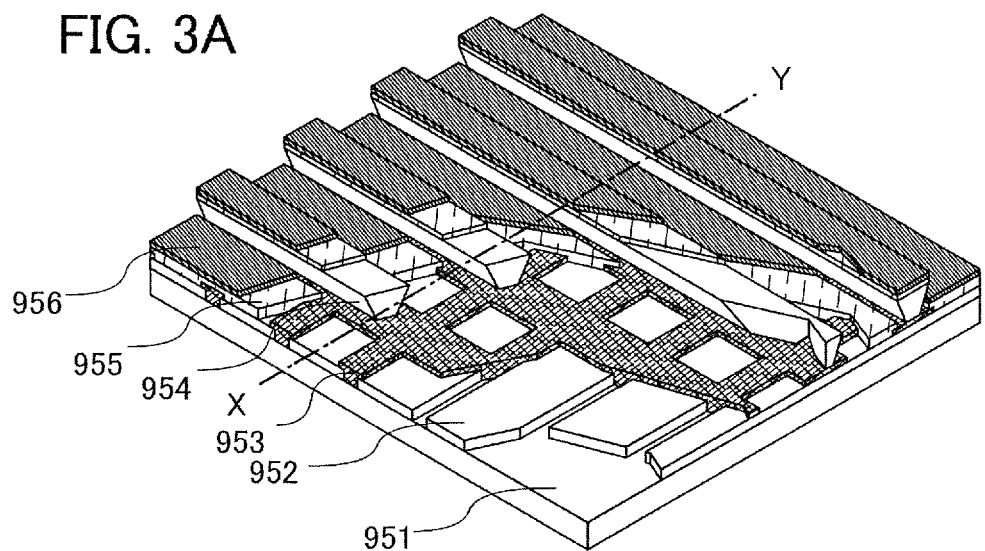
FIGS. 3A and 3B illustrate a light-emitting device according to one embodiment of the present invention.
Figure 3B:
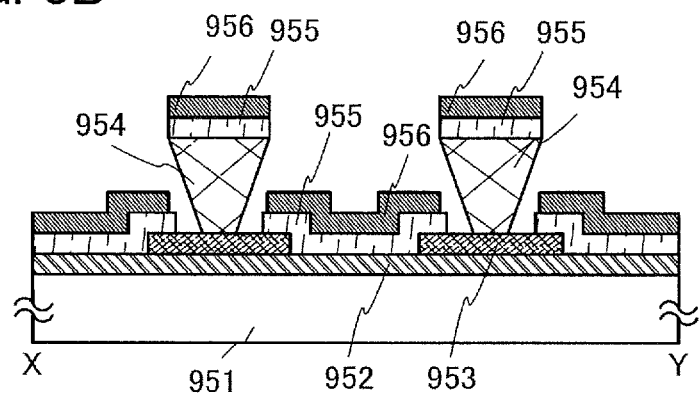

Although an active matrix light-emitting device is thus described above, a passive matrix light-emitting device is described below. FIGS. 3A and 3B illustrate a passive matrix light-emitting device fabricated according to the present invention. FIG. 3A is a perspective view of the light-emitting device, and FIG. 3B is a cross-sectional view taken along line X-Y in FIG. 3A. In FIGS. 3A and 3B, over a substrate 951, an EL layer 955 is provided between an electrode 952 and an electrode 956. An end portion of the electrode 952 is covered with an insulating layer 953. In addition, a partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). The partition layer 954 thus provided can prevent a defect in the light-emitting element due to static charge or the like. The passive matrix light-emitting device can also be driven with low power consumption by including the light-emitting element described in Embodiment 2 or 3 capable of operating at low voltage. In addition, the light-emitting device can be driven with low power consumption by including the light-emitting element described in Embodiment 2 or 3 having high emission efficiency. Furthermore, the light-emitting device having high reliability can be provided by including the light-emitting element described in Embodiment 2 or 3 having a long lifetime.

Since many minute light-emitting elements arranged in a matrix in the light-emitting device described above can each be controlled, the light-emitting device can be suitably used as a display device for displaying images.

Embodiment 5

In this embodiment, electronic devices each including, as a part thereof, the light-emitting element described in Embodiment 2 or 3. The light-emitting element described in Embodiment 2 or 3 is a light-emitting element having reduced power consumption because an EL layer thereof includes a compound comprising a dibenzo[f,h]quinoxaline ring and two hole-transport skeletons, where the dibenzo[f,h]quinoxaline ring and the two hole-transport skeletons are bonded to an aromatic hydrocarbon group. Therefore, the electronic devices of this embodiment can have a light-emitting portion or display portion having reduced power consumption. In addition, the electronic devices can be driven at a low driving voltage because the light-emitting element described in Embodiment 2 or 3 is a light-emitting element driven at a low driving voltage. The light-emitting element described in Embodiment 2 or 3 is also a light-emitting element having a long lifetime, whereby an electronic device having high reliability can be achieved.

Examples of the electronic devices to which the above light-emitting element is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices are described below.

Figure 4A:
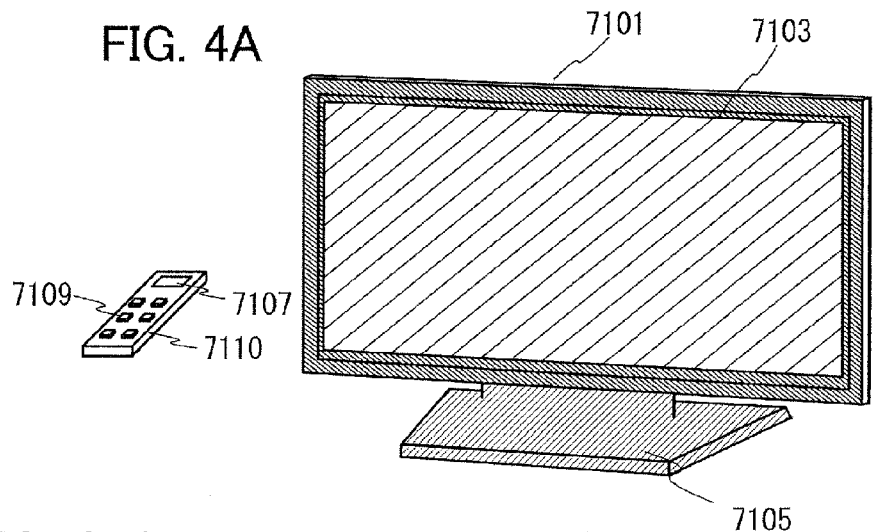
Figure 4A:
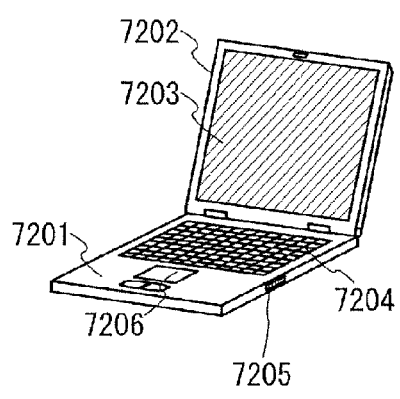
Figure 4A:
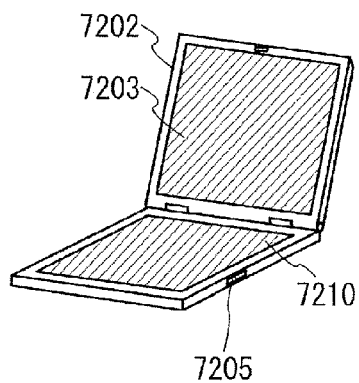

FIG. 4A illustrates an example of a television device. In the television device, a display portion 7103 is incorporated in a housing 7101. In addition, here, the housing 7101 is supported by a stand 7105. The display portion 7103 enables display of images and includes light-emitting elements which are the same as that described in Embodiment 2 or 3 and arranged in a matrix. Since each light-emitting element includes a compound comprising a dibenzo[f,h]quinoxaline ring and two hole-transport skeletons, where the dibenzo[f,h]quinoxaline ring and the two hole-transport skeletons are bonded to an aromatic hydrocarbon group, the light-emitting elements can be light-emitting elements having high emission efficiency, low driving voltage, and a long lifetime. Accordingly, the television device that has the display portion 7103 including the light-emitting elements can be a television device having reduced power consumption, low driving voltage, and high reliability.

The television device can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the receiver, general television broadcasting can be received. Furthermore, when the television device is connected to a communication network by wired or wireless connection via the modem, one-way (from a transmitter to a receiver) or two-way (between a transmitter and a receiver, between receivers, or the like) data communication can be performed.

FIG. 4B1 illustrates a computer, which includes a main body 7201, a housing 7202, a display portion 7203, a keyboard 7204, an external connection port 7205, a pointing device 7206, and the like. Note that this computer is manufactured by using light-emitting elements arranged in a matrix in the display portion 7203, which are the same as that described in Embodiment 2 or 3. The computer illustrated in FIG. 4B1 may have a structure illustrated in FIG. 4B2. The computer illustrated in FIG. 4B2 is provided with a second display portion 7210 instead of the keyboard 7204 and the pointing device 7206. The second display portion 7210 is a touch screen, and input can be performed by operation of display for input on the second display portion 7210 with a finger or a dedicated pen. The second display portion 7210 can also display images other than the display for input. The display portion 7203 may be also a touch screen. Connecting the two screens with a hinge can prevent troubles; for example, the screens can be prevented from being cracked or broken while the computer is being stored or carried.

Since the light-emitting element in such a computer includes a compound comprising a dibenzo[f,h]quinoxaline ring and two hole-transport skeletons, where the dibenzo[f,h]quinoxaline ring and the two hole-transport skeletons are bonded to an aromatic hydrocarbon group, the light-emitting elements can be light-emitting elements having high emission efficiency, low driving voltage, and a long lifetime. Accordingly, the computer that has the display portion 7203 including the light-emitting elements can have reduced power consumption, low driving voltage, and/or high reliability.

Figure 4C:
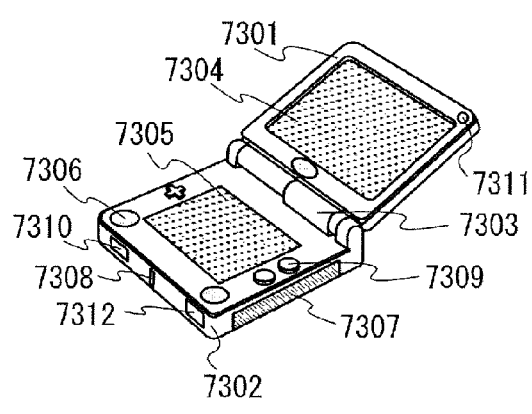

FIG. 4C illustrates a portable game machine having two housings, a housing 7301 and a housing 7302, which are connected with a joint portion 7303 so that the portable game machine can be opened or folded. A display portion 7304 including light-emitting elements which are the same as that described in Embodiment 2 or 3 and arranged in a matrix is incorporated in the housing 7301, and a display portion 7305 is incorporated in the housing 7302. In addition, the portable game machine illustrated in FIG. 4C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as far as the display portion including light-emitting elements which are the same as that described in Embodiment 2 or 3 and arranged in a matrix is used as at least either the display portion 7304 or the display portion 7305, or both, and the structure can include other accessories as appropriate. The portable game machine illustrated in FIG. 4C has a function of reading out a program or data stored in a storage medium to display it on the display portion, and a function of sharing information with another portable game machine by wireless communication. The portable game machine illustrated in FIG. 4C can have a variety of functions without limitation to the above. The light-emitting element used in the display portion 7304 can have high emission efficiency, low driving voltage, and/or a long lifetime by including the compound comprising a dibenzo[f,h]quinoxaline ring and two hole-transport skeletons, where the dibenzo[f,h]quinoxaline ring and the two hole-transport skeletons are bonded to an aromatic hydrocarbon group. The portable game machine including such a light-emitting element in the display portion 7304 can have reduced power consumption, low driving voltage, and/or high reliability.

Figure 4D:
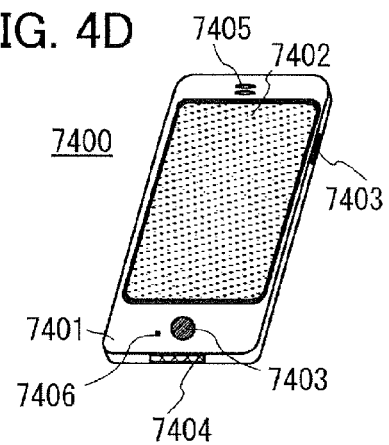

FIG. 4D illustrates an example of a cellular phone. The cellular phone is provided with operation buttons 7403, an external connection port 7404, a speaker 7405, a microphone 7406, and the like, in addition to a display portion 7402 incorporated in a housing 7401. Note that the cellular phone 7400 has the display portion 7402 including light-emitting elements which are the same as that described in Embodiment 2 or 3 and arranged in a matrix. Since each light-emitting element includes the compound comprising a dibenzo[f,h]quinoxaline ring and two hole-transport skeletons, where the dibenzo[f,h]quinoxaline ring and the two hole-transport skeletons are bonded to an aromatic hydrocarbon group, the light-emitting element can have high emission efficiency, low driving voltage, and/or a long lifetime. Accordingly, the cellular phone that has the display portion 7402 including the light-emitting elements can be a cellular phone having reduced power consumption, low driving voltage, and long lifetime.

When the display portion 7402 of the cellular phone illustrated in FIG. 4D is touched with a finger or the like, data can be input into the cellular phone. In this case, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a text input mode mainly for inputting text is selected for the display portion 7402 so that text displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone, display on the screen of the display portion 7402 can be automatically changed by determining the orientation of the cellular phone (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on the kinds of images displayed on the display portion 7402. For example, when a signal for an image displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, so that personal authentication can be performed. Furthermore, by use of a backlight or a sensing light source that emits a near-infrared light for the display portion, an image of a finger vein, a palm vein, or the like can also be taken.

Note that the structure described in this embodiment can be combined with any of the structures described in Embodiments 2 to 4 as appropriate. Furthermore, the heterocyclic compound described in Embodiment 1 shows part of a compound comprising a dibenzo[f,h]quinoxaline ring and two hole-transport skeletons, where the dibenzo[f,h]quinoxaline ring and the two hole-transport skeletons are bonded to an aromatic hydrocarbon group in detail.

As described above, the application range of the light-emitting device having the light-emitting element according to Embodiment 2 or 3 which includes any of the carbazole compounds described in Embodiment 1 is wide so that this light-emitting device can be applied to electronic devices in a variety of fields. By use of the compound comprising a dibenzo[f,h]quinoxaline ring and two hole-transport skeletons, where the dibenzo[f,h]quinoxaline ring and the two hole-transport skeletons are bonded to an aromatic hydrocarbon group, an electronic device having reduced power consumption, low driving voltage, and high reliability can be obtained.

The light-emitting element including a compound comprising a dibenzo[f,h]quinoxaline ring and two hole-transport skeletons, where the dibenzo[f,h]quinoxaline ring and the two hole-transport skeletons are bonded to an aromatic hydrocarbon group can also be used for a lighting device. One mode of application of the light-emitting element to a lighting device is described with reference to FIGS. 5 to 7. Note that the lighting device includes the light-emitting element as a light irradiation unit and at least includes an input-output terminal portion that supplies a current to the light-emitting element. Further, the light-emitting element is preferably shielded from the outside atmosphere (especially water) by sealing.

Figure 5:
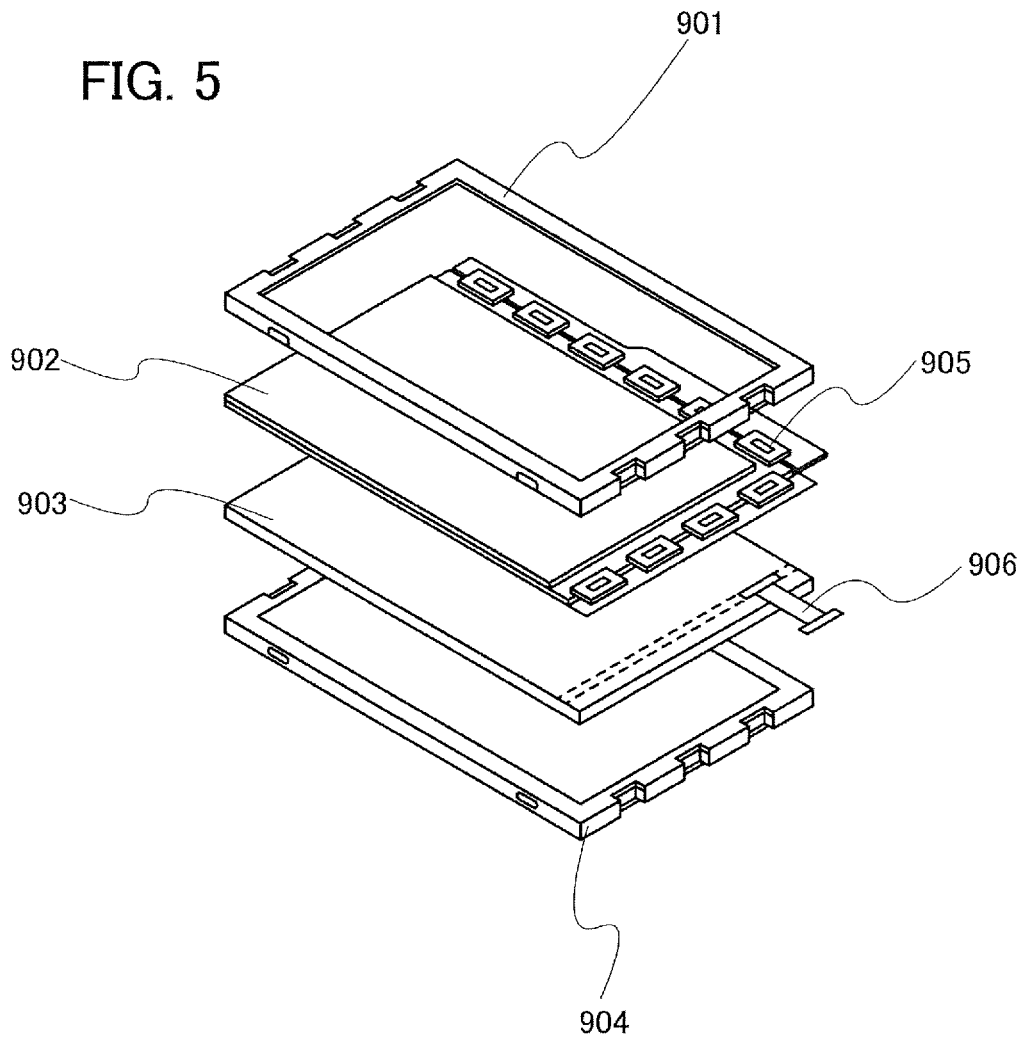
FIG. 5 illustrates a liquid crystal display device according to one embodiment of the present invention.

FIG. 5 illustrates an example of a liquid crystal display device using the light-emitting element including a compound comprising a dibenzo[f,h]quinoxaline ring and two hole-transport skeletons, where the dibenzo[f,h]quinoxaline ring and the two hole-transport skeletons are bonded to an aromatic hydrocarbon group for a backlight. The liquid crystal display device illustrated in FIG. 5 includes a housing 901, a liquid crystal layer 902, a backlight 903, and a housing 904.

The liquid crystal layer 902 is connected to a driver IC 905. The light-emitting element including a carbazole compound described in Embodiment 1 is used in the backlight 903, to which a current is supplied through a terminal 906.

A light-emitting element including the compound comprising a dibenzo[f,h]quinoxaline ring and two hole-transport skeletons, where the dibenzo[f,h]quinoxaline ring and the two hole-transport skeletons are bonded to an aromatic hydrocarbon group is used for the backlight of the liquid crystal display device, and thus a backlight having reduced power consumption can be obtained. In addition, use of the compound comprising a dibenzo[f,h]quinoxaline ring and two hole-transport skeletons, where the dibenzo[f,h]quinoxaline ring and the two hole-transport skeletons are bonded to an aromatic hydrocarbon group enables manufacture of a planar-emission lighting device and further a larger-area planar-emission lighting device; therefore, the backlight can be a larger-area backlight, and the liquid crystal display device can also be a larger-area device. In addition, the backlight using the light-emitting element can be thinner than a conventional one; accordingly, the display device can also be thinner. Furthermore, a backlight including the light-emitting element can have high reliability.

Figure 6:
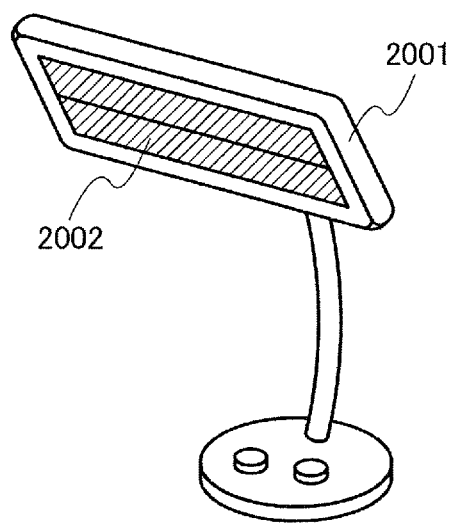
FIG. 6 illustrates a lighting device according to one embodiment of the present invention.

FIG. 6 illustrates an example in which a lighting device including a compound comprising a dibenzo[f,h]quinoxaline ring and two hole-transport skeletons, where the dibenzo[f,h]quinoxaline ring and the two hole-transport skeletons are bonded to an aromatic hydrocarbon group is used for a desk lamp that is a lighting device. The desk lamp illustrated in FIG. 6 includes a housing 2001 and a light source 2002, and the light-emitting element is used for the light source 2002.

Figure 7:
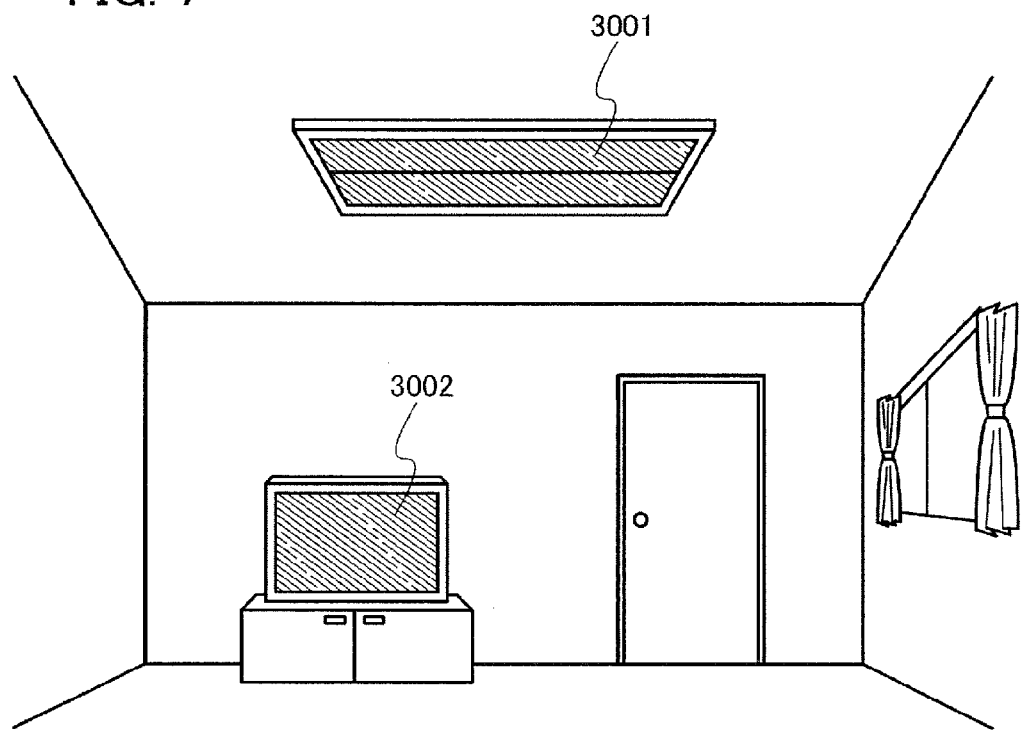
FIG. 7 illustrates a lighting device according to one embodiment of the present invention.

FIG. 7 illustrates an example in which a light-emitting element including a compound comprising a dibenzo[f,h]quinoxaline ring and two hole-transport skeletons, where the dibenzo[f,h]quinoxaline ring and the two hole-transport skeletons are bonded to an aromatic hydrocarbon group is used for indoor lighting devices 3001 and 3002. Since the light-emitting element has reduced power consumption, a lighting device that has reduced power consumption can be obtained. Further, since the light-emitting element can have a large area, the light-emitting element can be used for a large-area lighting device. Furthermore, since the light-emitting element is thin, a lighting device having a reduced thickness can be fabricated. Still furthermore, since the light-emitting element is driven at low voltage, a lighting device having low driving voltage can be fabricated.

Figure 8:
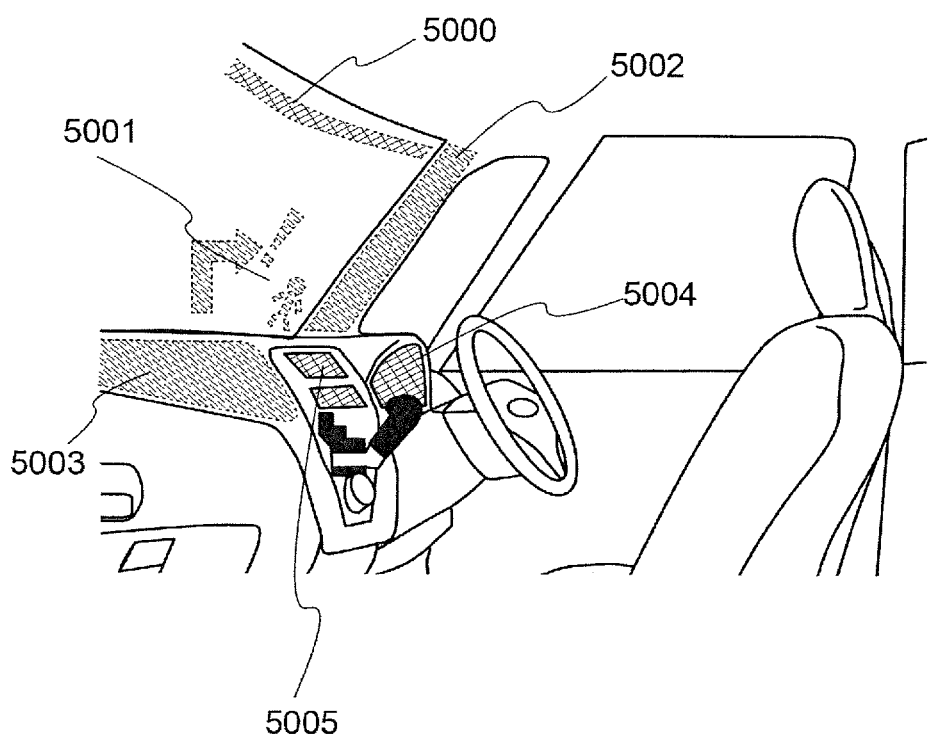
FIG. 8 illustrates an electronic device according to one embodiment of the present invention.

A light-emitting element including the compound comprising a dibenzo[f,h]quinoxaline ring and two hole-transport skeletons, where the dibenzo[f,h]quinoxaline ring and the two hole-transport skeletons are bonded to an aromatic hydrocarbon group can also be used for an automobile windshield or dashboard. One mode in which the light-emitting element is used for an automobile windshield and an automobile dashboard is illustrated in FIG. 8. Displays 5000 to 5005 each include the light-emitting element.

The display 5000 and the display 5001 are display devices which are provided in the automobile windshield and in which the light-emitting element including compound comprising a dibenzo[f,h]quinoxaline ring and two hole-transport skeletons, where the dibenzo[f,h]quinoxaline ring and the two hole-transport skeletons are bonded to an aromatic hydrocarbon group is incorporated. The light-emitting element can be formed into so-called see-through display devices, through which the opposite side can be seen, by including a first electrode and a second electrode formed with electrodes having a light-transmitting property. Such see-through display devices can be provided even in the automobile windshield, without hindering the vision. Note in the case where a transistor for driving the light-emitting element is provided, a transistor having a light-transmitting property, such as an organic transistor using an organic semiconductor material or a transistor using an oxide semiconductor, is preferably used.

The display 5002 is a display device which is provided in a pillar portion and in which the light-emitting element including the compound comprising a dibenzo[f,h]quinoxaline ring and two hole-transport skeletons, where the dibenzo[f,h]quinoxaline ring and the two hole-transport skeletons are bonded to an aromatic hydrocarbon group is incorporated. The display 5002 can compensate for the view hindered by the pillar portion by showing an image taken by an imaging unit provided in the automobile body. Similarly, the display 5003 provided in the dashboard can compensate for the view hindered by the automobile body by showing an image taken by an imaging unit provided in the outside of the automobile body, which leads to elimination of blind areas and enhancement of safety. Showing an image so as to compensate for the area which a driver cannot see, makes it possible for the driver to confirm safety easily and comfortably.

The display 5004 and the display 5005 can provide a variety of kinds of information such as information of navigation, speedometer, tachometer, mileage (travel distance), fuel meter, gearshift indicator, and air condition. The content or layout of the display can be changed freely by a user as appropriate. Further, such information can also be shown in the displays 5000 to 5003. Note that the displays 5000 to 5005 can also be used as lighting devices.

By including the compound comprising a dibenzo[f,h]quinoxaline ring and two hole-transport skeletons, where the dibenzo[f,h]quinoxaline ring and the two hole-transport skeletons are bonded to an aromatic hydrocarbon group, the light-emitting element can have low driving voltage. In addition, a light-emitting element having lower power consumption can be provided. When a number of large screens such as displays 5000 to 5005 are provided, load on a battery can be reduced, which provides comfortable use. The light-emitting device and the lighting device each using the light-emitting element can be suitably used as an in-vehicle light-emitting device or lighting device.

Embodiment 6

Figure 9A:
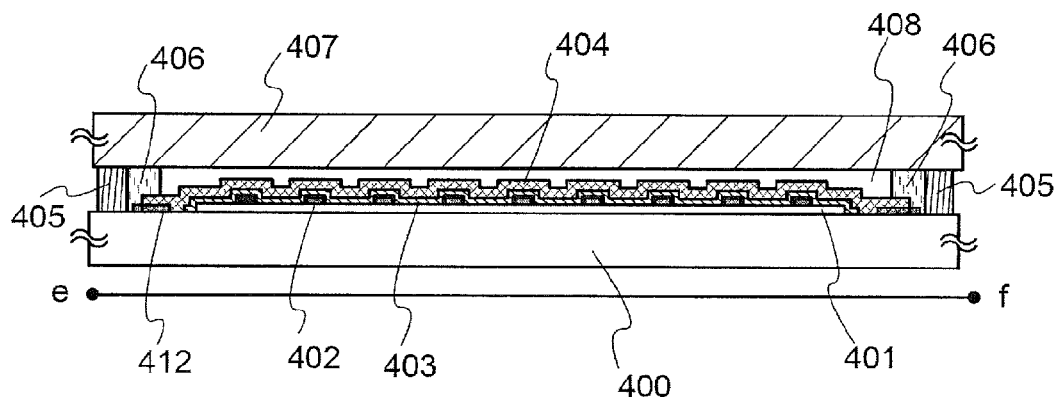
FIGS. 9A and 9B illustrate a lighting device according to one embodiment of the present invention.
Figure 9B:
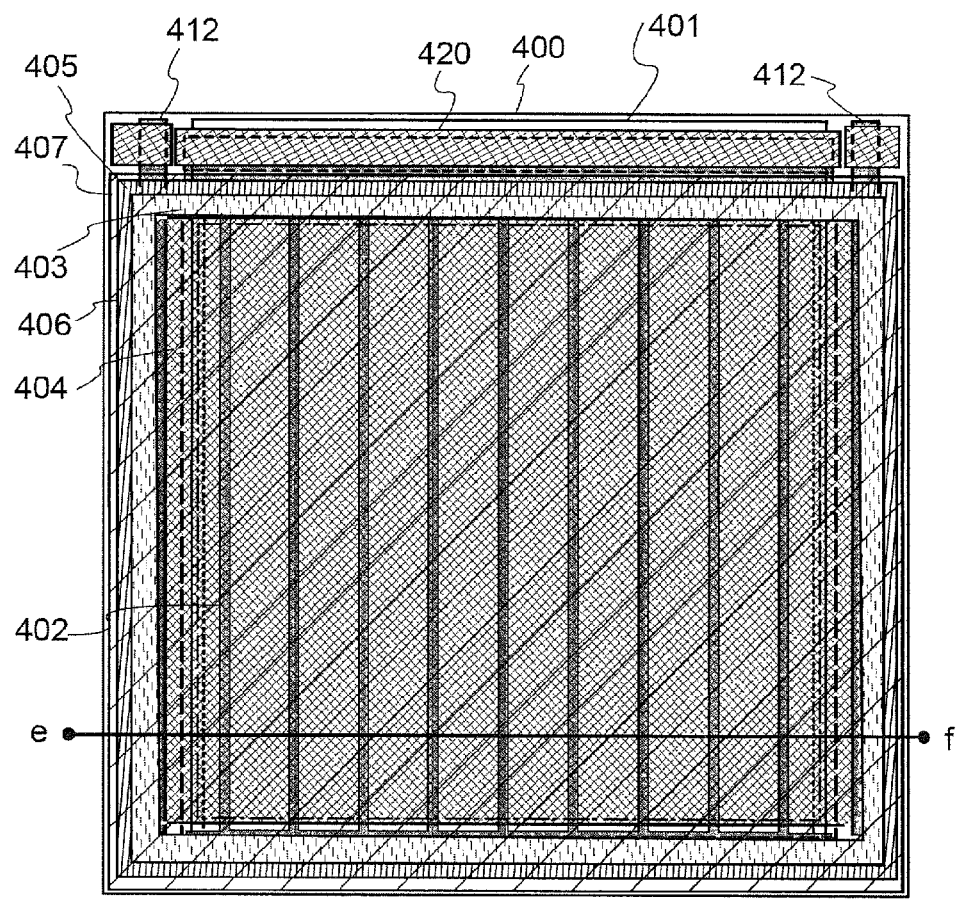

This embodiment shows an example in which the light-emitting element described in Embodiment 2 or 3 is used for a lighting device with reference to FIGS. 9A and 9B. FIG. 9B is a top view of the lighting device, and FIG. 9A is a cross-sectional view taken along line e-f in FIG. 9B.

In the lighting device of this embodiment, a first electrode 401 is formed over a substrate 400 which is a support and has a light-transmitting property. The first electrode 401 corresponds to the first electrode 101 in Embodiment 2.

An auxiliary electrode 402 is provided over the first electrode 401. Since this embodiment shows an example in which light emission is extracted through the first electrode 401 side, the first electrode 401 is formed with a material having a light-transmitting property. The auxiliary electrode 402 is provided in order to compensate for low conductivity of the material having a light-transmitting property, and has a function of suppressing luminance unevenness in a light emission surface due to voltage drop caused by high resistance of the first electrode 401. The auxiliary electrode 402 is formed with a material having higher conductivity at least than the material of the first electrode 401, and is preferably formed using a material having high conductivity such as aluminum. Note that surfaces of the auxiliary electrode 402 other than a portion thereof in contact with the first electrode 401 are preferably covered with an insulating layer. This is for suppressing light emission over the upper portion of the auxiliary electrode 402, which cannot be extracted, for reducing a reactive current, and for suppressing a reduction in power efficiency. Note that a pad 412 for applying voltage to a second electrode 404 may be formed concurrently with the formation of the auxiliary electrode 402.

An EL layer 403 is formed over the first electrode 401 and the auxiliary electrode 402. The EL layer 403 has a structure corresponding to the structure of the EL layer 103 in Embodiment 2 or a structure in which the light-emitting units 511 and 512 and the charge generation layer 513 in Embodiment 3 are combined. The description in Embodiments 2 and 3 can be referred to for these structures. Note that the EL layer 403 is preferably formed to be slightly larger than the first electrode 401 when seen from above so as to also serve as an insulating layer that suppresses a short circuit between the first electrode 401 and the second electrode 404.

The second electrode 404 is formed to cover the EL layer 403. The second electrode 404 corresponds to the second electrode 102 in Embodiment 2 and has a structure similar to the second electrode 102. In this embodiment, the second electrode 404 is preferably formed using a material having high reflectance because light is extracted through the first electrode 401 side. In this embodiment, the second electrode 404 is connected to the pad 412, whereby voltage is applied thereto.

As described above, the lighting device described in this embodiment includes a light-emitting element including the first electrode 401, the EL layer 403, and the second electrode 404 (and the auxiliary electrode 402). Since the light-emitting element has high emission efficiency, the lighting device of this embodiment can have low power consumption. In addition, since the light-emitting element has high reliability, the lighting device of this embodiment can be a lighting device having high reliability.

The light-emitting element having the above structure is fixed to a sealing substrate 407 with sealing materials 405 and 406 to seal the light-emitting element, whereby the lighting device is completed. It is possible to use only either the sealing material 405 or the sealing material 406. In addition, the inner sealing material 406 can be mixed with a desiccant, whereby moisture is adsorbed and the reliability is increased.

When parts of the pad 412, the first electrode 401, and the auxiliary electrode 402 are extended to the outside of the sealing materials 405 and 406, the extended parts can serve as external input terminals. An IC chip 420 provided with a converter or the like may be provided over the external input terminals.

In the above manner, the lighting device described in this embodiment includes an EL element including the light-emitting element described in Embodiment 2 or 3; thus, the lighting device can have low power consumption, low driving voltage, and/or high reliability.

Example 1

Synthesis Example 1

In this example, a method of synthesizing the heterocyclic compound described in Embodiment 1, 2-[3,5-bis(9H-carbazol-9-yl)phenyl]dibenzo[f,h]quinoxaline (abbreviation: 2Cz2PDBq) represented by the following structural formula (100) is described. The heterocyclic compound can be expressed as a compound comprising a dibenzo[f,h]quinoxaline ring and two hole-transport skeletons, where the dibenzo[f,h]quinoxaline ring and the two hole-transport skeletons are bonded to an aromatic hydrocarbon group.

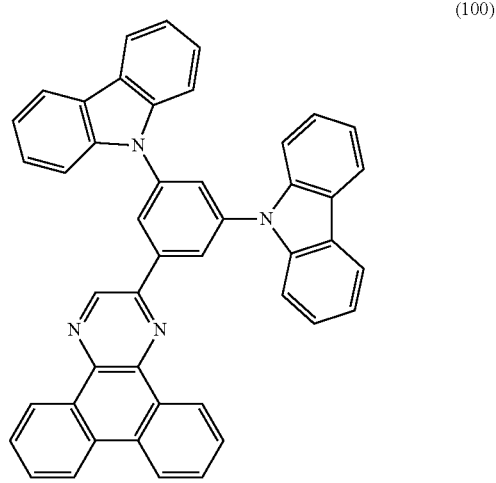 [SMILES: c1ccc2c(c1)c1ccccc1c1nc(-c3cc(-n4c5ccccc5c5ccccc54)cc(-n4c5ccccc5c5ccccc54)c3)cnc21]

(100)

Step 1: Synthesis of 9,9'-(5-bromo-1,3-phenylene)-bis-9H-carbazole

Into a 300-mL three-neck flask were put 9.4 g (30 mmol) of 1,3,5-tribromobenzene, 10 g (60 mmol) of 9H-carbazole, 1.1 g (6.0 mmol) of copper(I) iodide, 16 g (0.12 mol) of potassium carbonate, and 0.79 g (3.0 mol) of 18-crown-6-ether, and the air in the flask was replaced with nitrogen. This mixture was stirred under a nitrogen stream at 90° C. for 15 minutes. After the stirring, to this mixture was added 9.0 mL of 1,3-dimethyl-3,4,5,6-tetrahydro-2(1H)pyrimidinone (abbreviation: DMPU), and the mixture in this flask was stirred at 185° C. for three hours. After the stirring, the mixture in this flask was cooled to 85° C. and 70 ml, of toluene was added thereto, and then stirred at 120° C. for four hours. After the stirring, this mixture was cooled to 80° C. and 200 mL of toluene was added thereto, and subjected to suction filtration to obtain a filtrate. The filtrate was washed with saturated saline. Water was removed from an organic layer using magnesium sulfate, and then the mixture was gravity-filtered. The obtained filtrate was concentrated to obtain a solid, and 85 mL of chloroform was added to the solid. This mixture was subjected to suction filtration to obtain a filtrate. The filtrate was concentrated to obtain a solid. The solid was purified by silica gel column chromatography (a developing solvent:a mixed solvent of toluene:hexane=1:100) to obtain a solid. This solid was dried under reduced pressure, so that 2.8 g of white powder, which was the object of the synthesis, was obtained in a yield of 19%. The synthesis scheme of Step 1 is shown in (a-1).

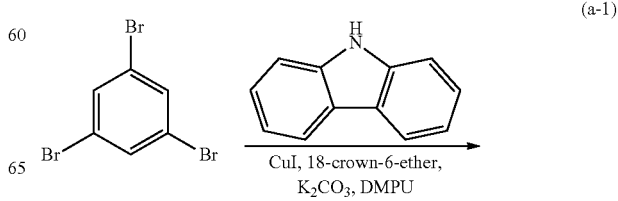

(a-1)

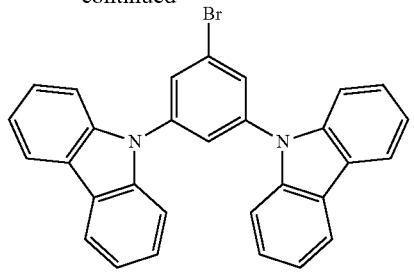

Into 100-mL three-neck flask was put 2.8 g (5.7 mmol) of 9,9'-(5-bromo-1,3-phenylene)-bis-9H-carbazole, and the air in the flask was replaced with nitrogen. Into this flask was added 25 nit of tetrahydrofuran (THF), and the solution was cooled to −80° C. Into this solution was dripped 3.9 mL (6.3 mmol) of n-butyllithium (a 1.6 mol/L hexane solution) with a syringe. After the dripping, this solution was stirred for 90 minutes without changing the temperature. After the stirring, 0.80 mL (7.4 mmol) of trimethyl borate was added to this solution, and the mixture was stirred for one hour while being returned to room temperature. After the stirring, about 10 mL of dilute hydrochloric acid (1.0 mol/L) was added to this solution. Then, the aqueous layer of this mixture was extracted with ethyl acetate, and the extracted solution and the organic layer were combined and washed with a saturated aqueous solution of sodium hydrogen carbonate and saturated saline. Water was removed from the organic layer using magnesium sulfate, and then the mixture was gravity-filtered. The obtained filtrate was concentrated to obtain a solid. A mixed solvent of ethyl acetate and hexane was added to the obtained solid, the mixture was irradiated with ultrasonic waves, and the solid was collected by suction filtration, so that 2.1 g of orange powder, which was the object of the synthesis, was obtained in a yield of 83%. The synthesis scheme of Step 2 is shown in (a-2).

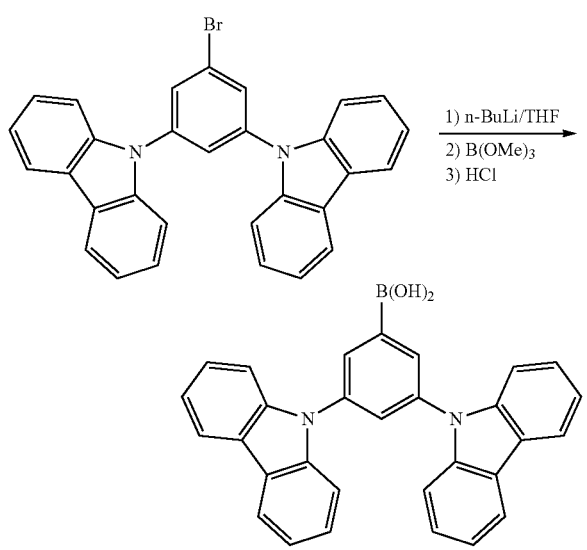

Step 3: Synthesis of 2-[3,5-bis(9H-carbazol-9-yl) phenyl]dibenzo[f,h]quinoxaline (abbreviation: 2Cz2PDBq)

Into a 100-mL three-neck flask were put 1.2 g (4.8 mmol) of 2-chlorodibenzo[f,h]quinoxaline, 2.1 g (4.7 mmol) of 3,5-bis(9H-carbazol-9-yl)phenylboronic acid, and the air in the flask was replaced with nitrogen. To this mixture were added 18 mL of toluene, 6.0 mL of ethanol, and 6.0 mL of an aqueous solution of potassium carbonate (2.0 mol/L). This mixture was stirred to be degassed while the pressure was reduced. To this mixture was added 0.11 g (0.096 mmol) of tetrakis(triphenylphosphine)palladium(0), and the mixture was stirred at 80° C. for six hours under a nitrogen stream, so that a solid was precipitated. The precipitated solid was collected by suction filtration. To the obtained solid was added about 100 mL of water, washed by ultrasonic wave irradiation, and subjected to suction filtration to obtain a solid. To the obtained solid was added about 100 mL of ethanol, washed by ultrasonic wave irradiation, and subjected to suction filtration to obtain a solid. The obtained solid was dissolved in about 1.5 L of hot toluene, and this solution was suction-filtered through Celite and Florisil. A solid obtained by concentration of the filtrate was washed with toluene, so that 2.8 g of a yellow solid, which was the object of the synthesis, was obtained in a yield of 94%. The synthesis scheme of Step 3 is shown in (a-3).

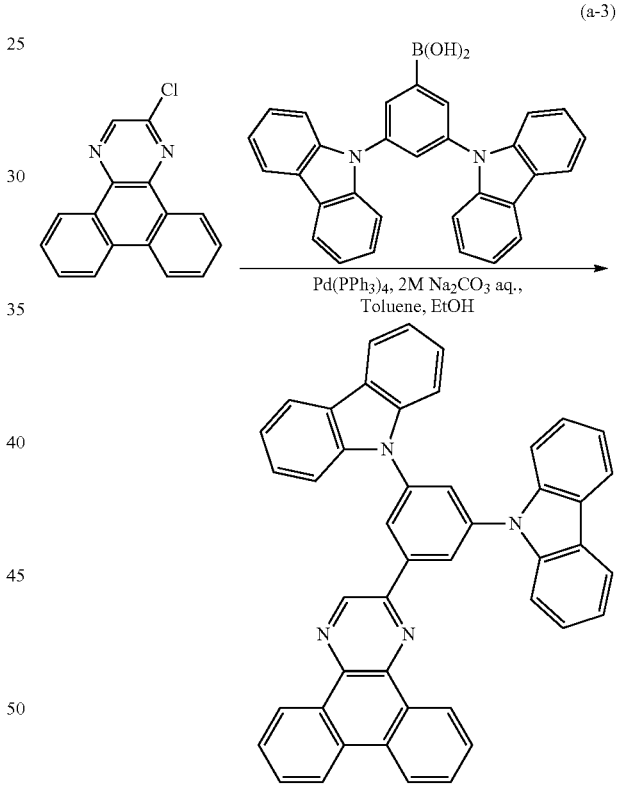

By a train sublimation method, 2.7 g of the obtained yellow solid was purified. In the purification by sublimation, 2Cz2PDBq was heated at 320° C. under a pressure of 2.7 Pa with a flow rate of argon gas of 5.0 mL/min. After the purification by sublimation, 1.6 g of a white solid was obtained in a yield of 60%.

Figure 10A:
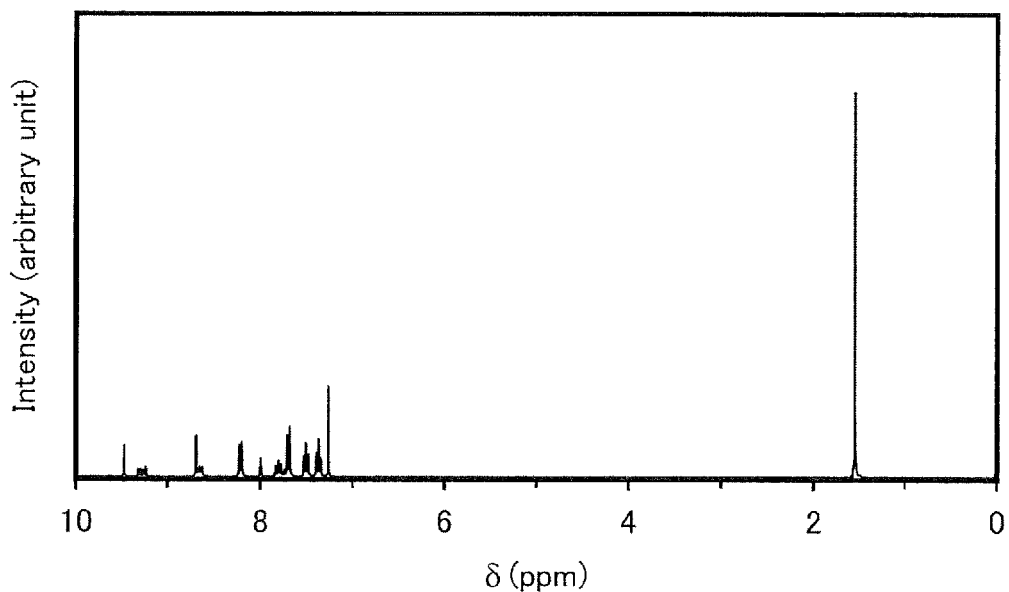
FIGS. 10A and 10B show $^1$H NMR charts of 2Cz2PDBq.
Figure 10B:
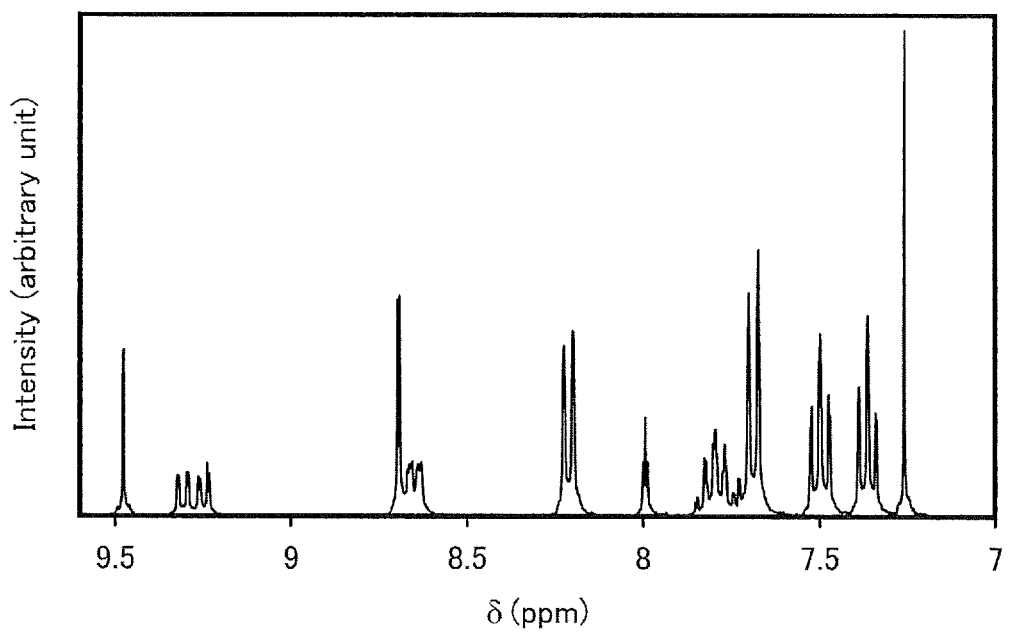

By analysis of the obtained white solid by $^1$H NMR, the solid was identified as 2Cz2PDBq. The results of the analysis are shown below and FIGS. 10A and 10B are charts thereof. Note that FIG. 10B is a chart where the range of from 7 ppm to 9.6 ppm in FIG. 10A is enlarged.

$^1$H NMR (CDCl$_3$, 300 MHz): δ=7.36 (t, J=7.5 Hz, 4H), 7.50 (ddd, J=7.2, 0.9 Hz, 4H), 7.67-7.85 (m, 8H), 7.99 (t, J=1.8 Hz, 1H), 8.21 (d, J=7.2 Hz, 4H), 8.64 (dd, J=2.4 Hz, 2H), 8.69 (d, J=1.8 Hz, 2H), 9.25 (dd, J=1.5, 7.8 Hz, 1H), 9.30 (dd, J=1.5, 7.8 Hz, 1H), 9.48 (s, 1H)

Figure 11A:
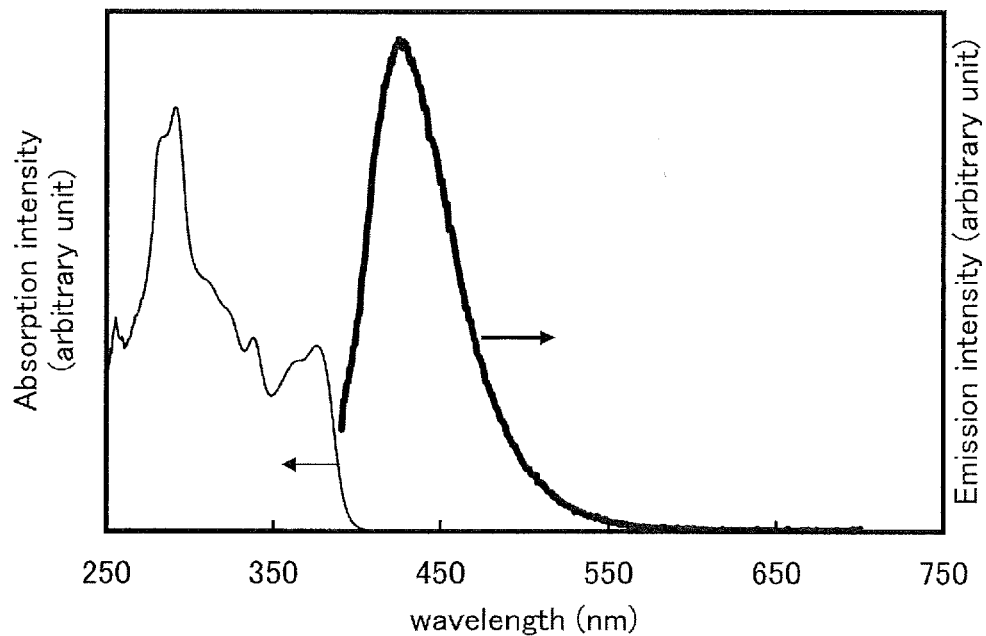
FIGS. 11A and 11B show an absorption and emission spectra of 2Cz2PDBq.
Figure 11B:
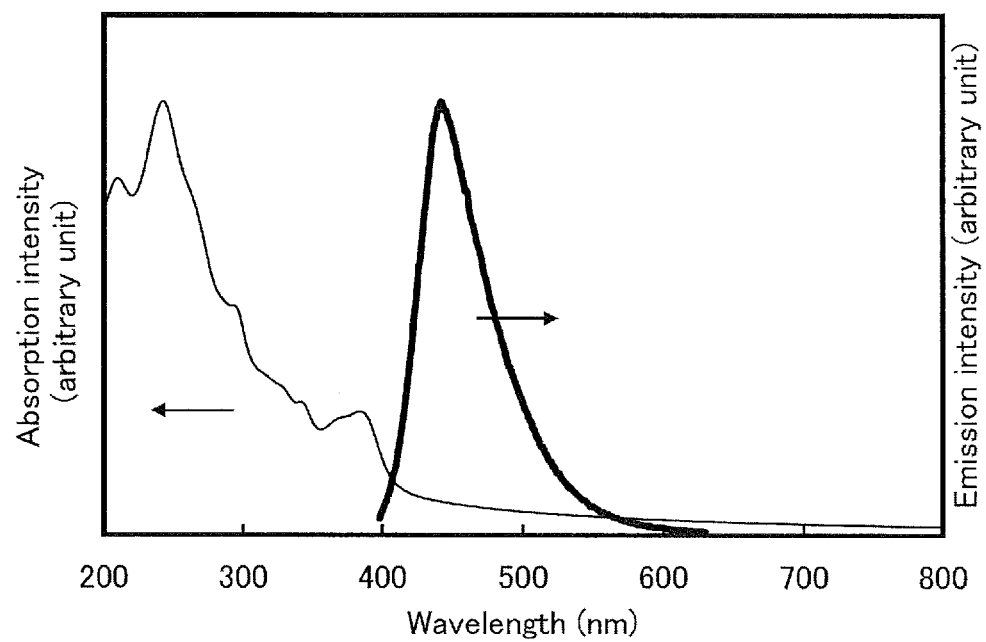

Next, absorption and emission spectra of 2Cz2PDBq in a toluene solution of 2Cz2PDBq are shown in FIG. 11A, and absorption and emission spectra of a thin film of 2Cz2PDBq are shown in FIG. 11B. The absorption spectrum was measured with a UV-visible spectrophotometer (V-550, manufactured by JASCO Corporation). A toluene solution of 2Cz2PDBq was put in a quartz cell and an absorption spectrum of 2Cz2PDBq in the toluene solution was measured. From this absorption spectrum, an absorption spectrum of the toluene solution measured with the quartz cell was subtracted, and the resultant value was shown in the drawing. In addition, as for the absorption spectrum of the thin film, a sample was prepared by evaporation of 2Cz2PDBq on a quartz substrate, and the absorption spectrum obtained by subtraction of an absorption spectrum of quartz from the absorption spectrum of this sample is shown in the drawing. The emission spectrum was measured with a UV-visible spectrophotometer (V-550, manufactured by JASCO Corporation) which was used for the measurement of the absorption spectrum. The emission spectrum of 2Cz2PDBq in a toluene solution of 2Cz2PDBq was measured with the toluene solution of 2Cz2PDBq put in a quartz cell, and the emission spectrum of the thin film was measured with a sample prepared by evaporation of 2Cz2PDBq on a quartz substrate. These show that the maximum absorption wavelengths of 2Cz2PDBq in the toluene solution of 2Cz2PDBq were around 376 nm, around 338 nm, and around 292 nm and that the maximum emission wavelengths thereof were around 427 nm (an excitation wavelength of 376 nm). These also show that the maximum absorption wavelengths of the thin film were around 384 nm, around 372 nm, around 341 nm, around 325 nm, around 311 nm, around 293 nm, around 262 nm, around 243 nm, and 210 nm and that the largest maximum emission wavelength thereof was around 442 nm (an excitation wavelength of 383 nm).

Further, the ionization potential of a thin film of 2Cz2PDBq was measured by a photoelectron spectrometer (AC-2, produced by Riken Keiki, Co., Ltd.) in the air. The obtained value of the ionization potential was converted to a negative value, so that the HOMO level of 2Cz2PDBq was −5.89 eV. From the data of the absorption spectra of the thin film in FIGS. 11A and 11B, the absorption edge of 2Cz2PDBq, which was obtained from a Tauc plot with an assumption of direct transition, was 3.06 eV. Therefore, the optical energy gap of 2Cz2PDBq in the solid state was estimated at 3.06 eV; from the values of the HOMO level obtained above and this energy gap, the LUMO level of 2Cz2PDBq was able to be estimated at −2.83 eV. It was thus found that 2Cz2PDBq had a wide energy gap of 3.06 eV in the solid state. Accordingly, it can be said that the band gap and the triplet excitation energy were decreased because of the heterocyclic compound including an aromatic hydrocarbon group between a dibenzo[f,h]quinoxaline ring and two hole-transport skeletons.

Example 2

In this example, a light-emitting element in which the heterocyclic compound described in Embodiment 1, 2-[3,5-bis(9H-carbazol-9-yl)phenyl]dibenzo[f,h]quinoxaline (abbreviation: 2Cz2PDBq) (the structural formula 100) is used as a host material and an electron-transport material in a light-emitting layer including an emission center substance emitting orange phosphorescence. The heterocyclic compound is a compound comprising a dibenzo[f,h]quinoxaline ring and two hole-transport skeletons, where the dibenzo[f,h]quinoxaline ring and the two hole-transport skeletons are bonded to an aromatic hydrocarbon group.

The molecular structures of organic compounds used in this example are shown in the following structural formulae (i) to (v) and (100). An element structure is the same as that of FIG. 1A.

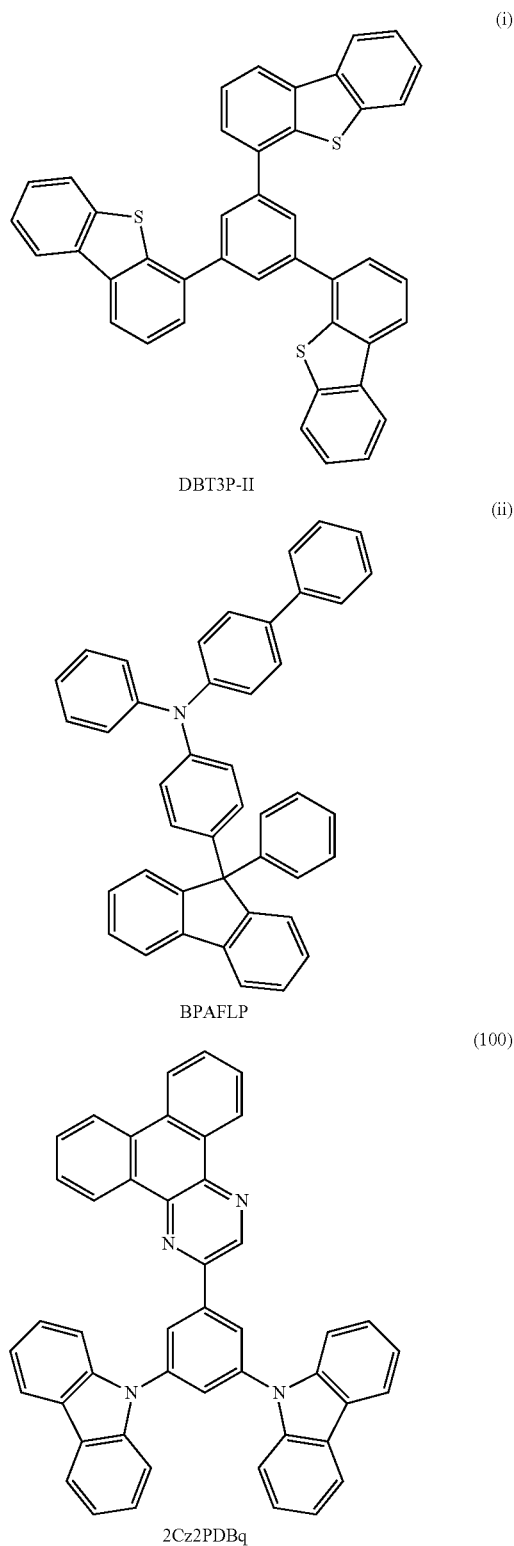

-continued

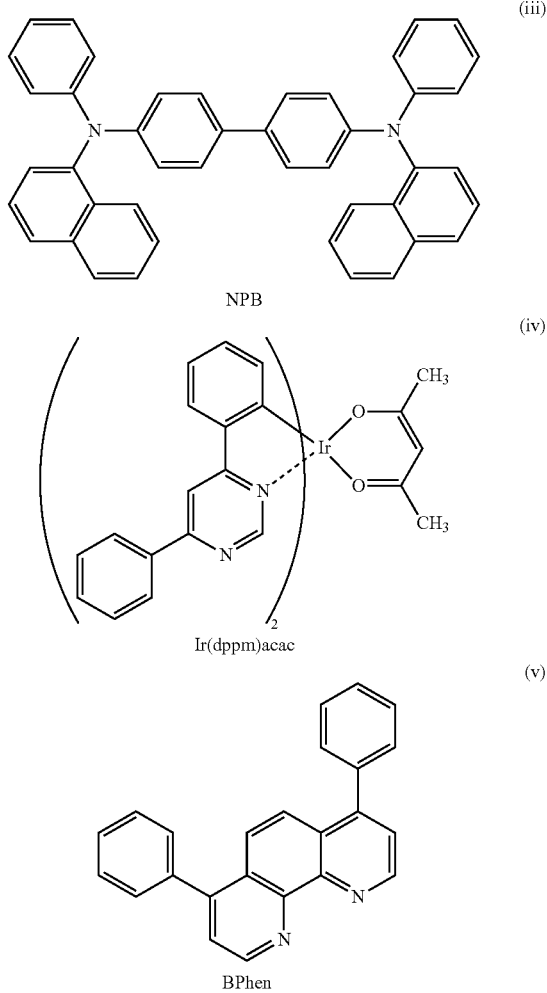

<<Fabrication of Light-Emitting Element 1>>

First, a glass substrate over which a film of indium tin oxide containing silicon (ITSO) was formed to a thickness of 110 nm was prepared as the first electrode 101. A surface of the ITSO film was covered with a polyimide film such that an area of 2 mm×2 mm of the surface was exposed, which corresponded to the electrode area. In pretreatment for forming the light-emitting elements over the substrate, the surface of the substrate was washed with water and baked at 200° C. for one hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed to a holder provided in the vacuum evaporation apparatus such that the surface of the substrate over which the ITSO film was formed faced downward.

After the pressure in the vacuum evaporation apparatus was reduced to $10^{-4}$ Pa, 1,3,5-tri(dibenzothiophen-4-yl)-benzene (abbreviation: DBT3P-II) represented by the above structural formula (i) and molybdenum(VI) oxide were co-evaporated so that the weight ratio of DBT3P-II:molybdenum oxide was 2:1; thus, the hole-injection layer 111 was formed.

The thickness thereof was set to 40 nm. Note that the co-evaporation is an evaporation method in which a plurality of different substances is concurrently vaporized from the respective different evaporation sources.

Next, 4-phenyl-4'-(9-phenylfluoren-9-yl)triphenylamine (abbreviation: BPAFLP) represented by the above structural formula (ii) was evaporated to a thickness of 20 nm, thereby forming the hole-transport layer 112.

Over the hole-transport layer 112, 2-[3,5-bis(9H-carbazol-9-yl)phenyl]dibenzo[f,h]quinoxaline (abbreviation: 2Cz2PDBq) that is the heterocyclic compound represented by the structural formula (100) and described in Embodiment 1, 4,4'-bis[N-(1-naphthyl)-N-phenylamino]biphenyl (abbreviation: NPB) represented by the structural formula (iii), and (Acetylacetonato)bis(4,6-diphenylpyrimidinato)iridium(III) (abbreviation: [Ir(dppm)$_2$(acac)]) represented by the structural formula (Iv) were evaporated so that the weight ratio of 2Cz2PDBq to NPB and [Ir(nbppm)$_2$(acac)] was 0.8:0.2:0.05 to form the light-emitting layer 113 with a thickness of 40 nm.

Next, 2Cz2PDBq was evaporated to a thickness of 15 nm, and then bathophenanthroline (abbreviation: BPhen) represented by the above structural formula (v) was evaporated to a thickness of 15 nm, so that the electron-transport layer 114 was formed.

Further, lithium fluoride was evaporated to a thickness of 1 nm over the electron-transport layer 114, so that the electron-injection layer was formed. Lastly, an aluminum film was formed to a thickness of 200 nm as the second electrode 102 functioning as a cathode. Accordingly, Light-emitting Element 1 was completed. Note that in the above evaporation processes, evaporation was all performed by a resistance heating method. Light-emitting Element 1 corresponds to the light-emitting element described in detail in Embodiment 2.

<<Operation Characteristics of Light-Emitting Element 1>>

Light-emitting Element 1 thus obtained was sealed in a glove box under a nitrogen atmosphere without being exposed to the air. Then, the operation characteristics of the light-emitting element were measured. Note that the measurement was carried out at room temperature (in an atmosphere kept at 25° C.).

Figure 12:
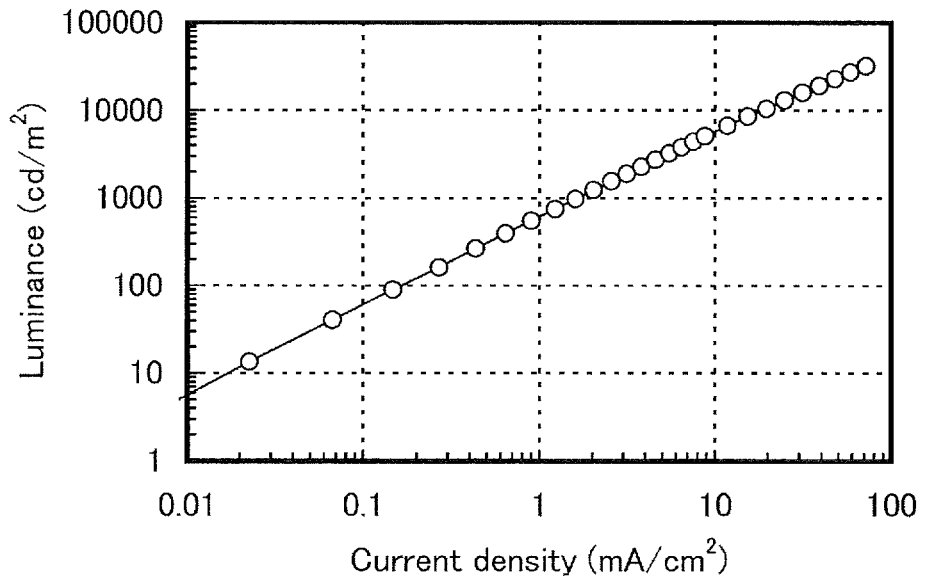
FIG. 12 shows the current density-luminance characteristics of Light-emitting Element 1.
Figure 13:
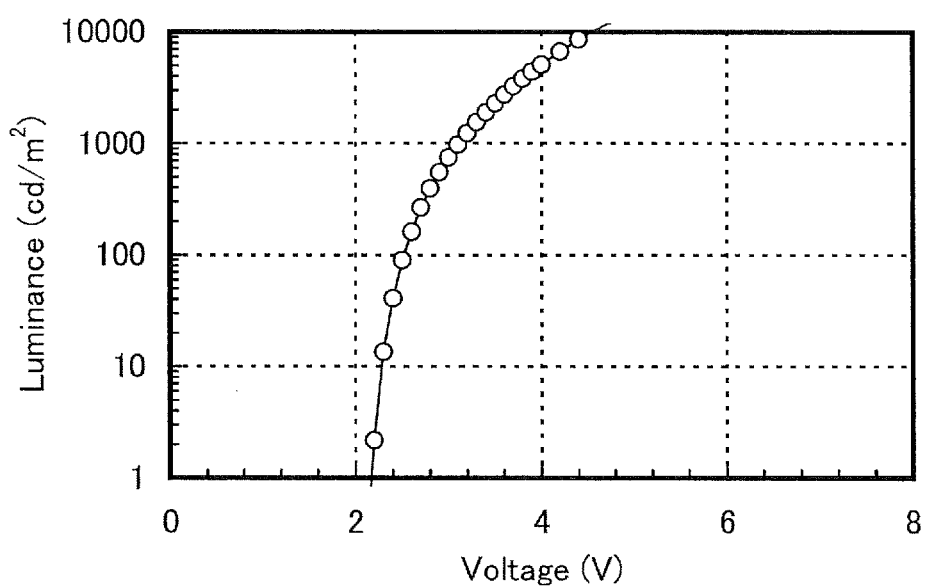
FIG. 13 shows the voltage-luminance characteristics of Light-emitting Element 1.
Figure 14:
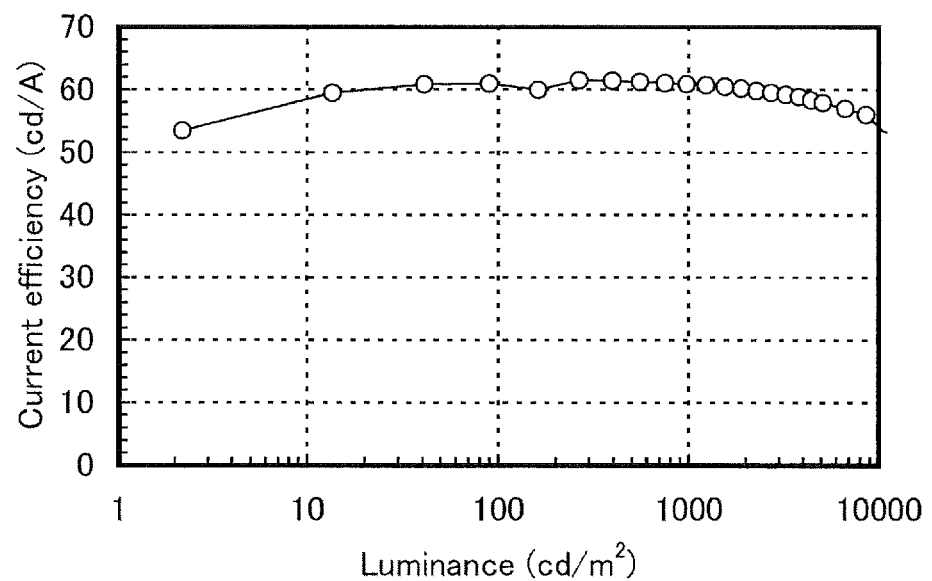
FIG. 14 shows the luminance-current efficiency characteristics of Light-emitting Element 1.

FIG. 12 shows current density-luminance characteristics of Light-emitting Element 1, FIG. 13 shows voltage-luminance characteristics thereof, and FIG. 14 shows luminance-current efficiency characteristics thereof. In FIG. 12, the vertical axis represents luminance (cd/m$^2$), and the horizontal axis represents current density (mA/cm$^2$). In FIG. 13, the vertical axis represents luminance (cd/m$^2$), and the horizontal axis represents voltage (V). In FIG. 14, the vertical axis represents current efficiency (cd/A), and the horizontal axis represents luminance (cd/m$^2$).

FIG. 12 shows that Light-emitting Element 1 (the light-emitting element described in detail in Embodiment 2) which emits orange phosphorescence, in which 2Cz2PDBq that is the heterocyclic compound described in Embodiment 1 is used as a host material in a light-emitting layer, exhibits a favorable current efficiency-luminance characteristics; therefore, Light-emitting Element 1 is a light-emitting element having a high current efficiency. Moreover, FIG. 13 shows that Light-emitting Element 1 exhibits favorable luminance-voltage characteristics and is a light-emitting element having low driving voltage. This indicates that the heterocyclic compound described in Embodiment 1 has an excellent carrier-transport property. Therefore, a light-emitting element including a compound comprising a dibenzo[f,h]quinoxaline ring and two hole-transport skeletons, where the dibenzo[f,h]quinoxaline ring and the two hole-transport skeletons are bonded to an aromatic hydrocarbon group is a light-emitting element having high emission efficiency. In addition, the light-emitting element is a light-emitting element having low driving voltage.

Example 3

Synthesis Example 2

In this example, a method of synthesizing the heterocyclic compound described in Embodiment 1, 2-[3,5-bis(dibenzothiophen-4-yl)phenyl]dibenzo[f,h]quinoxaline (abbreviation: 2DBT2PDBq-II) represented by the following structural formula (200) is described. The heterocyclic compound can be expressed as a compound in which an aromatic hydrocarbon group to which two hole-transport skeletons (dibenzothiophen skeletons) are bonded is bonded to a dibenzo[f,h]quinoxaline ring.

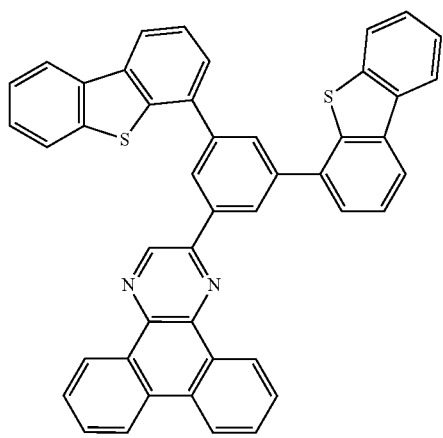

(200)

Step 1: Synthesis of 3,5-bis(dibenzothiophen-4-yl)bromobenzene

Into a 50-L reactor vessel were put 1.33 kg (4.23 mol) of tribromobenzene, 3.04 g (13.3 mol) of dibenzothiophene-4-boronic acid, 38.6 g (127 mmol) of tris(2-methylphenyl) phosphine, 3.68 kg (26.6 mol) of potassium carbonate, and 14.2 g (63.4 mmol) of palladium(II)acetate. To the mixture were added 13.3 L of water, 17.5 L of ethanol, and 39.5 L of toluene, and this mixture was degassed by being stirred under reduced pressure. After the degassing, the mixture was stirred under a nitrogen stream at 105° C. for three hours. After the stirring, the obtained mixture was filtrated to remove a solid. The obtained filtrate was concentrated to give a solid. This solid was washed with toluene and then with ethanol, and recrystallized from toluene, so that 11.7 g of a light red-brown solid was obtained in a yield of 0.53%. The synthesis scheme of Step 1 is shown in (b-1).

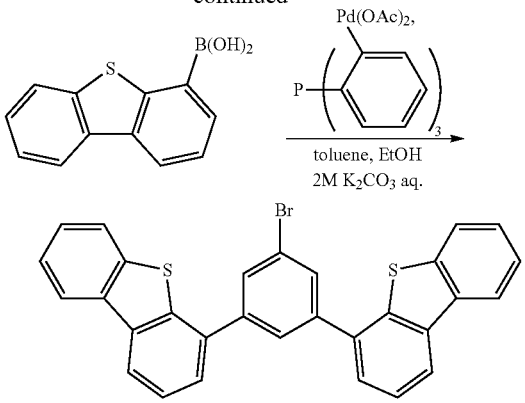

By analysis of the obtained light red-brown solid by $^1$H NMR, the solid was identified as 3,5-bis(dibenzothiophen-4-yl)bromobenzene. The results of the analysis are shown below.

$^1$H NMR (CDCl$_3$, 500 MHz): δ=7.47-7.51 (m, 4H), 7.57-7.62 (m, 4H), 7.85-7.88 (m, 2H), 7.97 (d, J1=1.5 Hz, 2H), 8.07 (t, J1=1.5 Hz, 1H), 8.19-8.23 (m, 4H)

Step 2: Synthesis of 3,5-bis(dibenzothiophen-4-yl)phenylboronic acid

Into a 500-mL three-neck flask was put 5.2 g (10 mmol) of 3,5-bis(dibenzothiophen-4-yl)bromobenzene, and the air in the flask was replaced with nitrogen. Into this flask was added 250 mL of THF, and the obtained solution was cooled to −80° C. To this solution was dripped 8.0 mL (13 mmol) of n-butyllithium (1.6 mol/L hexane solution). After completion of dripping, this solution was stirred for three hours. After a predetermined time, 4.0 mL (6.5 mmol) of n-butyllithium (1.6 mol/L hexane solution) was dripped. After completion of dripping, this solution was stirred for five hours. After the stirring, to this solution was added 2.8 mL (25 mmol) of trimethyl borate, and the mixture was stirred overnight while being returned to room temperature. After that, about 30 mL of diluted hydrochloric acid (1.0 mol/L) was added to this solution, followed by stirring for 30 minutes. Then, the aqueous layer of this mixture was extracted with ethyl acetate, and the extracted solution and an organic layer were combined and washed with a saturated aqueous solution of sodium hydrogen carbonate and then with saturated saline. The organic layer was dried with magnesium sulfate, and then the mixture was gravity filtered. The obtained filtrate was concentrated to give a solid. The obtained solid was reprecipitated from an ethyl acetate/THF/hexane solution, whereby 2.3 g of a white solid, which was the object of the synthesis, was obtained in a yield of 47%. A synthetic scheme of Step 2 is shown in (b-2).

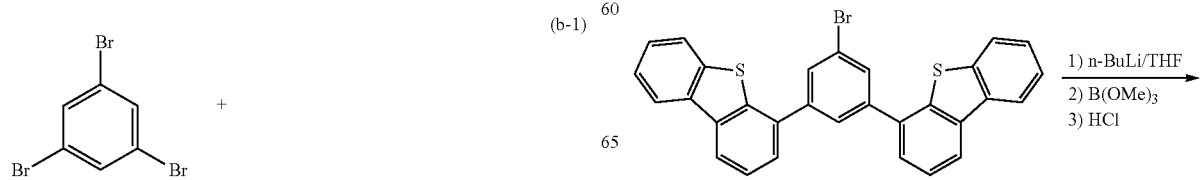

(b-2)

-continued

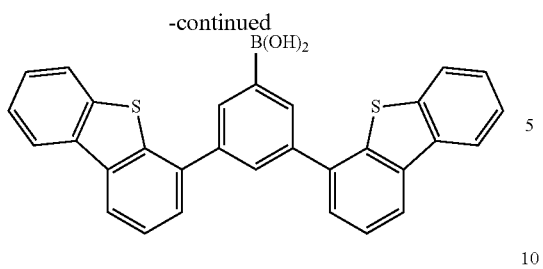

Figure 15A:
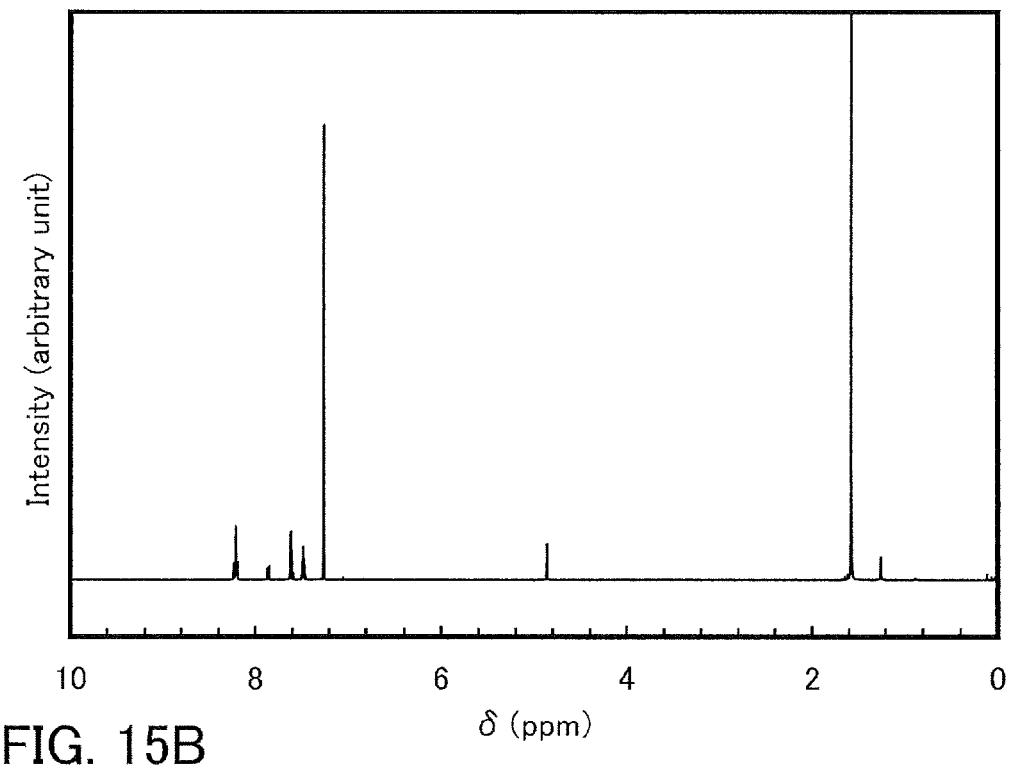
FIGS. 15A and 15B show NMR charts of 3,5-bis(dibenzothiophen-4-yl)phenylboronic acid.
Figure 15B:
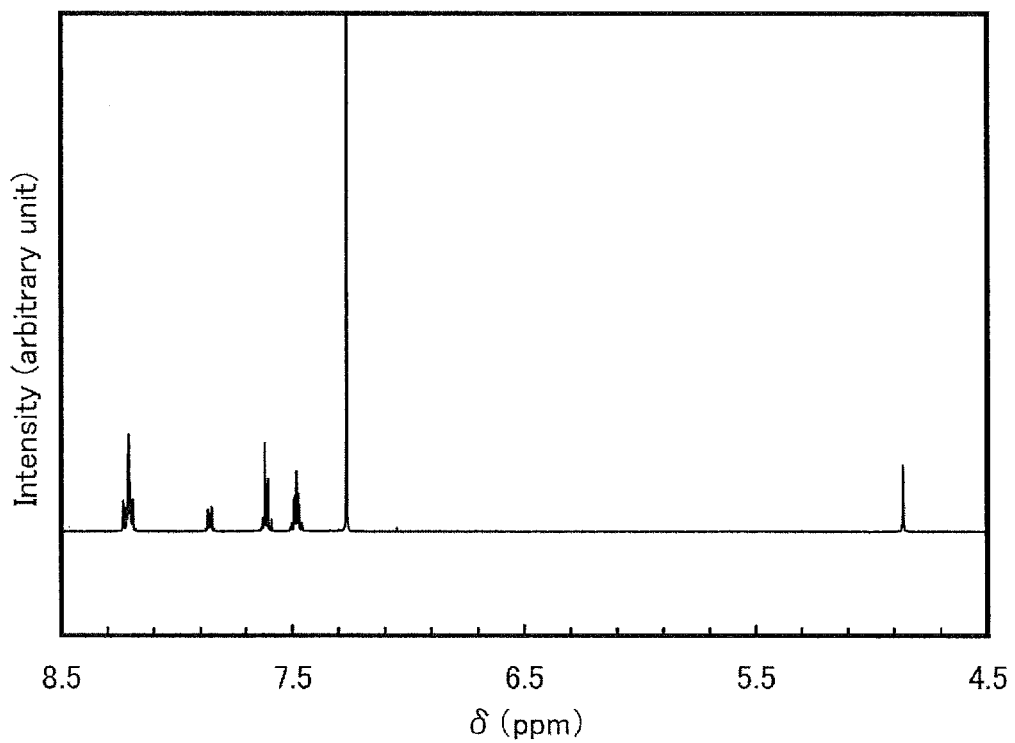

By analysis of the obtained white solid by $^1$H NMR, the solid was identified as 3,5-bis(dibenzothiophen-4-yl)phenylboronic acid. The results of the analysis are shown below and FIGS. 15A and 15B are charts thereof. Note that FIG. 15B is a chart where the range of from 4.5 ppm to 8.5 ppm in FIG. 15A is enlarged.

$^1$H NMR (CDCl$_3$, 500 MHz): δ=4.86 (s, 2H), 7.46-7.50 (m, 4H), 7.59-7.63 (m, 4H), 7.85-7.87 (m, 2H), 8.19-8.24 (m, 7H)

Step 3: Synthesis of 2-[3,5-bis(dibenzothiophen-4-yl)phenyl]dibenzo[f,h]quinoxaline (abbreviation: 2DBT2PDBq-II)

Into a 200-mL three-neck flask were put 1.2 g (4.5 mmol) of 2-chlorodibenzo[f,h]quinoxaline, 2.2 g (4.5 mmol) of 3,5-bis(dibenzothiophen-4-yl)phenylboronic acid, and 1.2 g (9.0 mmol) of potassium carbonate. To this mixture were added 23 mL of toluene, 4.5 mL of water, and 5 mL of ethanol, and this mixture was degassed by being stirred under reduced pressure. To the mixture was added 104 mg (0.09 mmol) of tetrakis(triphenylphosphine)palladium(0), and this mixture was stirred under a nitrogen stream at 100° C. for 3.5 hours. After the stirring, the obtained mixture was filtrated, and the solid was washed with water and then with ethanol. To the obtained solid was added toluene, and the mixture was suction-filtered through Celite, alumina, and Florisil. The filtrate was concentrated to give a solid. This solid was recrystallized from toluene, so that 1.4 g of a white solid was obtained in a yield of 46%. By a train sublimation method, 1.3 g of the obtained solid was purified. In the purification by sublimation, 2DBT2PDBq-II was heated at 320° C. under a pressure of 2.8 Pa with a flow rate of argon gas of 5 mL/min. After the purification by sublimation, 0.94 g of a white solid was obtained at a collection rate of 72%. The synthesis scheme of Step 3 is shown in (b-3).

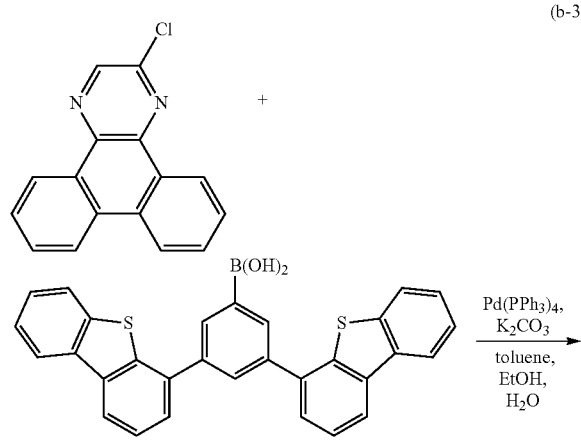

(b-3)

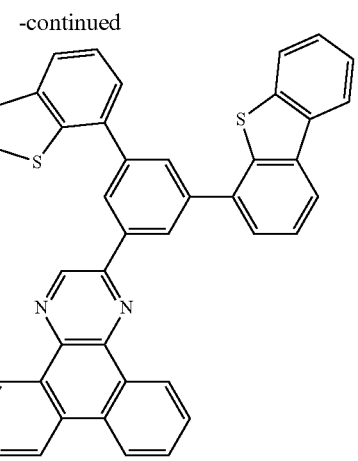

Figure 16A:
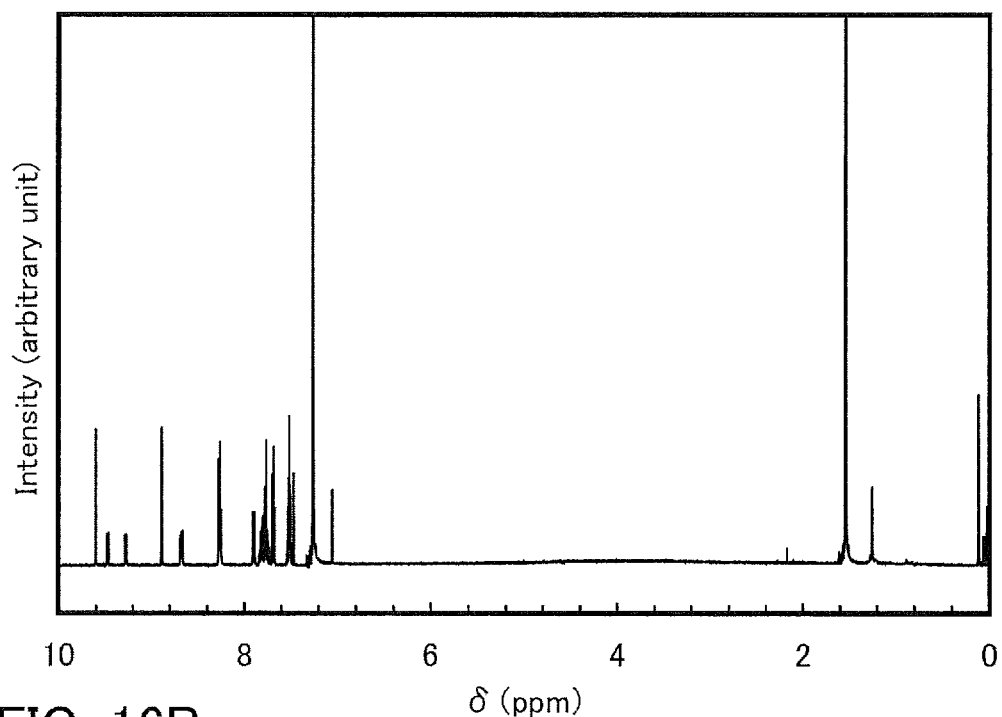
FIGS. 16A and 16B show NMR charts of 2DBT2PDBq-II.
Figure 16B:
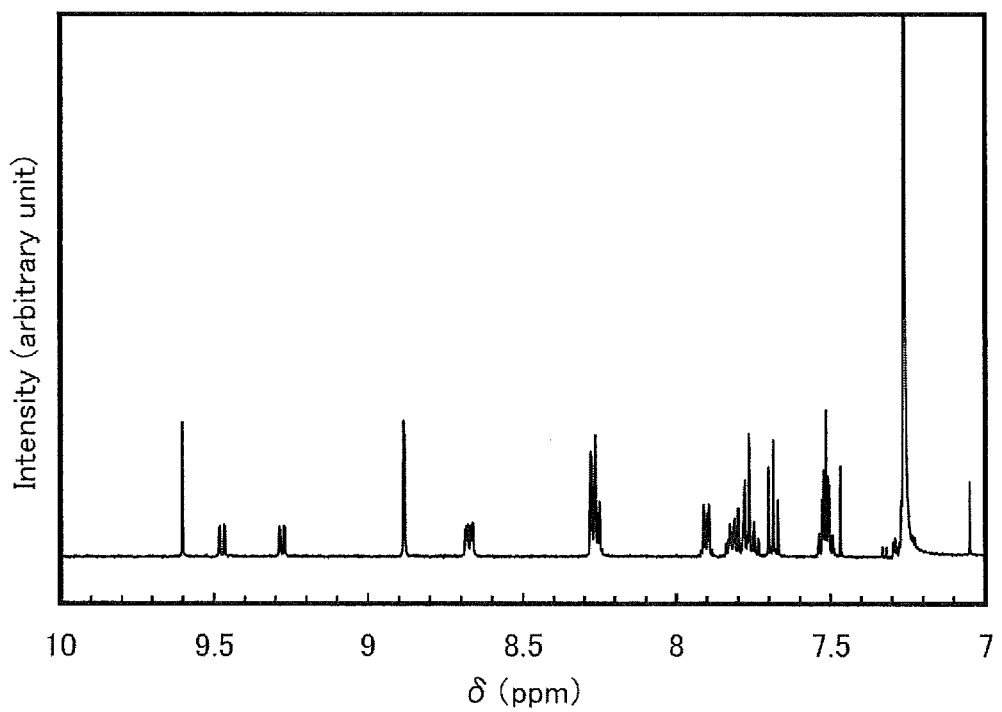

By analysis of the obtained white solid by $^1$H NMR, the solid was identified as 2DBT2PDBq-II. The results of the analysis are shown below and FIGS. 16A and 16B are NMR charts thereof. Note that FIG. 16B is a chart where the range of from 7 ppm to 10 ppm in FIG. 16A is enlarged.

$^1$H NMR (CDCl$_3$, 500 MHz): δ=7.49-7.54 (m, 4H), 7.69 (t, J1=7.5 Hz, 2H), 7.73-7.84 (m, 6H), 7.88-7.92 (m, 2H), 8.25-8.28 (m, 5H), 8.67 (dd, J1=7.5 Hz, J2=3.5 Hz, 2H), 8.88 (d, J1=1.5 Hz, 2H), 9.28 (dd, J1=1.0 Hz, J2=8.0 Hz, 1H), 9.47 (dd, J1=1.0 Hz, J2=8.0 Hz, 1H), 9.60 (s, 1H)

Figure 17A:
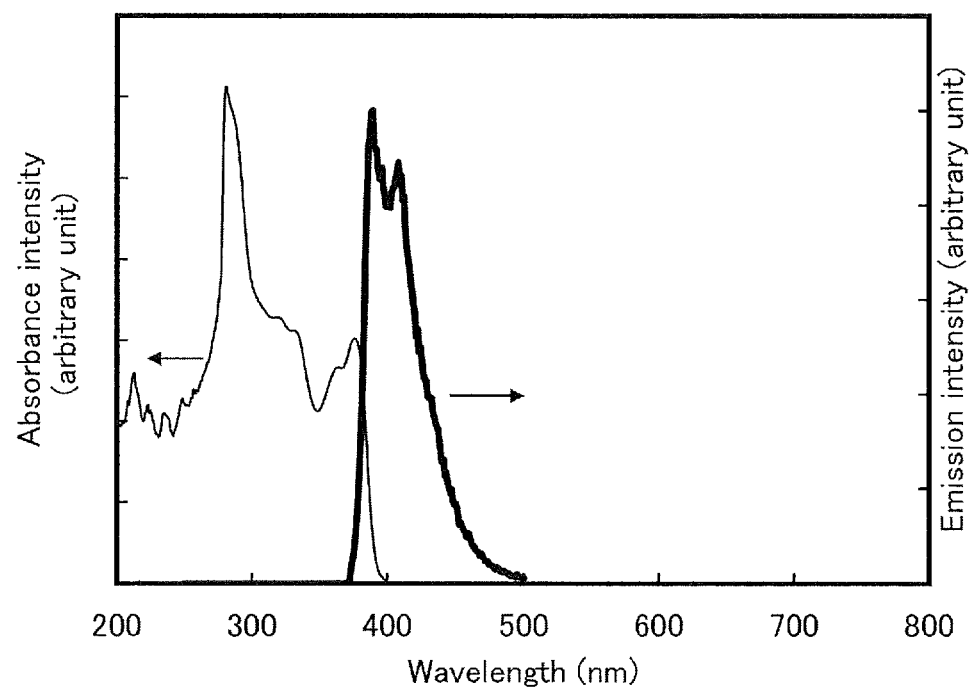
FIGS. 17A and 17B show an absorption and emission spectra of 2DBT2PDBq-II.
Figure 17B:
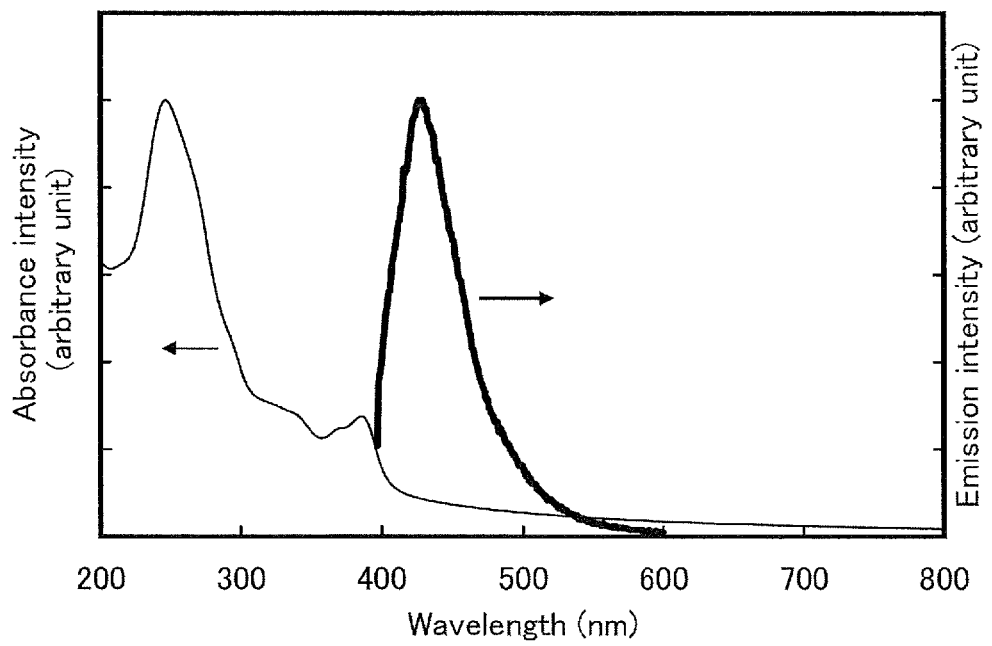

Next, absorption and emission spectra of 2DBT2PDBq-II in a toluene solution of 2DBT2PDBq-II are shown in FIG. 17A, and absorption and emission spectra of a thin film of 2DBT2PDBq-II are shown in FIG. 17B. The absorption spectrum was measured with a UV-visible spectrophotometer (V-550, manufactured by JASCO Corporation). A toluene solution of 2DBT2PDBq-II was put in a quartz cell and an absorption spectrum of 2DBT2PDBq-II in the toluene solution was measured. From this absorption spectrum, an absorption spectrum of the toluene solution measured with the quartz cell was subtracted, and the resultant value was shown in the drawing. In addition, as for the absorption spectrum of the thin film, a sample was prepared by evaporation of 2DBT2PDBq-II on a quartz substrate, and the absorption spectrum obtained by subtraction of an absorption spectrum of quartz from the absorption spectrum of this sample is shown in the drawing. The emission spectrum was measured with a UV-visible spectrophotometer (V-550, manufactured by JASCO Corporation) which was used for the measurement of the absorption spectrum. The emission spectrum of 2DBT2PDBq-II in a toluene solution of 2DBT2PDBq-II was measured with the toluene solution of 2DBT2PDBq-II put in a quartz cell, and the emission spectrum of the thin film was measured with a sample prepared by evaporation of 2DBT2PDBq-II on a quartz substrate. These show that the maximum absorption wavelengths of 2DBT2PDBq-II in the toluene solution of 2DBT2PDBq-II were around 373 nm and around 281 nm and that the maximum emission wavelengths thereof were around 389 nm and around 410 nm (an excitation wavelength of 363 nm). These also show that the maximum absorption wavelengths of the thin film were around 386 nm, around 370 nm, around 339 nm, around 316 nm, around 292 nm, around 265 nm, and around 246 nm and that the largest maximum emission wavelength thereof was around 428 nm (an excitation wavelength of 382 nm).

Further, the ionization potential of a thin film of 2DBT2PDBq-II was measured by a photoelectron spectrometer (AC-2, produced by Riken Keiki, Co., Ltd.) in the air. The obtained value of the ionization potential was converted to a negative value, so that the HOMO level of 2DBT2PDBq-II was −6.37 eV. From the data of the absorption spectra of the thin film in FIG. 17B, the absorption edge of 2DBT2PDBq-II, which was obtained from a Tauc plot with an assumption of direct transition, was 3.07 eV. Therefore, the optical energy gap of 2DBT2PDBq-H in the solid state was estimated at 3.07 eV; from the values of the HOMO level obtained above and this energy gap, the LUMO level of 2DBT2PDBq-II was able to be estimated at −3.30 eV. It was thus found that 2DBT2PDBq-II had a wide energy gap of 3.07 eV in the solid state. Accordingly, it can be said that the band gap and the triplet excitation energy were decreased because of the heterocyclic compound including an aromatic hydrocarbon group between a dibenzo[f,h]quinoxaline ring and two hole-transport skeletons.

Further, 2DBT2PDBq-II was analyzed by liquid chromatography mass spectrometry (abbreviation: LC/MS).

In the analysis by LC/MS, liquid chromatography (LC) separation was carried out with Acquity UPLC (manufactured by Waters Corporation), and mass spectrometry (MS) analysis was carried out with Xevo G2 T of MS (manufactured by Waters Corporation). An Acquity UPLC BEH C8 column (2.1 mm×100 mm, 1.7 μm) was used in the LC separation, where a column temperature was 40° C. Acetonitrile was used for Mobile Phase A and 0.1% of a formic acid solution was used for Mobile Phase B. A sample was prepared in such a manner that 2DBT2PDBq-II was dissolved in chloroform at a given concentration and the mixture was diluted with acetonitrile. An injection amount was 5.0 μL.

In the LC separation, a gradient method, in which composition of mobile phases is changed, was employed; the composition ratio of Mobile Phase A to Mobile Phase B was 75 to 25 for 0 minutes to 1 minute after the measurement started, and then the composition was changed, so that the ratio of Mobile Phase A to Mobile Phase B in the 10th minute was 95 to 5. The composition ratio was changed linearly.

In the MS analysis, ionization was carried out by an electrospray ionization (ESI) method. Capillary voltage and sample cone voltage were set to 3.0 kV and 30 V, respectively. Detection was performed in a positive mode. A mass range for the measurement was m/z=100 to 1200.

Figure 18A:
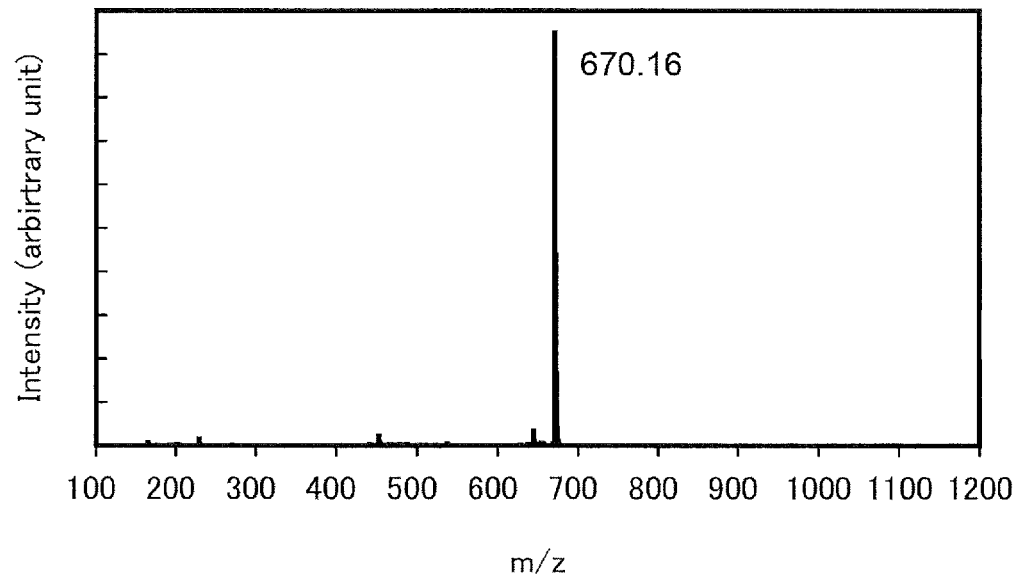
FIGS. 18A and 18B show LC/MS measurement results of 2DBT2PDBq-II (50 eV)
Figure 18B:
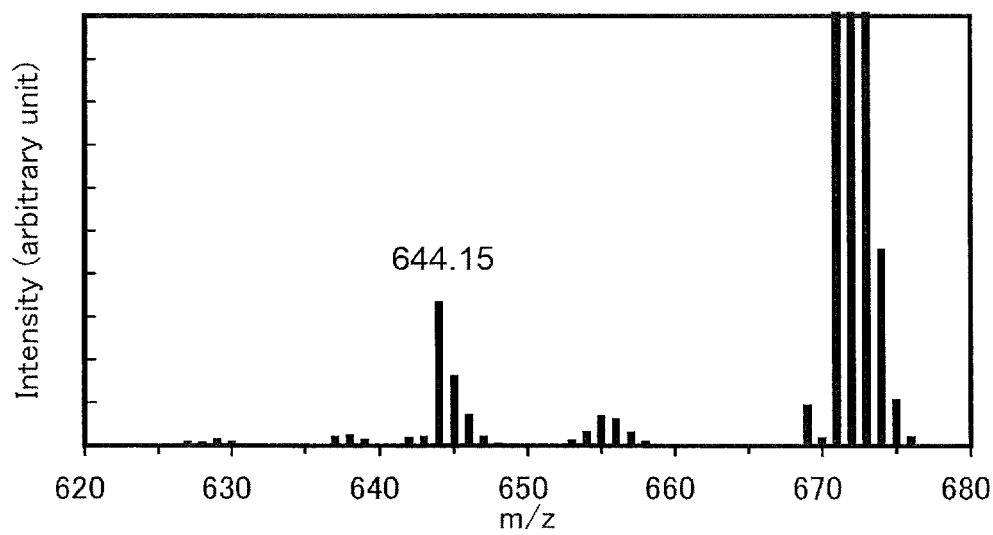
Figure 19A:
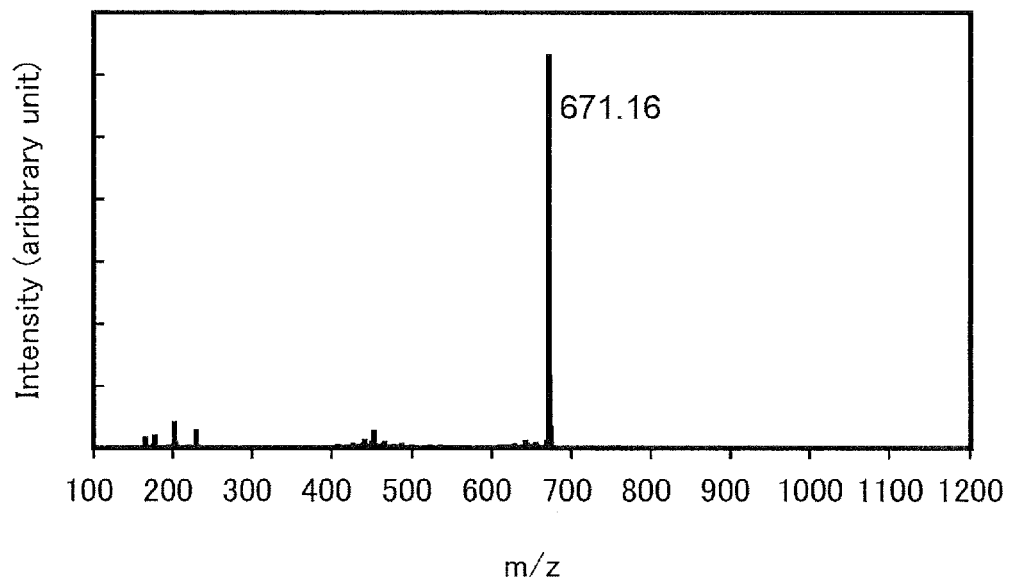
FIGS. 19A and 19B show LC/MS measurement results of 2DBT2PDBq-II (70 eV)
Figure 19B:
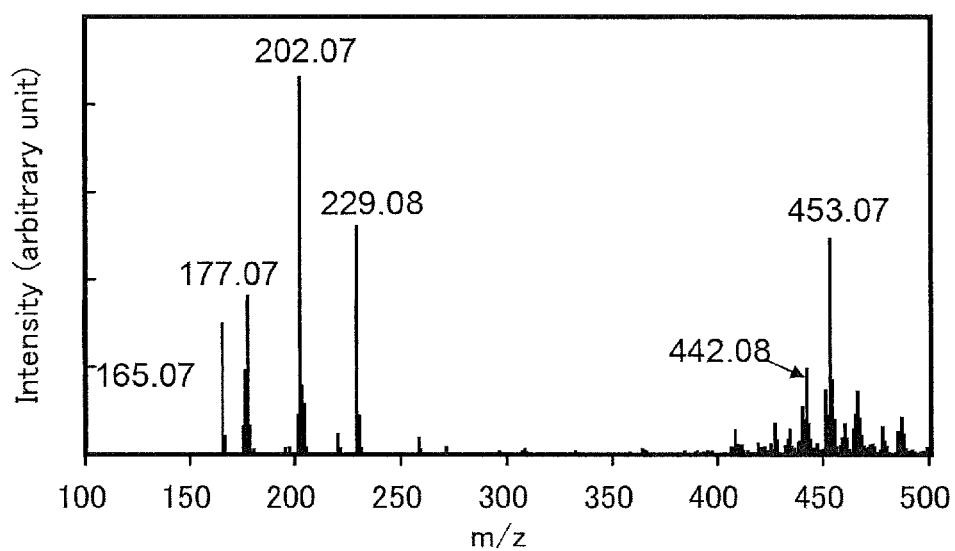

A component with m/z of 670.15 which underwent the separation and the ionization under the above-mentioned conditions was collided with an argon gas in a collision cell to dissociate into product ions. Energy (collision energy) for the collision with argon was 50 eV and 70 eV. The results of MS analysis of the dissociated product ions by time-of-flight (TOF) mass spectrometry are shown in FIGS. 18A and 18B and FIGS. 19A and 19B. FIGS. 18A and 18B show the results when the collision energy is 50 eV. FIGS. 19A and 19B show the results when the collision energy is 70 eV. Note that FIG. 18B is a graph where the m/z range in FIG. 18A is enlarged and FIG. 19B is a graph where the m/z range in FIG. 19A is enlarged.

The results in FIGS. 18A and 18B show that product ions of partial skeletons of 2DBT2PDBq-II are detected around m/z=644. Furthermore, the results in FIGS. 19A and 19B show that product ions of partial skeletons of 2DBT2PDBq-II are detected around m/z=229, m/z=202, m/z=177, and m/z=165.

The peak around m/z=644 is assumed to be a peak of a cation in a state where one C atom and one N atom are detached from 2DBT2PDBq-II. This peak is characteristic of a compound including a dibenzo[f,h]quinoxaline skeleton having a substituent at the 2-position, which is one feature of the heterocyclic compound of one embodiment of the present invention.

The peak around m/z=229 is assumed to be a peak of a cation of a diazatriphenylenyl group. Moreover, the peaks around m/z=202, m/z=177, and m/z=165 are also detected; therefore, the diazatriphenylenyl group is assumed to be a product ion derived from dibenzo[f,h]quinoxaline. These peaks are characteristic of a compound including a dibenzo[f,h]quinoxaline skeleton.

The above results indicate that 2DBT2PDBq-II, which is the heterocyclic compound of one embodiment of the present invention, includes a dibenzo[f,h]quinoxaline ring having a substituent at the 2-position.

In FIG. 19B, peaks relatively markedly appears around m/z=453 and around m/z=442. The peak around m/z=453 corresponds to a peak of a product ion composed of two dibenzothiophenyl groups, a benzene skeleton, and a carbon. The product ion is probably a phenyl group having two dibenzothiophenyl groups which removes from 2DBT2PDBq-II accompanied by a carbon at the 2-position. The peak around m/z=442 corresponds to a peak of a product ion composed of two dibenzothiophenyl groups and a benzene skeleton.

The peak around m/z=220 corresponds to a peak of a product ion of dibenzo[f,h]quinoxaline from which a carbon is removed. The product ion is probably dibenzo[f,h]quinoxaline skeleton of 2DBT2PDBq-II from which a phenyl group having two dibenzothiophenyl groups accompanied with a carbon at the 2-position is removed.

Example 4

In this example, a light-emitting element (Light-emitting Element 2) in which 2-[3,5-bis(dibenzothiophen-4-yl)phenyl]dibenzo[f,h]quinoxaline (abbreviation: 2DBT2PDBq-II) (the structural formula 200) which is the heterocyclic compound described in Embodiment 1 and synthesized in Example 3, is used as a host material and an electron-transport material in a light-emitting layer including an emission center substance emitting yellow-green phosphorescence. The heterocyclic compound is a compound in which an aromatic hydrocarbon group to which two hole-transport skeletons (dibenzothiophenyl groups) are bonded is bonded to a dibenzo[f,h]quinoxaline ring.

The molecular structures of organic compounds used in this example are shown in the following structural formulae (i), (ii), (v) to (vii) and (200). An element structure is the same as that of FIG. 1A.

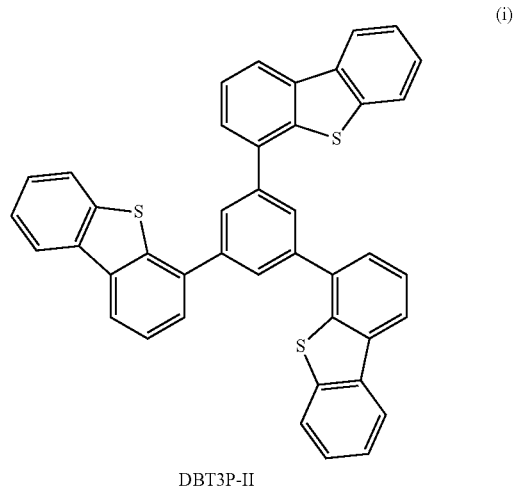

DBT3P-II (i)

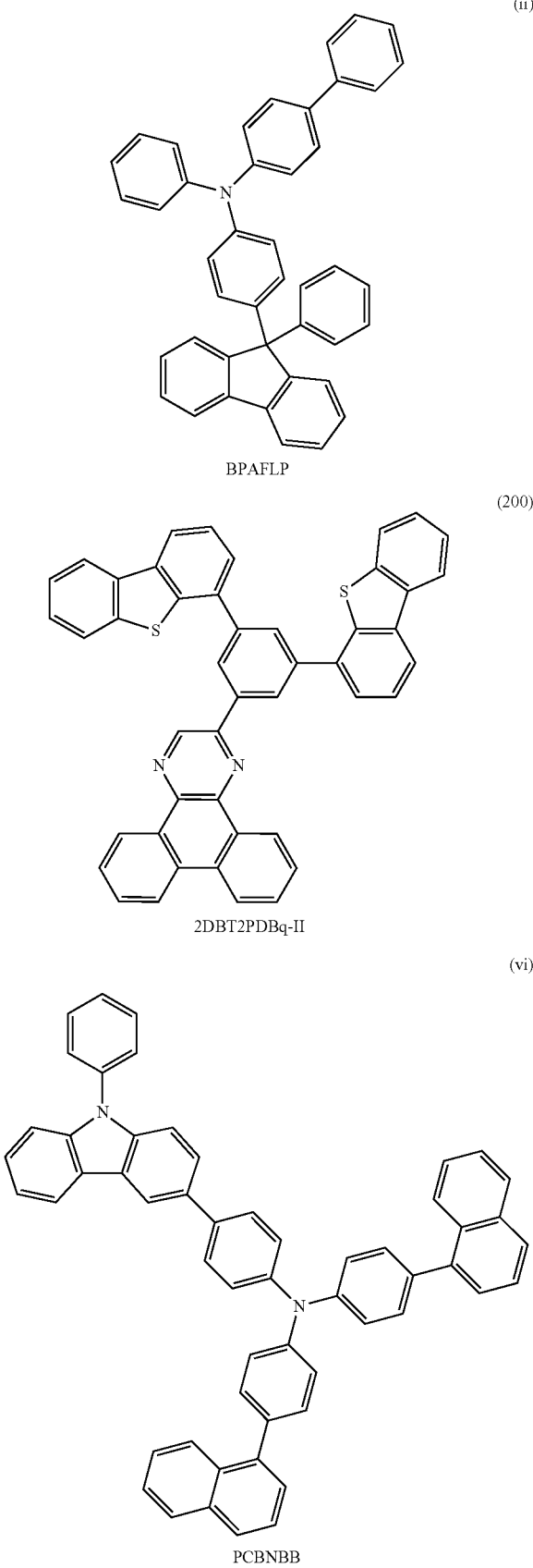

BPAFLP

2DBT2PDBq-II

PCBNBB

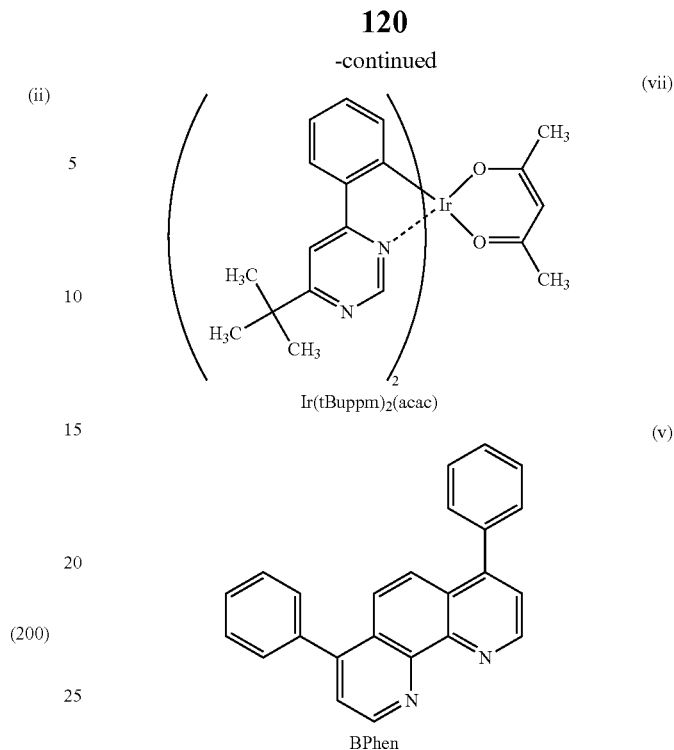

Ir(tBuppm)₂(acac)

BPhen

<<Fabrication of Light-Emitting Element 2>>

First, a glass substrate over which a film of indium tin oxide containing silicon (ITSO) was formed to a thickness of 110 nm was prepared as the first electrode 101. A surface of the ITSO film was covered with a polyimide film such that an area of 2 mm×2 mm of the surface was exposed, which corresponded to the electrode area. In pretreatment for forming the light-emitting elements over the substrate, the surface of the substrate was washed with water and baked at 200° C. for one hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed to a holder provided in the vacuum evaporation apparatus such that the surface of the substrate over which the ITSO film was formed faced downward.

After the pressure in the vacuum evaporation apparatus was reduced to $10^{-4}$ Pa, 1,3,5-tri(dibenzothiophen-4-yl)-benzene (abbreviation: DBT3P-II) represented by the above structural formula (i) and molybdenum(VI) oxide were co-evaporated so that the weight ratio of DBT3P-II:molybdenum oxide was 2:1; thus, the hole-injection layer 111 was formed. The thickness thereof was set to 20 nm. Note that the co-evaporation is an evaporation method in which a plurality of different substances is concurrently vaporized from the respective different evaporation sources.

Next, 4-phenyl-4'-(9-phenylfluoren-9-yl)triphenylamine (abbreviation: BPAFLP) represented by the above structural formula (ii) was evaporated to a thickness of 20 nm, thereby forming the hole-transport layer 112.

Furthermore, 2DBT2PDBq-II represented by the structural formula (200), 4,4'-di(1-naphthyl)-4"-(9-phenyl-9H-carbazol-3-yl)-triphenylamine (abbreviation: PCBNBB) represented by the structural formula (vi), and bis[2-(6-tertbutyl-4-pyrimidinyl-κN3)phenyl-κC] (2,4-pentanedionato-κ²O,O')iridium(III) (abbreviation: [Ir(tBuppm)₂(acac)]) represented by the structural formula (vii) are deposited over the hole-transport layer 112 to a thickness of 20 nm so that the weight ratio of 2DBT2PDBq-II to PCBNBB and [Ir(tBuppm)₂(acac)] is 0.7:0.3:0.05, and then evaporation was performed to a thickness of 20 nm so that the weight ratio of 2DBT2PDBq-II to PCBNBB and [Ir(tBuppm)₂(acac)] is 0.8:0.2:0.05, thereby forming the light-emitting layer 113.

Next, 2DBT2PDBq-II was evaporated to a thickness of 5 nm, and then bathophenanthroline (abbreviation: BPhen) represented by the above structural formula (v) was evaporated to a thickness of 20 nm, so that the electron-transport layer 114 was formed.

Further, lithium fluoride was evaporated to a thickness of 1 nm over the electron-transport layer 114, so that the electron-injection layer was formed. Lastly, an aluminum film was formed to a thickness of 200 nm as the second electrode 102 functioning as a cathode. Accordingly, Light-emitting Element 2 was completed. Note that in the above evaporation processes, evaporation was all performed by a resistance heating method. Light-emitting Element 2 corresponds to the light-emitting element described in detail in Embodiment 2.

<<Operation Characteristics of Light-Emitting Element 2>>

Light-emitting Element 2 thus obtained was sealed in a glove box under a nitrogen atmosphere without being exposed to the air (specifically, a sealing material was applied onto an outer edge and heat treatment was performed at 80° C. for one hour at the time of sealing). Then, the operation characteristics of the light-emitting element were measured. Note that the measurement was carried out at room temperature (in an atmosphere kept at 25° C.).

Figure 20:
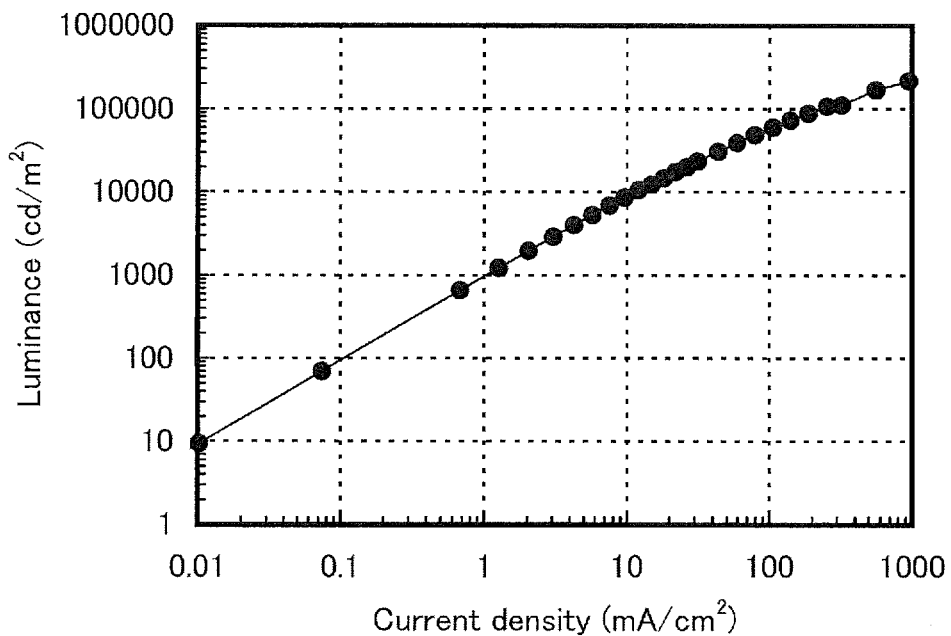
FIG. 20 shows the current density-luminance characteristics of Light-emitting Element 2.
Figure 21:
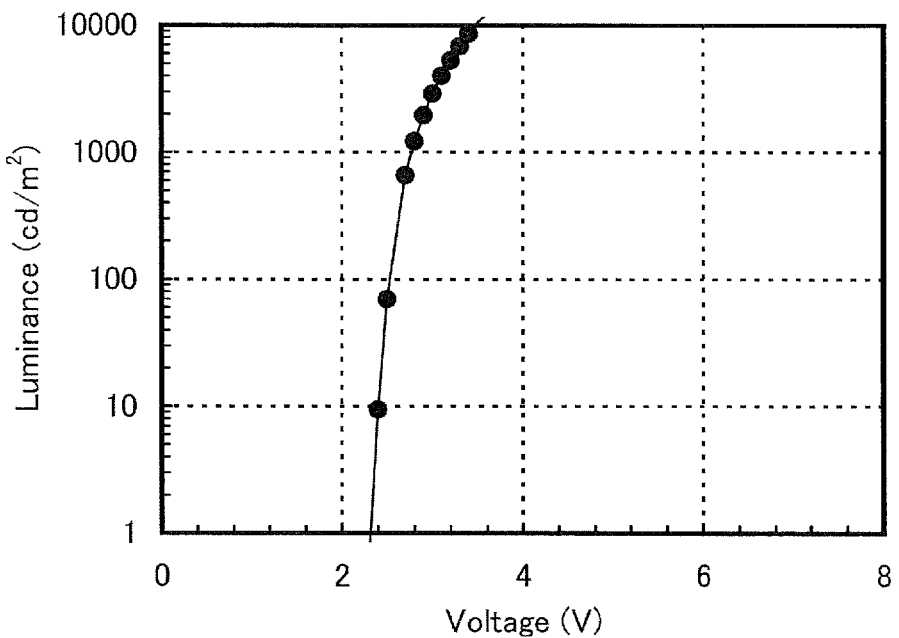
FIG. 21 shows the voltage-luminance characteristics of Light-emitting Element 2.
Figure 22:
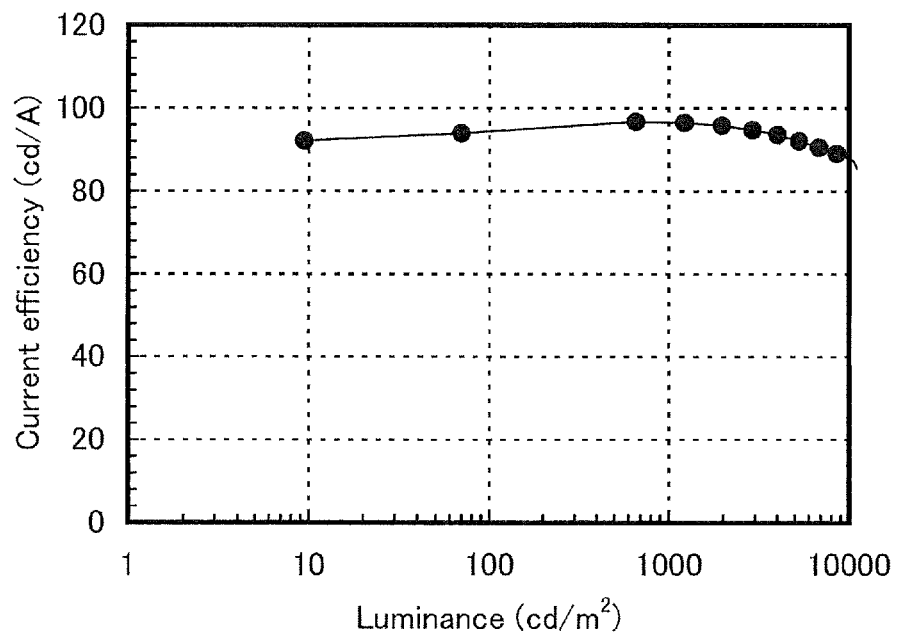
FIG. 22 shows the luminance-current efficiency characteristics of Light-emitting Element 2.
Figure 23:
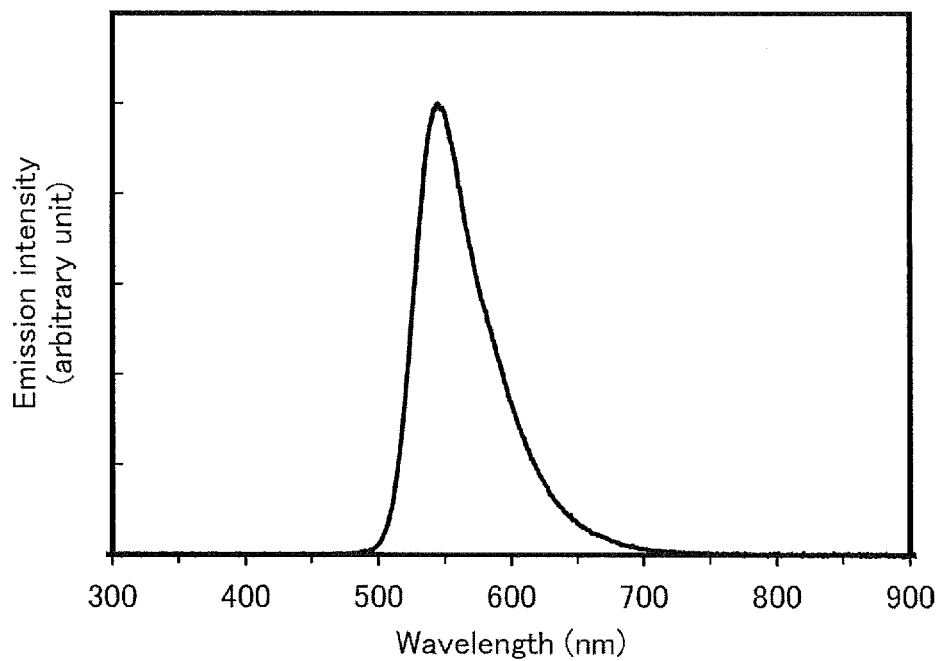
FIG. 23 shows an emission spectrum of Light-emitting Element 2.

FIG. 20 shows current density-luminance characteristics of Light-emitting Element 2, FIG. 21 shows voltage-luminance characteristics thereof, FIG. 22 shows luminance-current efficiency characteristics thereof, and FIG. 23 shows an emission spectrum thereof.

FIG. 22 shows that Light-emitting Element 2 exhibits favorable luminance-current efficiency characteristics; thus, the element has high emission efficiency. Moreover, FIG. 21 shows that Light-emitting Element 2 exhibits favorable voltage-luminance characteristics and is a light-emitting element having low driving voltage. This indicates that the heterocyclic compound described in Embodiment 1 has an excellent carrier-transport property. Therefore, a light-emitting element including a compound comprising a dibenzo[f,h]quinoxaline ring and two hole-transport skeletons, where the dibenzo[f,h]quinoxaline ring and the two hole-transport skeletons are bonded to an aromatic hydrocarbon group is a light-emitting element having high emission efficiency. In addition, the light-emitting element is a light-emitting element having low driving voltage.

Reference Example 1

An example of synthesizing an organometallic complex, bis[2-(6-tert-butyl-4-pyrimidinyl-κN3)phenyl-κC](2,4-pentanedionato-κ²O,O')iridium(III) (abbreviation: [Ir(tBuppm)₂(acac)]), which is used in the above Example. A structure of [Ir(tBuppm)₂(acac)] is shown below.

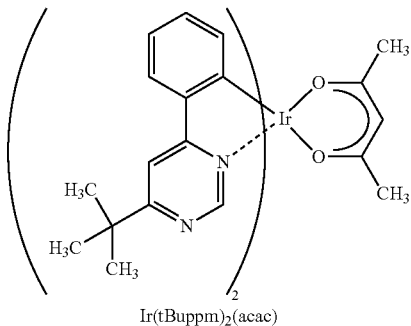

Ir(tBuppm)₂(acac)

Step 1: Synthesis of 4-tert-butyl-6-phenylpyrimidine (abbreviation: HtBuppm)

First, into a recovery flask equipped with a reflux pipe were put 22.5 g of 4,4-dimethyl-1-phenylpentane-1,3-dione and 50 g of formamide, and the air in the flask was replaced with nitrogen. This reaction container was heated, so that the reacted solution was refluxed for five hours. After that, this solution was poured into aqueous sodium hydroxide, and an organic layer was extracted with dichloromethane. The obtained organic layer was washed with water and saturated saline, and dried with magnesium sulfate. The solution which had been dried was filtered. The solvent of this solution was distilled off, and then the obtained residue was purified by silica gel column chromatography using hexane and ethyl acetate as a developing solvent in a volume ratio of 10:1, so that a pyrimidine derivative HtBuppm (colorless oily substance, yield of 14%) was obtained. A scheme of the synthesis of Step 1 is shown below.

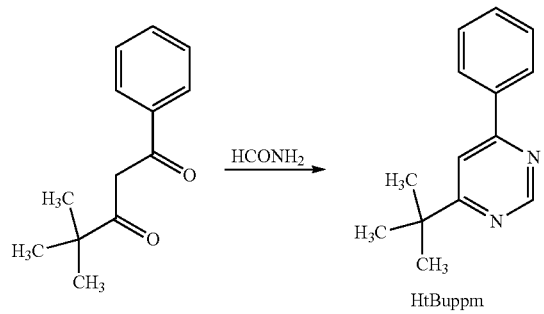

Step 2: Synthesis of di-μ-chloro-bis[bis(6-tert-butyl-4-phenylpyrimidinato)iridium(III)] (abbreviation: [Ir(tBuppm)₂Cl]₂)

Next, into a recovery flask equipped with a reflux pipe were put 15 mL of 2-ethoxyethanol, 5 mL of water, 1.49 g of HtBuppm obtained in Step 1, and 1.04 g of iridium chloride hydrate (IrCl₃×H₂O), and the air in the flask was replaced with argon. After that, irradiation with microwaves (2.45 GHz, 100 W) was performed for one hour to cause a reaction. The solvent was distilled off, and then the obtained residue was suction-filtered with ethanol and washed to give a dinuclear complex [Ir(tBuppm)₂Cl]₂ (yellow-green powder, yield of 73%). A synthesis scheme of Step 2 is shown below.

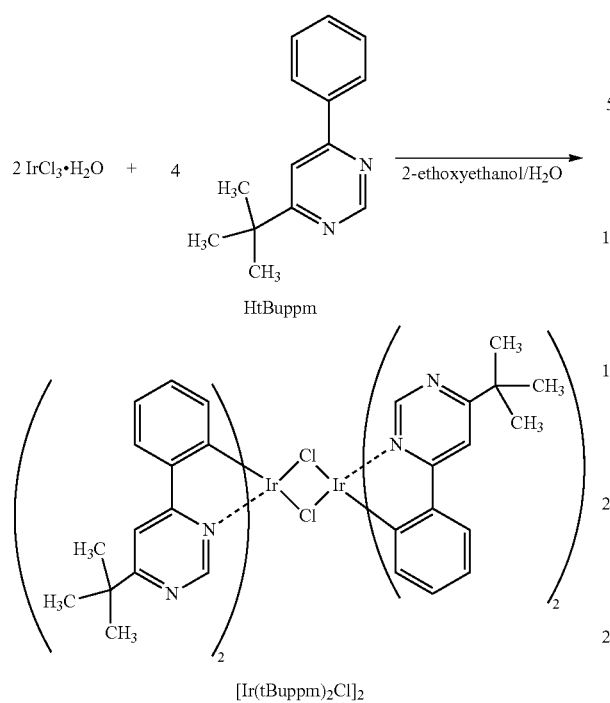

[Ir(tBuppm)₂Cl]₂

Step 3: Synthesis of bis[2-(6-tert-butyl-4-pyrimidinyl-κN3)phenyl-κC](2,4-pentanedionato-κ²O,O') iridium(III) (abbreviation: [Ir(tBuppm)₂(acac)])

Furthermore, into a recovery flask equipped with a reflux pipe were put 40 mL of 2-ethoxyethanol, 1.61 g of the dinuclear complex [Ir(tBuppm)₂Cl]₂ obtained in Step 2, 0.36 g of acetylacetone, and 1.27 g of sodium carbonate, and the air in the flask was replaced with argon. After that, irradiation with microwaves (2.45 GHz, 120 W) was performed for one hour to cause a reaction. The solvent was distilled off, and the obtained residue was suction-filtered with ethanol and washed with water and then with ethanol. This solid was dissolved in dichloromethane, and the mixture was filtered through a filter aid in which Celite (produced by Wako Pure Chemical Industries, Ltd., Catalog No. 531-16855), alumina, and Celite were stacked in this order. The solvent was distilled off, and the obtained solid was recrystallized from a mixed solvent of dichloromethane and hexane, so that yellow powder was obtained as a target substance (yield of 68%). A synthesis scheme of Step 3 is shown below.

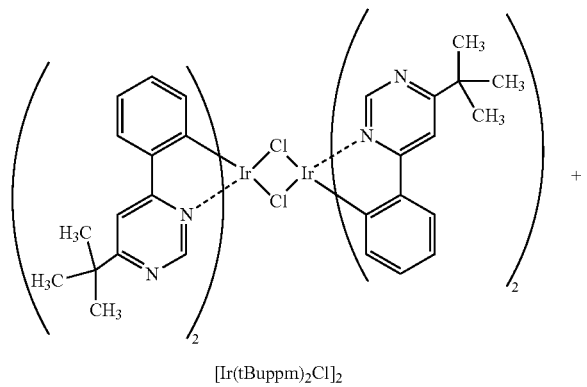

[Ir(tBuppm)₂Cl]₂

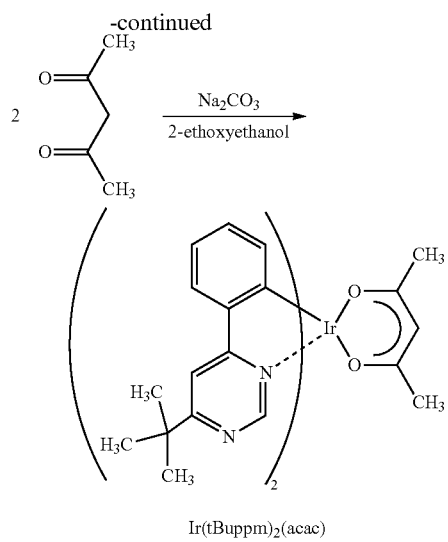

Ir(tBuppm)₂(acac)

The yellow powder obtained in Step 3 was measured by nuclear magnetic resonance spectrometry (¹H-NMR). The measurement data are shown below. These results revealed that the organometallic complex [Ir(tBuppm)₂(acac)] was obtained. These results show that the organometallic complex [Ir(tBuppm)₂(acac)] was obtained.

¹H NMR. δ (CDCl₃): 1.50 (s, 18H), 1.79 (s, 6H), 5.26 (s, 1H), 6.33 (d, 2H), 6.77 (t, 2H), 6.85 (t, 2H), 7.70 (d, 2H), 7.76 (s, 2H), 9.02 (s, 2H)

This application is based on Japanese Patent Application serial no. 2011-187669 filed with Japan Patent Office on Aug. 30, 2011, the entire contents of which are hereby incorporated by reference.

What is claimed is:

1. A heterocyclic compound represented by a general formula (G1),

(G1)

wherein:
A¹ and A² each independently represent any of a substituted or unsubstituted carbazolyl group, a substituted or unsubstituted dibenzofuranyl group, and a substituted or unsubstituted dibenzothiophenyl group;
B represents a substituted or unsubstituted dibenzo[f,h]quinoxalinyl group; and
Ar represents a substituted or unsubstituted aromatic hydrocarbon group having 6 to 13 carbon atoms, and the Ar is bonded to a 2-position of the substituted or unsubstituted dibenzo[f,h]quinoxaline ring.

2. The heterocyclic compound according to claim 1, wherein the aromatic hydrocarbon group has a substituent.

3. The heterocyclic compound according to claim 1, wherein the aromatic hydrocarbon group has substituents, and
wherein the substituents are bonded to each other to form a ring.

4. The heterocyclic compound according to claim 1, represented by a general formula (G2),

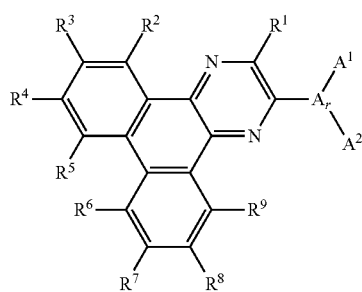

(G2)

wherein:
R¹ to R⁹ each independently represent any of hydrogen, an alkyl group having 1 to 4 carbon atoms, and a substituted or unsubstituted aryl group having 6 to 13 carbon atoms.

5. The heterocyclic compound according to claim 4, wherein the aromatic hydrocarbon group has a substituent.

6. The heterocyclic compound according to claim 4, wherein the aromatic hydrocarbon group has substituents, and
wherein the substituents are bonded to each other to form a ring.

7. The heterocyclic compound according to claim 1, represented by a general formula (G3-1),

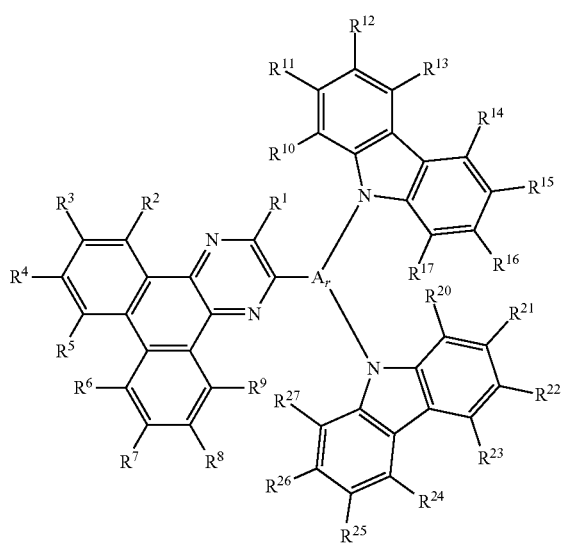

(G3-1)

wherein:
R¹ to R⁹, R¹⁰ to R¹⁷, and R²⁰ to R²⁷ each independently represent any of hydrogen, an alkyl group having 1 to 4 carbon atoms, and a substituted or unsubstituted aryl group having 6 to 13 carbon atoms.

8. The heterocyclic compound according to claim 7, wherein the aromatic hydrocarbon group has a substituent.

9. The heterocyclic compound according to claim 7, wherein the aromatic hydrocarbon group has substituents, and
wherein the substituents are bonded to each other to form a ring.

10. The heterocyclic compound according to claim 1, represented by a general formula (G3-2),

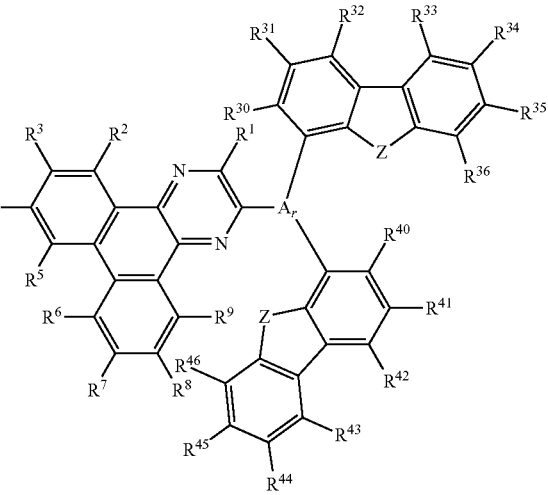

(G3-2)

wherein:
R¹ to R⁹, R³⁰ to R³⁶, and R⁴⁰ to R⁴⁶ each independently represent any of hydrogen, an alkyl group having 1 to 4 carbon atoms, and a substituted or unsubstituted aryl group having 6 to 13 carbon atoms; and
Z represents oxygen or sulfur.

11. The heterocyclic compound according to claim 10, wherein the aromatic hydrocarbon group has a substituent.

12. The heterocyclic compound according to claim 10, wherein the aromatic hydrocarbon group has substituents, and
wherein the substituents are bonded to each other to form a ring.

13. The heterocyclic compound according to claim 1, represented by a general formula (G4-1),

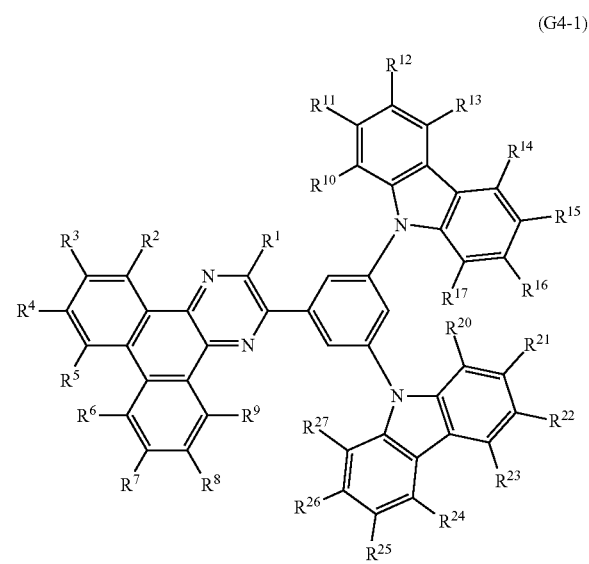

(G4-1)

wherein:
R¹ to R⁹, R¹⁰ to R¹⁷, and R²⁰ to R²⁷ each independently represent any of hydrogen, an alkyl group having 1 to 4 carbon atoms, and a substituted or unsubstituted aryl group having 6 to 13 carbon atoms.

14. The heterocyclic compound according to claim 1, represented by a general formula (G4-2),

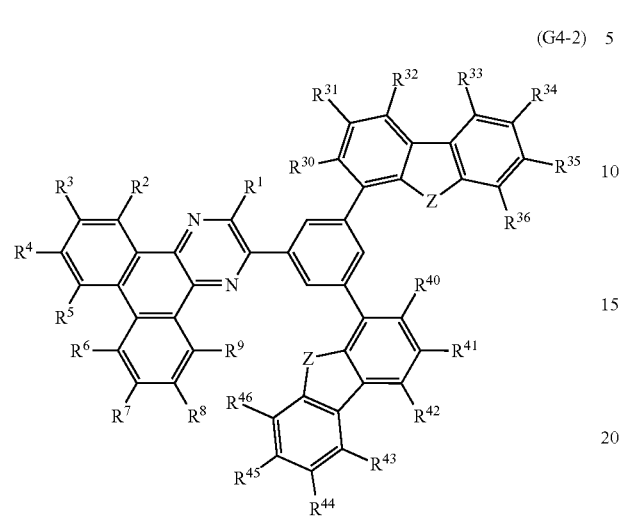
(G4-2)

wherein:

R$^1$ to R$^9$, R$^{30}$ to R$^{36}$, and R$^{40}$ to R$^{46}$ each independently represent any of hydrogen, an alkyl group having 1 to 4 carbon atoms, and a substituted or unsubstituted aryl group having 6 to 13 carbon atoms; and Z represents oxygen or sulfur.

15. The heterocyclic compound according to claim 5, represented by a general formula (G5-1),

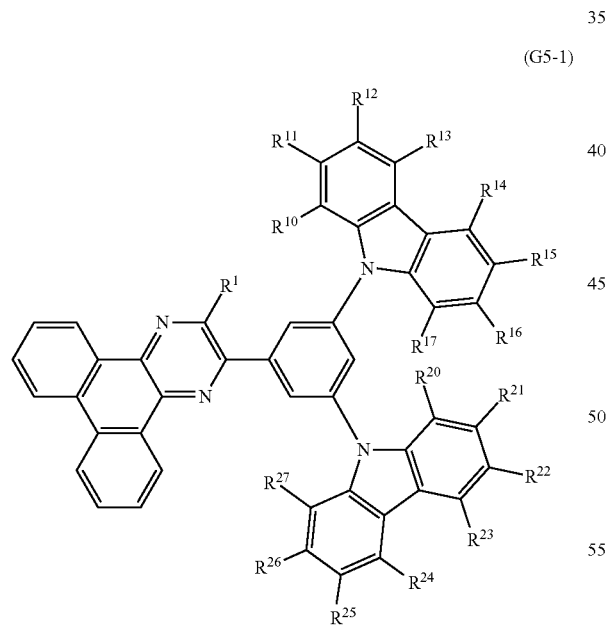
(G5-1)

wherein:

R$^1$, R$^{10}$ to R$^{17}$, and R$^{20}$ to R$^{27}$ each independently represent any of hydrogen, an alkyl group having 1 to 4 carbon atoms, and a substituted or unsubstituted aryl group having 6 to 13 carbon atoms.

16. The heterocyclic compound according to claim 1, represented by a general formula (G5-2),

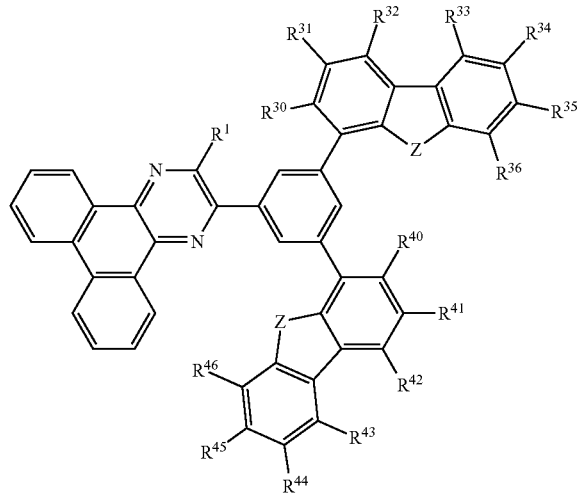
(G5-2)

wherein:

R$^1$, R$^{30}$ to R$^{36}$, and R$^{40}$ to R$^{46}$ each independently represent any of hydrogen, an alkyl group having 1 to 4 carbon atoms, and a substituted or unsubstituted aryl group having 6 to 13 carbon atoms; and Z represents oxygen or sulfur.

17. The heterocyclic compound according to claim 1, represented by a general formula (G6),

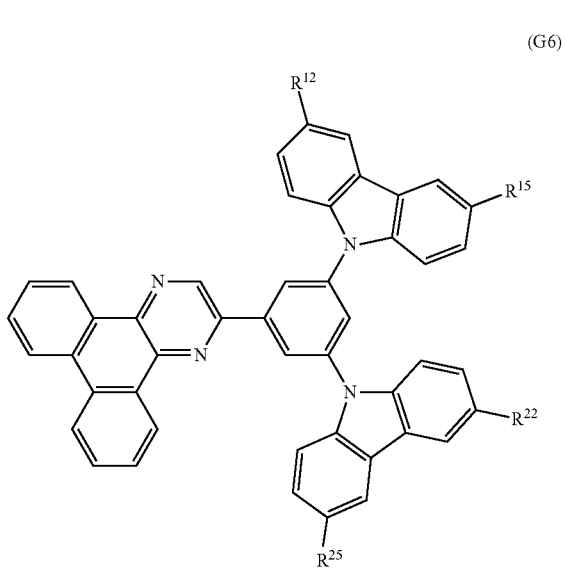
(G6)

wherein:

R$^{12}$, R$^{15}$, R$^{22}$, and R$^{25}$ each independently represent any of hydrogen, an alkyl group having 1 to 4 carbon atoms, and a substituted or unsubstituted aryl group having 6 to 13 carbon atoms.

18. The heterocyclic compound according to claim 1, wherein the heterocyclic compound represented by a structural formula (100)

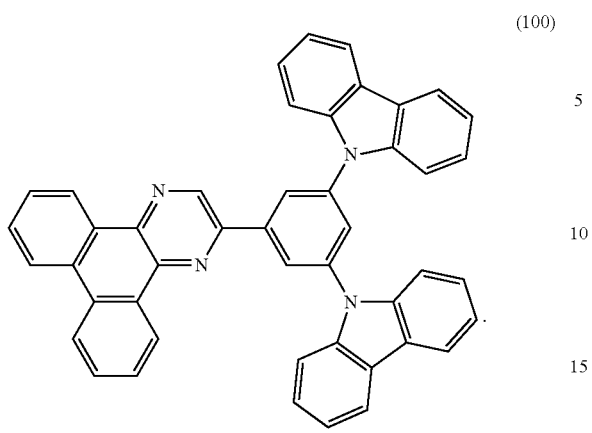
(100)

19. A light-emitting element comprising:
a pair of electrodes; and
a layer containing an organic compound between the pair of electrodes,
wherein the layer containing the organic compound includes the heterocyclic compound according to claim 1.

20. A light-emitting device comprising the light-emitting element according to claim 19.

21. A light-emitting device comprising the light-emitting element according to claim 19.

22. An electronic device comprising the light-emitting element according to claim 19.

* * * * *